US010668139B2

(12) United States Patent
Galvin et al.

(10) Patent No.: US 10,668,139 B2
(45) Date of Patent: *Jun. 2, 2020

(54) MYCOPLASMA HYOPNEUMONIAE VACCINE

(71) Applicant: Zoetis Services LLC, Parsippany, NJ (US)

(72) Inventors: Jeffrey E. Galvin, Lincoln, NE (US); Gregory P. Nitzel, Paw Paw, MI (US); John Keith Garrett, North Wilkesboro, NC (US); James R. Kulawik, II, Lincoln, NE (US); Tracy L. Ricker, Portage, MI (US); Megan Marie Smutzer, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/249,031

(22) Filed: Jan. 16, 2019

(65) Prior Publication Data

US 2019/0134176 A1    May 9, 2019

Related U.S. Application Data

(60) Continuation of application No. 15/480,949, filed on Apr. 6, 2017, now Pat. No. 10,206,991, which is a continuation of application No. 14/712,393, filed on May 14, 2015, now Pat. No. 9,650,600, which is a division of application No. 13/850,318, filed on Mar. 26, 2013, now Pat. No. 9,120,859.

(60) Provisional application No. 61/620,165, filed on Apr. 4, 2012.

(51) Int. Cl.
| | | |
|---|---|---|
| *A61K 39/02* | (2006.01) | |
| *A61K 39/12* | (2006.01) | |
| *A61K 39/295* | (2006.01) | |
| *C07K 14/30* | (2006.01) | |
| *C12N 1/36* | (2006.01) | |
| *A61K 39/39* | (2006.01) | |
| *A61K 39/00* | (2006.01) | |

(52) U.S. Cl.
CPC ...... *A61K 39/0241* (2013.01); *A61K 39/0208* (2013.01); *A61K 39/12* (2013.01); *A61K 39/295* (2013.01); *A61K 39/39* (2013.01); *C07K 14/30* (2013.01); *C12N 1/36* (2013.01); *A61K 2039/521* (2013.01); *A61K 2039/5252* (2013.01); *A61K 2039/552* (2013.01); *A61K 2039/55566* (2013.01); *A61K 2039/70* (2013.01); *C12N 2750/10021* (2013.01); *C12N 2750/10034* (2013.01); *C12N 2750/10063* (2013.01); *C12N 2770/10034* (2013.01)

(58) Field of Classification Search
None
See application file for complete search history.

(56) References Cited

U.S. PATENT DOCUMENTS

| | | |
|---|---|---|
| 4,606,918 A | 8/1986 | Allison et al. |
| 4,681,870 A | 7/1987 | Balint et al. |
| 5,080,896 A | 1/1992 | Visser et al. |
| 5,084,269 A | 1/1992 | Kullenberg |
| 5,240,706 A | 8/1993 | Faulds et al. |
| 5,252,328 A | 10/1993 | Faulds et al. |
| 5,338,543 A | 8/1994 | Fitzgerald et al. |
| 5,534,256 A | 7/1996 | Potter et al. |
| 5,565,205 A | 10/1996 | Petersen et al. |
| 5,620,691 A | 4/1997 | Wensvoort et al. |
| 5,695,766 A | 12/1997 | Paul et al. |
| 5,695,769 A | 12/1997 | Frantz et al. |
| 5,788,962 A | 8/1998 | Wise et al. |
| 5,846,735 A | 12/1998 | Stapleton et al. |
| 6,110,467 A | 8/2000 | Paul et al. |
| 6,113,916 A | 9/2000 | Bhogal et al. |
| 6,162,435 A | 12/2000 | Minion et al. |
| 6,193,971 B1 | 2/2001 | Hofmann et al. |
| 6,251,397 B1 | 6/2001 | Paul et al. |
| 6,251,404 B1 | 6/2001 | Paul et al. |
| 6,268,199 B1 | 7/2001 | Meulenberg et al. |
| 6,342,231 B1 | 1/2002 | Burkhardt et al. |
| 6,380,376 B1 | 4/2002 | Paul et al. |
| 6,500,662 B1 | 12/2002 | Calvert et al. |
| 6,585,981 B1 | 7/2003 | Pijoan |
| 6,592,873 B1 | 7/2003 | Paul et al. |
| 6,753,417 B2 | 6/2004 | Hansen et al. |
| 6,773,908 B1 | 8/2004 | Paul et al. |
| 6,846,477 B2 | 1/2005 | Keich et al. |
| 6,977,078 B2 | 12/2005 | Paul et al. |

(Continued)

FOREIGN PATENT DOCUMENTS

| | | |
|---|---|---|
| EP | 0283840 A2 | 3/1988 |
| EP | 0283085 A1 | 9/1988 |

(Continued)

OTHER PUBLICATIONS

Collins et al. "Isolation of Swine Infertility and Respiratory Syndrome Virus (Isolate ATCC VR-2332) in North America and Experimental Reproduction of the Disease in Gnotobiotic Pigs" Journal of Veterinary Diagnostic Investigation 1992, 4:117-126.

Kwang, J. et al. "Cloning, Expression, and Sequence Analysis of the ORF4 Gene of the Porcine Reproductive and Respiratory Syndrome Virus MN-1b" Journal of Veterinary Diagnostic Investigation 1994, 6:293-296.

Mardassi, H. et al. "Molecular Analysis of the ORFs 3 to 7 of Porcine Reproductive and Respiratory Syndrome Virus, Quebec Reference Strain" Archives of Virology 1995, 140:1405-1418.

Meng, X.-J. et al. "Molecular Cloning and Nucleotide Sequencing of the 3'-Terminal Genomic RNA of the Porcine Reproductive and Respiratory Syndrome Virus" Journal of General Virology 1994, 75:1795-1801.

(Continued)

*Primary Examiner* — Shanon A. Foley
(74) *Attorney, Agent, or Firm* — Gloria K. Szakiel

(57) ABSTRACT

This invention provides a protein-A or protein-G treated *Mycoplasma hyopneumoniae* (M.hyo) antigen that is compatible with antigens from other swine pathogens, wherein the M.hyo antigen is an M.hyo culture supernatant.

28 Claims, 10 Drawing Sheets

(56) References Cited

U.S. PATENT DOCUMENTS

| | | | |
|---|---|---|---|
| 7,018,638 B2 | 3/2006 | Chu et al. | |
| 7,056,492 B2 | 6/2006 | Goudie et al. | |
| 7,074,894 B2 | 7/2006 | Walker et al. | |
| 7,169,394 B2 | 1/2007 | Chu et al. | |
| 7,223,854 B2 | 5/2007 | Paul et al. | |
| 7,264,802 B2 | 9/2007 | Paul et al. | |
| 7,264,957 B2 | 9/2007 | Paul et al. | |
| 7,279,166 B2 | 10/2007 | Meng et al. | |
| 7,419,806 B2 | 9/2008 | Minion et al. | |
| 7,517,976 B2 | 4/2009 | Paul et al. | |
| 7,575,752 B2 | 8/2009 | Meng et al. | |
| 7,622,124 B2 | 11/2009 | Chu et al. | |
| 7,959,927 B2 | 6/2011 | Chu et al. | |
| 8,008,001 B2 | 8/2011 | Roerink et al. | |
| 8,187,588 B2 | 5/2012 | Chu et al. | |
| 8,444,989 B1 | 5/2013 | Ohnesorge et al. | |
| RE44,399 E | 7/2013 | Keich et al. | |
| 8,546,149 B2 | 10/2013 | Allen et al. | |
| 9,120,859 B2 * | 9/2015 | Galvin | C07K 14/30 |
| 9,125,885 B2 * | 9/2015 | Nitzel | A61K 39/295 |
| 9,125,886 B2 * | 9/2015 | Nitzel | A61K 39/295 |
| 9,599,607 B2 | 3/2017 | Allen et al. | |
| 9,649,369 B2 | 5/2017 | Nitzel | |
| 9,650,600 B2 | 5/2017 | Galvin | |
| 9,650,601 B2 | 5/2017 | Nitzel | |
| 9,687,544 B2 | 6/2017 | Thevenon et al. | |
| 10,206,991 B2 * | 2/2019 | Galvin | C07K 14/30 |
| 10,206,993 B2 * | 2/2019 | Nitzel | A61K 39/295 |
| 2002/0114817 A1 | 8/2002 | Liem et al. | |
| 2003/0092897 A1 | 5/2003 | Walker et al. | |
| 2005/0079185 A1 | 4/2005 | Parisot et al. | |
| 2006/0286123 A1 | 12/2006 | Fetzer et al. | |
| 2009/0017064 A1 * | 1/2009 | Wu | A61K 39/12 424/205.1 |
| 2009/0092636 A1 | 4/2009 | Roof et al. | |
| 2009/0117152 A1 | 5/2009 | Chu et al. | |
| 2009/0317423 A1 | 12/2009 | Roof et al. | |
| 2012/0052514 A1 | 3/2012 | Allen et al. | |
| 2013/0183338 A1 | 7/2013 | Jacobs et al. | |
| 2013/0266601 A1 | 10/2013 | Galvin et al. | |
| 2017/0136117 A1 | 5/2017 | Calvert | |

FOREIGN PATENT DOCUMENTS

| | | |
|---|---|---|
| EP | 0315153 A2 | 5/1989 |
| EP | 0595436 A2 | 5/1994 |
| EP | 0325191 B1 | 9/1995 |
| EP | 2 275 132 A2 | 1/2011 |
| EP | 2 327 787 A1 | 6/2011 |
| EP | 2 217 271 B1 | 5/2016 |
| EP | 1 968 630 B1 | 1/2018 |
| GB | 2282811 | 4/1995 |
| WO | WO 1991/03157 | 3/1991 |
| WO | WO 1991/18627 | 12/1991 |
| WO | WO 1992/21375 | 12/1992 |
| WO | WO 1993/03760 | 3/1993 |
| WO | WO 1993/07898 | 4/1993 |
| WO | WO 1993/10216 | 5/1993 |
| WO | WO 1993/14196 | 7/1993 |
| WO | WO 1995/30437 | 11/1995 |
| WO | WO 1996/28472 A1 | 9/1996 |
| WO | WO 1996/40268 | 12/1996 |
| WO | WO 2002/10343 A2 | 2/2002 |
| WO | WO 2002/49666 A2 | 6/2002 |
| WO | WO 03003941 A2 | 1/2003 |
| WO | WO 2003/049703 A2 | 6/2003 |
| WO | WO 2004058142 A2 | 7/2004 |
| WO | WO 2007/116032 A1 | 10/2007 |
| WO | WO 2009/126356 A2 | 10/2009 |
| WO | WO 2009/127684 * | 10/2009 |
| WO | WO 2009/127684 A1 | 10/2009 |
| WO | WO 2011/141443 A1 | 11/2011 |
| WO | WO 2012/025612 A1 | 3/2012 |
| WO | WO 2012/063212 A1 | 5/2012 |
| WO | WO 2013/152083 A2 | 10/2013 |
| WO | WO 2013/152086 A1 | 10/2013 |

OTHER PUBLICATIONS

Wensvoort, G. et al. "Mystery Swine Disease in the Netherlands: the Isolation of Lelystad Virus" The Veterinary Quarterly 1991, 13:121-130.

Kim et al. "Identification and Mapping of an Immunogenic Region of Mycoplasma Hyopneumoniae p65 Surface Lipoprotein Expressed in Escherichia coli from a Cloned Genomic Fragment" Infection and Immunity 1990, 58:2637-2643.

Futo et al. "Molecular Cloning of a 46-Kilodalton Surface Antigen (P46) Gene from Mycoplasma Hyopneumoniae: Direct Evidence of CGG Codon Usage for Arginine" Journal of Bacteriology 1995, 177:1915-1917.

Zhang et al. "Identification and Characterization of a Mycoplasma Hyopneumoniae Adhesin" Infection and Immunity 1995, 63: 1013-1029.

King et al. "Characterization of the Gene Encoding Mhp1 from Mycoplasma Hyopneumoniae and Examination of Mhp1's Vaccine Potential" Vaccine 1997, 15:25-35.

Okada et al. "Protective Effect of Vaccination with Culture Supernate of M.Hyopneumoniae Against Experimental Infection in Pigs" Journal of Veterinary Medicine 2000, 47:527-533.

Scarman et al. "Identification of Novel Species-Specific Antigens of Mycoplasma Hyopneumoniae by Preparative SDS-PAGE ELISA Profiling" Microbiology 1997, 143:663-673.

Strait et al. "Efficacy of a Mycoplasma Hyopneumoniae Bacterin in Pigs Challenged With Two Contemporary Pathogenic Isolates of M Hyopneumoniae" Journal of Swine Health and Production 2008, 16:200-206.

Alexander et al. "Adjuvants and their Modes of Action" Livestock Production Science 1995, 42:153-162.

Hunter et al. "The Adjuvant Activity of Nonionic Block Polymer Surfactants" The Journal of Immunologists 1981, 127:1244-1250.

Allison "Squalene and Squalane Emulsions as Adjuvants" Methods 1999, 19:87-93.

Goodwin et al. "Enzootic Pneumonia of Pigs: Immunization Attempts Inoculating Mycoplasma Suipneumoniae Antigen by Various Routes and with Different Adjuvants" British Veterinary Journal 1973, 129:456-464.

George et al. "Route-Related Variation in the Immunogenicity of Killed Salmonella Enteritidis Vaccine: Role of Antigen Presenting Cells" Microbiol Immunol 1989, 33:479-488.

Byars et al. "Adjuvant Formulation for use in Vaccines to Elicit Both Cell-Mediated and Humoral Immunity" Vaccine 1987, 5:223-228.

Martinon et al. "Efficacy of a 'One Shot' Schedule of a Mycoplasma Hyopneumoniae Bacterin (Hyoresp)" Proceedings of the 15th IPVS Congress, Birmingham, England, Jul. 5-9, 1998, p. 284.

Reynaud et al. "Clinical Field Trial With Mycoplasma Hyopneumoniae Bacterin (Hyoresp)" Proceedings of the 15th IPVS Congress, Birmingham, England, Jul. 5-9, 1998 p. 150.

Charlier et al. "Comparative Efficacy of Stellamune Mycoplasma and Hyoresp in Pigs Against an Experimental Challenge with Mycoplasma Hyopneumoniae" The 16th International Pig Veterinary Society Congress, Melbourne, Australia Sep. 17-20, 2000 p. 501.

Djordjevic et al. "Serum and mucosal antibody responses and protection in pigs vaccinated against mycoplasma hyopneumoniae with vaccines containing a denatured membrane antigen pool and adjuvant", Australian Veterinary Journal, vol. 75 No. 7, pp. 504-511, Jul. 1, 1997.

Chen et al. "Evaluation of immune response to recombinant potential protective antigens of mycoplasma hyopneumoniae delivered as cocktail DNA and/or recombinant protein vaccines in mice", Vaccine, vol. 26 No. 34, pp. 4372-4378, Aug. 12, 2008.

Drexler et al. "Efficacy of combined porcine reproductive and respiratory syndrome virus and mycoplasma hyopneumoniae vaccination in piglets", Veterinary Record, vol. 166 No. 3, pp. 70-74, Jan. 16, 2010.

(56) References Cited

OTHER PUBLICATIONS

Grau-Roma et al. "Recent advances in the epidemiology, diagnosis and control of diseases caused by porcine circovirus type 2", Veterinary Journal, vol. 187 No. 1, pp. 23-32, Jan. 1, 2011.
Okada et al. "Cytological and immunological changes in bronchoalveolar lavage fluid and histological observation of lung lesions in pigs immunized with mycoplasma hyopneumoniae inactivated vaccine prepared from broth culture supernate", Vaccine, vol. 18, No. 25, pp. 2825-2831, Jun. 1, 2000.
Okada M.et al. "Evaluation of mycoplasma hyopneumoniae inactivated vaccine in pigs under field conditions", J. Vet. Med. Science, vol. 61 No. 10, pp. 1131-1135, Jun. 25, 1999.
Genzow Marika et al. "Concurrent vaccination of piglets with Ingelvac ® PRRS MLV and with Ingelvac ® M. hyo", Tieraerztliche Umschau, vol. 61 No. 12, pp. 649-652, Dec. 1, 2006.
Xin-Gang et al. "Baculovirus as a PRRSV and PCV2 bivalent vaccine vector: Baculovirus virions displaying simultaneously GP5 glycoprotein of PRRSV and capsid protein of PCV2", Journal of Virological Methods, vol. 179 No. 2, pp. 359-366, Nov. 28, 2011.
Ross "Characteristics of a protective activity of mycoplasma hyopneumoniae vaccine" American Journal of Veterinary Research, vol. 45 No. 10, pp. 1899-1905, Oct. 1984.
Sheldrake et al. "Evaluation of an enzyme-linked immunosorbent assay for the detection of Mycoplasma hyopneumoniae antibody in porcine serum" Australian Veterinary Journal vol. 69, No. 10, Oct. 1992.
Fort Dodge Australia (2000) TechNote—Technical Update TF S04-00 (1) "Suvaxyn M. Hyo—How it works".
Zanh et al. (Journal of General Virology 2005; 86: 677-685).
Redgeld et al. (Nature Medicine 2002; 8 (7): 694-701).
Declaration of Gregory P. Nitzel From U.S. Appl. No. 13/850,318.
O'Dea, MA, Australia & New Zealand Standard Diagnostic Procedure, Jul. 2010 (http://www.agriculture.gov.au/SiteCollectionDocuments/animal/ahl/ANZSDP-Porcine-circovirus-infection.pdf), pp. 1-20.
Gillespie, J. et al., "Porcine Circovirus Type 2 and Porcine Circovirus-Associated Disease", J Vet Intern Med 2009; 23:1151-1163.
Allan, Gordon M. and Ellis, John A., "Porcine circoviruses: a review," J Vet Diagn Invest 12:3-14 (2000).
Freundt, E.A., "Culture Media for Classic Mycoplasmas," pp. 127-135 of Methods in Mycoplasmology, vol. I, (Editors Razin and Tully).
Kricka, L.J., "Interferences in Immunoassay—Still a Threat", Clinical Chemistry 46, No. 8, 2000, pp. 1037-1038.
Selby, Colin, "Interference in immunoassay," Ann Clin Biochem 1999; 36: pp. 704-721.
Straw, B; Zimmerman, J.; D'Allaire, S.; Taylor, D. (eds), Diseases of Swine, (Wiley Blackwell, 9th ed., 2006), Chapter 14.
Aphis info sheet (Jan. 2009), "PRRS Seroprevalence on U.S. Swine Operations," Veterinary Services; United States Department of Agriculture.
Bautista, Elida M. et al., "Seroprevalence of PRRS virus in the United States," Swine Health and Production—Nov. and Dec., 1993, 1: pp. 4-8.
Chen, Jia-Rong, et al., "Identification of the copper-zinc superoxide dismutase activity in Mycoplasma hyopneumoniae," Veterinary Microbiology 73 (2000) pp. 301-310.
Chen, Jia-Rong, et al., "Identification of a novel adhesin-like glycoprotein from Mycoplasma hyopneumoniae," Veterinary Microbiology 62 (1998) pp. 97-110.
Lam, K.M., "Serologic and immunologic studies on Mycoplasma hyopneumoniae pneumonia of swine," Iowa State University, Retrospective Theses and Dissertations. 4178. 1970.
Bordier, Clement, "Phase Separation of Integral Membrane Proteins in Triton X-114 Solution*," The Journal of Biological Chemistry, vol. 256. No. 4, Issue of Feb. 25, pp. 1604-1607,1981.
Porcine Respiratory Disease Complex—The Pig Site, Feb. 12, 2009, pp. 1-3. http://www.thepigsite.com/articles/2606/porcine-respiratory-disease.
Kaiser, Troy J. et al., "Mycoplasma Hyopneumoniae Efficacy and Field Safety Evaluation of a 3-Way Haemophilus Parasuis/Mycoplasma Hyopneumoniae Combination Bacterin" Allen D. Leman Swine Conference—Recent Research Reports, 31 (2008).
Quilitis, Michael Felipe E., "Serological response to PRRS vaccination using a mycoplasma bacterin (Mypravac® Suis) as diluents for a live attenuated PRRSV vaccine AMERVAC®PRRS", Porcine Reproductive and Respiratory Syndrome (PRRS) Vaccination—Proceedings of the 21st IPVS Congress, Vancouver, Canada—Jul. 18-21, 2010, p. 235:541.
Hutchinson, Doug, "New Advancements in the Control of Erysipelas and Mycoplasma Pneumonia," M+Rhusigen™, Interview. (2005).
Responsible Use of Medicines in Agriculture Alliance (RUMA) Guidelines, "Responsible use of vaccines and vaccination in pig production," Nov. 2006, pp. 1-24.
Amersham Biosciences Antibody Purification Handbook (2002).
Annual Report from Meiji Seika Kaisha, Ltd. published in 2003.
Beigel et al. (2018), "Safety and tolerability of a novel, polyclonal human anti-MERS coronavirus antibody produced from transchromosomic cattle: a phase 1 randomised, double-blind, single-dose-escalation study," Lancet Infectious Disease 18:410-18 and Appendix.
Committee for Human Medicinal Products (CHMP) notes for guidance of the clinical evaluation of vaccines (2005).
Eichmeyer, M. et al., "Efficacy of Ingelvac® PRRS MLV when rehydrated with a combination of Ingelvac MycoFLEX® and Ingelvac CircoFLEX®," 2010, Allen D. Leman Swine Conference.
Haiwick, G. et al., "Trivalent vaccine mixture protects against simultaneous challenge with *M. hyopneumoniae*, PCV2, and PRRS virus," 2010, Allen D. Leman Swine Conference.
Hopfe et al. (2004) "P80, the HinT interacting membrane protein, is a secreted antigen of *Mycoplasma hominis*," BMC Microbiology, 4:46-56.
Ingelvac CircoFLEX-MycoFLEX Material Safety Data Sheet, Jun. 23, 2008.
Lefevre et al., "Immune Responses in Pigs Vaccinated with Adjuvanted and Non-Adjuvanted A(H1N1)pdm/09 Influenza Vaccines Used in Human Immunization Programmes," PLoS ONE, Mar. 2012, vol. 7, Issue 3, e32400 (Published: Mar. 9, 2012, available at https://doi.org/10.1371/journal.pone.0032400).
Lindmark et al., "Binding of Immunoglobulins to Protein A and Immunoglobulin Levels in Mammalian Sera," Journal of Immunological Methods 62: 1-13 (1983).
Liu et al. (2010) "Recovery and purification process development for monoclonal antibody production," MAbs, 2:480-499.
Mycobuster® Product Sheet in Japanese with English language translation (Revision Nov. 2017).
Mycobuster AR Plus® Product Sheet in Japanese with English language translation (Revision Jun. 2017).
Saleh et al. (2001), "Identification of putative exported/secreted proteins in prokaryotic proteomes," Gene, 269:195-204.
Steel et al. (2003) "Efficient and Specific Removal of Albumin from Human Serum Samples*," Molecular and Cellular Proteomics, 2:262-270.
Rice et al., "G86-797 Causes of Vaccination-Immunization Failures in Livestock" (1986). Historical Materials from University of Nebraska-Lincoln Extension. 229. https://digitalcommons.unl.edu/extensionhist/229.
US-FDA Guidance of Industry for the Evaluation of combination vaccines for preventable diseases: production, testing and clinical studies. (1997).
Wise and Kim, "Major Membrane Surface Proteins of Mycoplasma *hyopneumoniae* Selectively Modified by Covalently Bound Lipid," Journal of Bacteriology 169:5546-5555 (1987).
Zhang et al., "Production of recombinant protein G through high-density fermentation of engineered bacteria as well as purification," Molecular Medicine Reports 12: 3132-3138 (2015).
Zoetis Technical update, Oct. 2013.

\* cited by examiner

| Contrast | Mitigated Fraction | 95% confidence interval |
|---|---|---|
| T01 vs T02 | 41.2 | -5.9 to 76.5 |
| T01 vs T03 | 64.7 | 29.4 to 100 |
| T01 vs T04 | 76.5 | 41.2 to 100 |
| T01 vs T05 | 73.3 | 33.3 to 100 |
| T01 vs T06 | 62.5 | 25 to 100 |
| T01 vs T07 | 87.5 | 62.5 to 100 |
| T01 vs T08 | 88.2 | 64.7 to 100 |

Figure 10

| Preliminary Viricidal Activity | Difference from Water | | | |
| --- | --- | --- | --- | --- |
| | 100% rehyd. Lyophilized Titer | 90/10 Liq. (DMEM) 90/10 | 90/10 Liq. (Ultra) 90/10 | Avg Viricidal Activity |
| 20% SLCD | 0.8 | 0.7 | 2.0 | 1.3 |
| 0.2% Carbopol | 0.3 | -0.3 | 0.2 | -0.1 |
| 10% SP-Oil | 0.2 | 0.0 | 0.0 | 0.0 |
| 10% SP-Oil/0.2% Carbopol | 0.3 | -0.2 | 0.0 | -0.1 |
| 20% SLCD/10% SP-Oil | 1.0 | 0.3 | 0.7 | 0.5 |
| 20% SLCD/10% SP-Oil/0.2% Carbopol | 0.2 | 0.0 | 0.5 | 0.3 |
| 5% Amphigen (from 40% stock) | 1.0 | 0.7 | 1.5 | 1.1 |
| 2.5% Amphigen (from 40% stock) | NA | -0.2 | NA | -0.2 |
| 5% Amphigen (from 20% stock) | NA | 0.8 | NA | 0.8 |
| 2.5% Amphigen (from 20% stock) | NA | 0.2 | NA | 0.2 |
| 5% Amphigen (from 40% stock) | NA | 1.3 | NA | 1.3 |
| 2.5% Amphigen (from 40% stock) | NA | 0.8 | NA | 0.8 |
| | Indicates potential viricidal activity | | | |

SEQUENCE LISTING

```
<160> NUMBER OF SEQ ID NOS: 18

<210> SEQ ID NO 1
<211> LENGTH: 1260
<212> TYPE: DNA
<213> ORGANISM: Mycoplasma hyopneumoniae

<400> SEQUENCE: 1
atgaaaaaaa tgcttagaaa aaaattcttg tattcatcag ctatttatgc aacttcgctt      60
gcatcaatta ttgcatttgt tgcagcaggt tgtggacaga cagaatcagg ttcgacttct     120
gattctaaac cacaagccga gacgctaaaa cataaagtaa gtaatgattc tattcgaata     180
gcactaaccg atccggataa tcctcgatga attagtgctc aaaaagatat tatttcttat     240
gttgatgaaa cagaggcagc aacttcaaca attacaaaaa accaggatgc acagaataac     300
tgactcactc agcaagctaa tttaagccca gcaccaaaag gatttattat tgccctgaa      360
```

-continued

```
aatggaagtg gagttggaac tgctgttaat acaattgctg ataaaggaat tccgattgtt      420
gcctatgatc gactaattac tggatctgat aaatatgatt ggtatgtttc ttttgataat      480
gaaaaagttg gcgaattaca aggtctttca cttgcagcgg gtctattagg aaaagaagat      540
ggtgcttttg attcaattga tcaaatgaat gaatatctaa aatcacatat gccccaagag      600
acaatttctt tttatacaat cgcgggttcc caagatgata taactccca atattttat       660
aatggtgcaa tgaaagtact aaagaatta atgaaaaatt cgggaaataa gataattgat      720
ttatctcctg aaggcgaaaa tgctgtttat gtcccaggat gaaattatgg aactgccggt      780
caaagaatcc aatcttttct aacaattaac aaagatccag caggtggtaa taaaatcaaa      840
gctgttggtt caaaaccagc ttctattttc aaaggatttc ttgccccaaa tgatggaatg      900
gccgarcaag caatcaccaa attaaaactt gaaggatttg atacccaaaa atctttgta      960
actggtcaag attataatga taaagccaaa acttttatca aagacggcga tcaaaatatg     1020
acaatttata aacctgataa agttttagga aaagttgctg ttgaagttct tcgggttta      1080
attgcaaaga aaaataaagc atccagatca gaagtcgaaa acgaactaaa agcaaaacta     1140
ccaaatattt catttaaata tgataatcaa acatataaag tgcaaggtaa aaatattaat     1200
acaatttag taagtccagt aattgttaca aaagctaatg ttgataatcc tgatgcctaa     1260
```

<210> SEQ ID NO 2
<211> LENGTH: 419
<212> TYPE: PRT
<213> ORGANISM: Mycoplasma hyopneumoniae

<400> SEQUENCE: 2

```
Met Lys Lys Met Leu Arg Lys Lys Phe Leu Tyr Ser Ser Ala Ile Tyr
  1               5                  10                  15

Ala Thr Ser Leu Ala Ser Ile Ile Ala Phe Val Ala Ala Gly Cys Gly
             20                  25                  30

Gln Thr Glu Ser Gly Ser Thr Ser Asp Ser Lys Pro Gln Ala Glu Thr
         35                  40                  45

Leu Lys His Lys Val Ser Asn Asp Ser Ile Arg Ile Ala Leu Thr Asp
     50                  55                  60

Pro Asp Asn Pro Arg Trp Ile Ser Ala Gln Lys Asp Ile Ile Ser Tyr
 65                  70                  75                  80

Val Asp Glu Thr Glu Ala Ala Thr Ser Thr Ile Thr Lys Asn Gln Asp
                 85                  90                  95

Ala Gln Asn Asn Trp Leu Thr Gln Gln Ala Asn Leu Ser Pro Ala Pro
            100                 105                 110

Lys Gly Phe Ile Ile Ala Pro Glu Asn Gly Ser Gly Val Gly Thr Ala
        115                 120                 125

Val Asn Thr Ile Ala Asp Lys Gly Ile Pro Ile Val Ala Tyr Asp Arg
    130                 135                 140

Leu Ile Thr Gly Ser Asp Lys Tyr Asp Trp Tyr Val Ser Phe Asp Asn
145                 150                 155                 160

Glu Lys Val Gly Glu Leu Gln Gly Leu Ser Leu Ala Ala Gly Leu Leu
                165                 170                 175

Gly Lys Glu Asp Gly Ala Phe Asp Ser Ile Asp Gln Met Asn Glu Tyr
            180                 185                 190

Leu Lys Ser His Met Pro Gln Glu Thr Ile Ser Phe Tyr Thr Ile Ala
        195                 200                 205

Gly Ser Gln Asp Asp Asn Asn Ser Gln Tyr Phe Tyr Asn Gly Ala Met
    210                 215                 220
```

Lys Val Leu Lys Glu Leu Met Lys Asn Ser Gly Asn Lys Ile Ile Asp
225 230 235 240

Leu Ser Pro Glu Gly Glu Asn Ala Val Tyr Val Pro Gly Trp Asn Tyr
245 250 255

Gly Thr Ala Gly Gln Arg Ile Gln Ser Phe Leu Thr Ile Asn Lys Asp
260 265 270

Pro Ala Gly Gly Asn Lys Ile Lys Ala Val Gly Ser Lys Pro Ala Ser
275 280 285

Ile Phe Lys Gly Phe Leu Ala Pro Asn Asp Gly Met Ala Glu Gln Ala
290 295 300

Ile Thr Lys Leu Lys Leu Glu Gly Phe Asp Thr Gln Lys Ile Phe Val
305 310 315 320

Thr Gly Gln Asp Tyr Asn Asp Lys Ala Lys Thr Phe Ile Lys Asp Gly
325 330 335

Asp Gln Asn Met Thr Ile Tyr Lys Pro Asp Lys Val Leu Gly Lys Val
340 345 350

Ala Val Glu Val Leu Arg Val Leu Ile Ala Lys Lys Asn Lys Ala Ser
355 360 365

Arg Ser Glu Val Glu Asn Glu Leu Lys Ala Lys Leu Pro Asn Ile Ser
370 375 380

Phe Lys Tyr Asp Asn Gln Thr Tyr Lys Val Gln Gly Lys Asn Ile Asn
385 390 395 400

Thr Ile Leu Val Ser Pro Val Ile Val Thr Lys Ala Asn Val Asp Asn
405 410 415

Pro Asp Ala

<210> SEQ ID NO 3
<211> LENGTH: 3324
<212> TYPE: DNA
<213> ORGANISM: Mycoplasma hyopneumoniae

<400> SEQUENCE: 3
atgagtaaaa aatcaaaaac atttaaaatt ggtttgactg ccggaattgt tggtcttgga 60
gtttttggtc taactgtcgg acttagcagc ttggcaaaat acagatcaga aagtccacga 120
aagattgcaa atgattttgc cgcaaaagtt tcaacattag cttttagtcc ttatgctttt 180
gagactgatt ctgattataa aatagtcaaa aggtgactag ttgattctaa taacaatatt 240
agaaataaag aaaaagttat tgattccttt tcctttttta ctaaaaacgg tgatcagtta 300
gaaaaaatta attttcaaga tcctgaatat accaaggcga agataacttt tgagattctt 360
gaaattatcc ctgatgatgt caatcaaaat tttaaggtaa aatttcaggc attacaaaaa 420
cttcataatg gtgatattgc caaatctgat atttatgagc aaacagttgc ttttgccaaa 480
cagtcaaatc ttttagttgc cgaatttaat ttttcgctta aaaaaattac cgaaaaatta 540
aatcaacaaa ttgaaaattt atcaacaaaa attacaaatt ttgctgatga aaaaacaagc 600
agccaaaaag atccctcaac tctaagagct attgacttcc aatacgattt aaatacagcg 660
cgaaatcctg aggatttaga tataaagctt gctaattatt ttccagtact taaaaattta 720
ataaacagac taaataatgc tcctgagaat aaattaccta ataatttggg taatattttt 780
gaatttagct ttgcaaaaga tagttcaact aatcaatatg taagtatcca gaaccaaatt 840
ccttcgctgt ttttaaaagc agatcttagt caaagtgccc gtgaaatttt agctagccca 900
gatgaagttc agccagttat taacatttta agattaatga aaaaagataa ttcttcttat 960

-continued

```
tttctaaatt ttgaggattt tgttaataat ttaacactga aaaatatgca aaagaagat    1020 ttaaatgcaa agggtcaaaa tctttctgcc tatgaatttc tagcagatat aaatctgga    1080 tttttccctg gagacaagag atccagtcat accaaggcag aaattagtaa tcttttaaat   1140
aaaaaagaaa atatttatga ctttggtaaa tacaatggaa aattcaacga ccgtcttaac   1200
tcgccaaatt tagaatatag cctagatgca gcaagcgcaa gtcttgataa aaaagataaa   1260
tcaatagttt taattcccta ccgccttgaa attaaagata aatttttttgc cgatgattta   1320 tatccagata caaaagataa tattctcgta aaagaaggga ttcttaaatt aactggattt    1380
aaaaaaggct caaaaattga tctccctaat atcaatcagc aaattttaa aaccgaatat    1440 ttaccatttt ttgaaaaagg taagaagaa caagcaaaat tagactatgg taatatctta    1500
aatccatata atactcaact tgccaaagtt gaagttgaag ctcttttaa agggaataaa    1560 aaccaagaaa tctatcaagc acttgatgga aattatgcct atgaattcgg ggcctttaaa   1620
tccgtgctta attcctgaac aggaaaaatt cagcatcctg aaaaagctga tatccaaaga   1680
tttacaagac atttagaaca agttaaaatt ggttctaatt cagttttaaa tcaaccacaa   1740
acaacaaaag aacaagtaat ttcaagtctt aaaagtaata acttttttaa aaatggacat   1800
caagttgcaa gttatttcca ggatttactc accaaggaca aattaacaat tttagagact   1860
ctttatgatc tagcaaaaaa atggggacta gaaactaaca gagcacaatt cccaaaaggg   1920
gttttccaat atacaaaaga tattttttgca gaagcagata aattaaaatt tttggaattg   1980
aagaaaaagg atccttacaa tcagataaaa gaaattcacc aactttcctt taatattta   2040 gcccgtaacg atgtaataaa atctgatgga ttttacggag ttttattatt gccccaaagt   2100
gtaaaaactg aattagaagg caaaaatgag gcgcaaattt ttgaagcgct taaaaagtat   2160
tctttaattg agaactcggc ttttaaaact actattttag ataaaaattt acttgaaggg   2220
actgatttta aaaccttcgg tgattttta aaagcatttt tccttaaagc agcccaattt   2280
aataattttg ctccttgagc aaaattagac gataatcttc agtattcatt tgaagctatc   2340
aaaaaagggg aaactacaaa agaaggtaaa agagaagaag tagataaaaa agttaaggaa   2400
ttggataata aaataaaagg tatattgcct cagcccccag cagcaaaacc agaagcagca   2460
aaaccagtag cggctaaacc agaaacaaca aaaccagtag cagctaaacc tgaagcagct   2520
aaacctgaag cagcaaaacc agtagcggct aaaccagaag cagcaaaacc agtagcggct   2580
aaaccagaag cagcaaaacc agtagcggct aaaccagaag cagcaaaacc agtagcggct   2640
aaaccagaag cagcaaaacc agttgctact aatactggct tttcacttac aaataaacca   2700
aaagaagact atttcccaat ggcttttagt tataaattag aatatactga cgaaaataaa   2760
ttaagcctaa aaacaccgga aattaatgta tttttagaac tagttcatca aagcgagtat   2820
gaagaacaag aaataataaa ggaactagat aaaactgttt taaatcttca atatcaattc   2880
caggaagtca agtaactag tgaccaatat cagaaactta gccacccaat gatgaccgaa   2940
ggatcttcaa atcaaggtaa aaaaagcgaa ggaactccta ccaaggtaa aaaagcagaa   3000 ggcgcgccta ccaaggtaa aaagccgaa ggaactccta ccaagggaa aaaagcagag    3060 ggagcaccta gtcaacaaag cccaactacc gaattaacta attaccttcc tgacttaggt   3120
aaaaaaattg acgaaatcat taaaaaacaa ggtaaaaatt gaaaaacaga ggttgaacta   3180
atcgaggata atatcgctgg agatgctaaa ttgctatact ttatcctaag ggatgattca   3240
aaatccggtg atcctaaaaa atcaagtcta aaagttaaaa taacagtaaa acaaagtaat   3300
aataatcagg aaccagaatc taaa                                          3324
```

<210> SEQ ID NO 4
<211> LENGTH: 1108
<212> TYPE: PRT
<213> ORGANISM: Mycoplasma hyopneumoniae

<400> SEQUENCE: 4

Met Ser Lys Lys Ser Lys Thr Phe Lys Ile Gly Leu Thr Ala Gly Ile
1               5                   10                  15

Val Gly Leu Gly Val Phe Gly Leu Thr Val Gly Leu Ser Ser Leu Ala
            20                  25                  30

Lys Tyr Arg Ser Glu Ser Pro Arg Lys Ile Ala Asn Asp Phe Ala Ala
        35                  40                  45

Lys Val Ser Thr Leu Ala Phe Ser Pro Tyr Ala Phe Glu Thr Asp Ser
    50                  55                  60

Asp Tyr Lys Ile Val Lys Arg Trp Leu Val Asp Ser Asn Asn Asn Ile
65                  70                  75                  80

Arg Asn Lys Glu Lys Val Ile Asp Ser Phe Ser Phe Thr Lys Asn
                85                  90                  95

Gly Asp Gln Leu Glu Lys Ile Asn Phe Gln Asp Pro Glu Tyr Thr Lys
            100                 105                 110

Ala Lys Ile Thr Phe Glu Ile Leu Glu Ile Ile Pro Asp Asp Val Asn
        115                 120                 125

Gln Asn Phe Lys Val Lys Phe Gln Ala Leu Gln Lys Leu His Asn Gly
    130                 135                 140

Asp Ile Ala Lys Ser Asp Ile Tyr Glu Gln Thr Val Ala Phe Ala Lys
145                 150                 155                 160

Gln Ser Asn Leu Leu Val Ala Glu Phe Asn Phe Ser Leu Lys Lys Ile
                165                 170                 175

Thr Glu Lys Leu Asn Gln Gln Ile Glu Asn Leu Ser Thr Lys Ile Thr
            180                 185                 190

Asn Phe Ala Asp Glu Lys Thr Ser Ser Gln Lys Asp Pro Ser Thr Leu
        195                 200                 205

Arg Ala Ile Asp Phe Gln Tyr Asp Leu Asn Thr Ala Arg Asn Pro Glu
    210                 215                 220

Asp Leu Asp Ile Lys Leu Ala Asn Tyr Phe Pro Val Leu Lys Asn Leu
225                 230                 235                 240

Ile Asn Arg Leu Asn Asn Ala Pro Glu Asn Lys Leu Pro Asn Asn Leu
                245                 250                 255

Gly Asn Ile Phe Glu Phe Ser Phe Ala Lys Asp Ser Thr Asn Gln
            260                 265                 270

Tyr Val Ser Ile Gln Asn Gln Ile Pro Ser Leu Phe Leu Lys Ala Asp
        275                 280                 285

Leu Ser Gln Ser Ala Arg Glu Ile Leu Ala Ser Pro Asp Glu Val Gln
    290                 295                 300

Pro Val Ile Asn Ile Leu Arg Leu Met Lys Lys Asp Asn Ser Ser Tyr
305                 310                 315                 320

Phe Leu Asn Phe Glu Asp Phe Val Asn Asn Leu Thr Leu Lys Asn Met
                325                 330                 335

Gln Lys Glu Asp Leu Asn Ala Lys Gly Gln Asn Leu Ser Ala Tyr Glu
            340                 345                 350

Phe Leu Ala Asp Ile Lys Ser Gly Phe Phe Pro Gly Asp Lys Arg Ser
        355                 360                 365

Ser His Thr Lys Ala Glu Ile Ser Asn Leu Leu Asn Lys Lys Glu Asn

```
                370                 375                 380
Ile Tyr Asp Phe Gly Lys Tyr Asn Gly Lys Phe Asn Asp Arg Leu Asn
385                 390                 395                 400

Ser Pro Asn Leu Glu Tyr Ser Leu Asp Ala Ser Ala Ser Leu Asp
                405                 410                 415

Lys Lys Asp Lys Ser Ile Val Leu Ile Pro Tyr Arg Leu Glu Ile Lys
                420                 425                 430

Asp Lys Phe Phe Ala Asp Asp Leu Tyr Pro Asp Thr Lys Asp Asn Ile
                435                 440                 445

Leu Val Lys Glu Gly Ile Leu Lys Leu Thr Gly Phe Lys Lys Gly Ser
                450                 455                 460

Lys Ile Asp Leu Pro Asn Ile Asn Gln Gln Ile Phe Lys Thr Glu Tyr
465                 470                 475                 480

Leu Pro Phe Phe Glu Lys Gly Lys Glu Gln Ala Lys Leu Asp Tyr
                485                 490                 495

Gly Asn Ile Leu Asn Pro Tyr Asn Thr Gln Leu Ala Lys Val Glu Val
                500                 505                 510

Glu Ala Leu Phe Lys Gly Asn Lys Asn Gln Glu Ile Tyr Gln Ala Leu
                515                 520                 525

Asp Gly Asn Tyr Ala Tyr Glu Phe Gly Ala Phe Lys Ser Val Leu Asn
                530                 535                 540

Ser Trp Thr Gly Lys Ile Gln His Pro Glu Lys Ala Asp Ile Gln Arg
545                 550                 555                 560

Phe Thr Arg His Leu Glu Gln Val Lys Ile Gly Ser Asn Ser Val Leu
                565                 570                 575

Asn Gln Pro Gln Thr Thr Lys Glu Gln Val Ile Ser Ser Leu Lys Ser
                580                 585                 590

Asn Asn Phe Phe Lys Asn Gly His Gln Val Ala Ser Tyr Phe Gln Asp
                595                 600                 605

Leu Leu Thr Lys Asp Lys Leu Thr Ile Leu Glu Thr Leu Tyr Asp Leu
                610                 615                 620

Ala Lys Lys Trp Gly Leu Glu Thr Asn Arg Ala Gln Phe Pro Lys Gly
625                 630                 635                 640

Val Phe Gln Tyr Thr Lys Asp Ile Phe Ala Glu Ala Asp Lys Leu Lys
                645                 650                 655

Phe Leu Glu Leu Lys Lys Asp Pro Tyr Asn Gln Ile Lys Glu Ile
                660                 665                 670

His Gln Leu Ser Phe Asn Ile Leu Ala Arg Asn Asp Val Ile Lys Ser
                675                 680                 685

Asp Gly Phe Tyr Gly Val Leu Leu Pro Gln Ser Val Lys Thr Glu
                690                 695                 700

Leu Glu Gly Lys Asn Glu Ala Gln Ile Phe Glu Ala Leu Lys Lys Tyr
705                 710                 715                 720

Ser Leu Ile Glu Asn Ser Ala Phe Lys Thr Thr Ile Leu Asp Lys Asn
                725                 730                 735

Leu Leu Glu Gly Thr Asp Phe Lys Thr Phe Gly Asp Phe Leu Lys Ala
                740                 745                 750

Phe Phe Leu Lys Ala Ala Gln Phe Asn Asn Phe Ala Pro Trp Ala Lys
                755                 760                 765

Leu Asp Asp Asn Leu Gln Tyr Ser Phe Glu Ala Ile Lys Lys Gly Glu
                770                 775                 780

Thr Thr Lys Glu Gly Lys Arg Glu Glu Val Asp Lys Lys Val Lys Glu
785                 790                 795                 800
```

-continued

```
Leu Asp Asn Lys Ile Lys Gly Ile Leu Pro Gln Pro Pro Ala Ala Lys
            805                 810                 815
Pro Glu Ala Ala Lys Pro Val Ala Ala Lys Pro Glu Thr Thr Lys Pro
        820                 825                 830
Val Ala Ala Lys Pro Glu Ala Ala Lys Pro Glu Ala Ala Lys Pro Val
    835                 840                 845
Ala Ala Lys Pro Glu Ala Ala Lys Pro Val Ala Ala Lys Pro Glu Ala
850                 855                 860
Ala Lys Pro Val Ala Lys Pro Glu Ala Lys Pro Val Ala Ala
865                 870                 875                 880
Lys Pro Glu Ala Ala Lys Pro Val Ala Thr Asn Thr Gly Phe Ser Leu
                885                 890                 895
Thr Asn Lys Pro Lys Glu Asp Tyr Phe Pro Met Ala Phe Ser Tyr Lys
            900                 905                 910
Leu Glu Tyr Thr Asp Glu Asn Lys Leu Ser Leu Lys Thr Pro Glu Ile
        915                 920                 925
Asn Val Phe Leu Glu Leu Val His Gln Ser Glu Tyr Glu Glu Gln Glu
    930                 935                 940
Ile Ile Lys Glu Leu Asp Lys Thr Val Leu Asn Leu Gln Tyr Gln Phe
945                 950                 955                 960
Gln Glu Val Lys Val Thr Ser Asp Gln Tyr Gln Lys Leu Ser His Pro
                965                 970                 975
Met Met Thr Glu Gly Ser Ser Asn Gln Gly Lys Lys Ser Glu Gly Thr
            980                 985                 990
Pro Asn Gln Gly Lys Lys Ala Glu Gly Ala Pro Asn Gln Gly Lys Lys
        995                 1000                1005
Ala Glu Gly Thr Pro Asn Gln Gly Lys Lys Ala Glu Gly Ala Pro
    1010                1015                1020
Ser Gln Gln Ser Pro Thr Thr Glu Leu Thr Asn Tyr Leu Pro Asp
    1025                1030                1035
Leu Gly Lys Lys Ile Asp Glu Ile Ile Lys Lys Gln Gly Lys Asn
    1040                1045                1050
Trp Lys Thr Glu Val Glu Leu Ile Glu Asp Asn Ile Ala Gly Asp
    1055                1060                1065
Ala Lys Leu Leu Tyr Phe Ile Leu Arg Asp Asp Ser Lys Ser Gly
    1070                1075                1080
Asp Pro Lys Lys Ser Ser Leu Lys Val Lys Ile Thr Val Lys Gln
    1085                1090                1095
Ser Asn Asn Asn Gln Glu Pro Glu Ser Lys
    1100                1105

<210> SEQ ID NO 5
<211> LENGTH: 1773
<212> TYPE: DNA
<213> ORGANISM: Porcine circovirus

<400> SEQUENCE: 5
ggtacctccg tggattgttc tccagcagtc ttccaaaatt gcaaagtagt aatcctccga      60
tagagagctt ctacagctgg acagcagtt gaggagtacc attcctgggg ggcctgattg     120
ctggtaatca aaatactgcg ggccaaaaaa ggaacagtac cccctttagt ctctacagtc     180
aatggatacc ggtcacacag tctcagtaga tcatcccaag gtaaccagcc ataaaaatca     240
tccaaaacaa caacttcttc tccatgatat ccatcccacc acttatttct actaggcttc     300
```

```
cagtaggtgt ccctaggctc agcaaaatta cgggcccact ggctcttccc acaaccgggc    360
gggcccacta tgacgtgtac agctgtcttc caatcacgct gctgcatctt cccgctcact    420
ttcaaaagtt cagccagccc gcggaaattt ctcacatacg ttacaggaaa ctgctcggct    480
acagtcacca aagaccccgt ctccaaaagg gtactcacag cagtagacag gtcgctgcgc    540
ttcccctggt tccgcggagc tccacactcg ataagtatgt ggccttcttt actgcagtat    600
tctttattct gctggtcggt tcctttcgct ttctcgatgt ggcagcgggc accaaaatac    660
cacttcacct tgttaaaagt ctgcttctta gcaaaattcg caaaccctg gaggtgagga    720
gttctaccct cttccaaacc ttcctcgcca caaacaaaat aatcaaaaag ggagattgga    780
agctcccgta ttttgttttt ctcctcctcg aaggattat taagggtgaa cacccacctc    840
ttatggggtt gcgggccgct tttcttgctt ggcattttca ctgacgctgc cgaggtgctg    900
ccgctgccga agtgcgctgg taatactaca gcagcgcact ctttcactt ttataggatg    960
acgtatccaa ggaggcgtta ccgcagaaga agacaccgcc cccgcagcca tcttggccag   1020
atcctccgcc gccgcccctg gctcgtccac ccccgccacc gctaccgttg gagaaggaaa   1080
aatggcatct tcaacacccg cctctcccgc accttcggat atactgtcaa ggctaccaca   1140
gtcagaacgc cctcctgggc ggtggacatg atgagattta atattgacga ctttgttccc   1200
ccggaggggg ggaccaacaa aatctctata ccctttgaat actacagaat aagaaaggtt   1260
aaggttgaat tctggccctg ctcccccatc acccagggtg ataggggagt gggctccact   1320
gctgttattc tagatgataa ctttgtaaca aaggccacag ccctaaccta tgacccatat   1380
gtaaactact cctcccgcca tacaatcccc caacccttct cctaccactc ccgttacttc   1440
acacccaaac ctgttcttga ctccaccatt gattacttcc aaccaaataa caaaaggaat   1500
cagctttgga tgaggctaca aacctctaga aatgtggacc acgtaggcct cggcactgcg   1560
ttcgaaaaca gtatatacga ccaggactac aatatccgtg taaccatgta tgtacaattc   1620
agagaattta tcttaaaga ccccccactt aaacccaaa tgaataaaaa taaaaaccat   1680
tacgatgtga taacaaaaaa gactcagtaa tttattttat atgggaaaag ggcacagggt   1740
gggtccactg cttcaaatcg gccttcgggt acc                                1773
```

<210> SEQ ID NO 6  
<211> LENGTH: 702  
<212> TYPE: DNA  
<213> ORGANISM: Porcine circovirus

<400> SEQUENCE: 6

```
atgacgtatc caaggaggcg ttaccgcaga agaagacacc gcccccgcag ccatcttggc     60
cagatcctcc gccgccgccc ctggctcgtc caccccgcc accgctaccg ttggagaagg    120
aaaaatggca tcttcaacac ccgcctctcc cgcaccttcg atatactgt caaggctacc    180
acagtcagaa cgccctcctg gcggtggac atgatgagat taatattga cgactttgtt    240
cccccgggag ggggaccaa caaatctct ataccctttg aatactacag aataagaaag    300
gttaaggttg aattctggcc ctgctccccc atcacccagg gtgataggg agtgggctcc    360
actgctgtta ttctagatga taactttgta acaaaggcca cagccctaac ctatgaccca    420
tatgtaaaact actcctcccg ccatacaatc cccaacccct ctcctacca ctcccgttac    480
ttcacaccca aacctgttct tgactccacc attgattact ccaaccaaa taacaaaagg    540
aatcagcttt ggatgaggct acaaacctct agaaatgtgg accacgtagg cctcggcact    600
gcgttcgaaa acagtatata cgaccaggac tacaatatcc gtgtaaccat gtatgtacaa    660
```
ttcagagaat ttaatcttaa agaccccca cttaaaccct aa    702

<210> SEQ ID NO 7
<211> LENGTH: 233
<212> TYPE: PRT
<213> ORGANISM: Porcine circovirus

<400> SEQUENCE: 7

Met Thr Tyr Pro Arg Arg Tyr Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230

<210> SEQ ID NO 8
<211> LENGTH: 1767
<212> TYPE: DNA
<213> ORGANISM: Porcine circovirus

<400> SEQUENCE: 8
ggtacctccg tggattgttc tccagcagtc ttccaaaatt gcaaagtagt aatcctccga    60
tagagagctt ctacagctgg acagcagtt gaggagtacc attcctgggg ggcctgattg    120
ctggtaatca aaatactgcg ggccaaaaaa ggaacagtac cccctttagt ctctacagtc    180
aatggatacc ggtcacacag tctcagtaga tcatcccaag gtaaccagcc ataaaaatca    240
tccaaaacaa caacttcttc tccatgatat ccatcccacc acttatttct actaggcttc    300
cagtaggtgt cgctaggctc agcaaaatta cgggcccact ggctcttccc acaaccgggc    360
gggcccacta tgacgtgtac agctgtcttc aatcacgct gctgcatctt cccgctcact    420
ttcaaaagtt cagccagccc gcggaaattt ctcacatacg ttacagggaa ctgctcggct    480

```
acagtcacca aagacccegt ctccaaaagg gtactcacag cagtagacag gtcgctgcgc    540
ttcccctggt tccgcggagc tccacactcg ataagtatgt ggccttcttt actgcagtat    600
tctttattct gctggtcggt tcctttcgct ttctcgatgt ggcagcgggc accaaaatac    660
cacttcacct tgttaaaagt ctgcttctta gcaaaattcg caaaccctg gaggtgagga    720
gttctaccct cttccaaacc ttcctctccg caaacaaaat aatcaaaaag ggagattgga    780
agctcccgta ttttgttttt ctcctcctcg aaggattat aagggtgaa cacccacctc     840
ttatggggtt gcgggccgct tttcctgctt ggcattttca ctgacgctgc cgaggtgctg    900
ccgctgccga gtgcgctgg taatactaca gcagcgcact tctttcactt ttataggatg     960
acgtatccaa ggaggcgtta ccgcagaaga agacaccgcc cccgcagcca tcttggccag   1020
atcctccgcc gccgcccctg gctcgtccac ccccgccacc gctaccgttg agaaggaaa    1080
aatggcatct tcaacacccg cctctcccgc accttcggat atactgtcaa ggctaccaca   1140
gtcagaacgc cctcctgggc ggtggacatg atgagattta atattgacga ctttgttccc   1200
ccgggagggg ggaccaacaa aatctctata ccctttgaat actacagaat aagaaaggtt   1260
aaggttgaat tctggccctg ctccccccatc acccagggtg ataggggagt gggctccact   1320
gctgttattc tagatgataa cttttgtaaca aaggccacag ccctaaccta tgacccatat   1380
gtaaactact cctcccgcca tacaatcgcc caaccttct cctaccactc ccgttacttc     1440
acacccaaac ctgttcttga ctccaccatt gattacttcc aaccaaataa caaaaggaat   1500
cagctttgga tgaggctaca aacctctaga aatgtggacc acgtaggcct cggcactgcg   1560
ttcgaaaaca gtatatacga ccaggactac aatatccgtg taaccatgta tgtacaattc   1620
agagaattta atcttaaaga ccccccactt aaaccctaaa tgaataaaaa taaaaaccat   1680
tacgatgtga taacaaaaaa gactcagtaa tttatttat atgggaaaag ggcacagggt   1740
gggtccactg cttcaaatcg gccttcg                                       1767
```

<210> SEQ ID NO 9
<211> LENGTH: 702
<212> TYPE: DNA
<213> ORGANISM: Porcine circovirus

<400> SEQUENCE: 9

```
atgacgtatc caaggaggcg ttaccgcaga agaagacacc gcccccgcag ccatcttggc     60
cagatcctcc gccgccgccc ctggctcgtc caccccgcc accgctaccg ttggagaagg    120
aaaaatggca tcttcaacac ccgcctctcc cgcaccttcg gatatactgt caaggctacc    180
acagtcagaa cgccctcctg gcggtggac atgatgagat ttaatattga cgactttgtt     240
ccccccgggag gggggaccaa caaaatctct ataccctttg aatactacag aataagaaag   300
gttaaggttg aattctggcc ctgctccccc atcacccagg gtgataggg agtgggctcc    360
actgctgtta ttctagatga taactttgta acaaaggcca cagccctaac ctatgaccca    420
tatgtaaaact actcctcccg ccatacaatc gcccaaccct tctcctacca ctcccgttac    480
ttcacaccca aacctgttct tgactccacc attgattact ccaaccaaa taacaaaagg    540
aatcagcttt ggatgaggct acaaacctct agaaatgtgg accacgtagg cctcggcact    600
gcgttcgaaa acagtatata cgaccaggac tacaatatcc gtgtaaccat gtatgtacaa    660
ttcagagaat ttaatcttaa agaccccca cttaaaccct aa                        702
```

<210> SEQ ID NO 10

<211> LENGTH: 233
<212> TYPE: PRT
<213> ORGANISM: Porcine circovirus

<400> SEQUENCE: 10

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Ala Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Met Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

<210> SEQ ID NO 11
<211> LENGTH: 233
<212> TYPE: PRT
<213> ORGANISM: Porcine circovirus

<400> SEQUENCE: 11

```
Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110
```

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
210                 215                 220

Asn Leu Lys Asp Pro Pro Leu Lys Pro
225                 230

<210> SEQ ID NO 12
<211> LENGTH: 713
<212> TYPE: DNA
<213> ORGANISM: Porcine circovirus

<400> SEQUENCE: 12
cagctatgac gtatccaagg aggcgttacc gcagaagaag acaccgcccc gcagccatc       60
ttggccagat cctccgccgc cgcccctggc tcgtccaccc ccgccaccgc taccgttgga     120
gaaggaaaaa tggcatcttc aacacccgcc tctcccgcac cttcggatat actgtggaga     180
aggaaaaatg gcatcttcaa cacccgcctc tcccgcacct tcggatatac tgtgacgact     240
tgttccccc gggaggggg accaacaaaa tctctatacc ctttgaatac tacagaataa      300
gaaaggttaa ggttgaattc tggccctgct ccccatcac caggtgtgat aggggagtgg      360
gctccactgc tgttattcta gatgataact ttgtaacaaa ggccacagcc ctaacctatg     420
acccatatgt aaactactcc tcccgccata caatccccca accctctct accactccc      480
gttacttcac acccaaacct gttcttgact ccactattga ttacttccaa ccaataaca      540
aaaggaatca gctttggctg aggctacaaa cctctagaaa tgtggaccac gtaggcctcg     600
gcactgcgtt cgaaaacagt aaatacgacc aggactacaa tatccgtgta accatgtatg     660
tacaattcag agaatttaat cttaaagacc ccccacttaa accctaaatg aat             713

<210> SEQ ID NO 13
<211> LENGTH: 233
<212> TYPE: PRT
<213> ORGANISM: Porcine circovirus

<400> SEQUENCE: 13

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
        50                  55                  60

Pro Ser Trp Ala Val Asp Met Met Arg Phe Asn Ile Asp Asp Phe Val
65                  70                  75                  80

```
Pro Pro Gly Gly Gly Thr Asn Lys Ile Ser Ile Pro Phe Glu Tyr Tyr
            85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
        130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
            195                 200                 205

Gln Asp Tyr Asn Ile Arg Val Thr Met Tyr Val Gln Phe Arg Glu Phe
        210                 215                 220

Asn Leu Lys Asp Pro Pro Leu Glu Pro
225                 230
```

```
<210> SEQ ID NO 14
<211> LENGTH: 713
<212> TYPE: DNA
<213> ORGANISM: Porcine circovirus

<400> SEQUENCE: 14
ccgccatgac gtatccaagg aggcgttacc gcagaagaag acaccgcccc cgcagccatc      60
ttggccagat cctccgccgc cgcccctggc tcgtccaccc ccgccaccgc taccgttgga    120
gaaggaaaaa tggcatcttc aacacccgcc tctcccgcac cttcggatat actgtcaagg    180
ctaccacagt cacaacgccc tcctgggcgg tggacatgat gagatttaat attgacgact    240
ttgttccccc gggagggggg accaacaaaa tctctatacc ctttgaatac acagaataa    300
gaaaggttaa ggttgaattc tggccctgct cccccatcac ccagggtgat aggggagtgg    360
gctccactgc tgttattcta gatgataact ttgtaacaaa ggccacagcc taacctatg    420
acccatatgt aaactactcc tcccgccata caatccccca accttctcc taccactccc    480
gttacttcac acccaaacct gttcttgact ccactattga ttacttccaa ccaaataaca    540
aaaggaatca gctttggctg aggctacaaa cctctagaaa tgtggaccac gtaggcctcg    600
gcactgcgtt cgaaaacagt aaatacgacc aggactacaa tatccgtgta accatgtatg    660
tacaattcag agaatttaat cttaaagacc ccccacttga accctaagaa ttc            713

<210> SEQ ID NO 15
<211> LENGTH: 233
<212> TYPE: PRT
<213> ORGANISM: Porcine circovirus

<400> SEQUENCE: 15

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45
```

```
Leu Ser Arg Thr Phe Gly Tyr Thr Val Lys Ala Thr Val Arg Thr
     50                  55                  60

Pro Ser Trp Ala Val Asp Met Met Arg Phe Asn Ile Asp Asp Phe Val
 65              70                  75                  80

Pro Pro Gly Gly Gly Thr Asn Lys Ile Ser Ile Pro Phe Glu Tyr Tyr
                 85                  90                  95

Arg Ile Lys Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
                115                 120                 125

Phe Val Thr Lys Ala Thr Ala Leu Thr Tyr Asp Pro Tyr Val Asn Tyr
        130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
                180                 185                 190

Val Asp His Val Gly Leu Gly Thr Ala Phe Glu Asn Ser Ile Tyr Asp
            195                 200                 205

Gln Asp Tyr Asn Ile Arg Val Thr Met Tyr Val Gln Phe Arg Glu Phe
        210                 215                 220

Asn Leu Lys Asp Pro Pro Leu Lys Pro
225                 230

<210> SEQ ID NO 16
<211> LENGTH: 15450
<212> TYPE: DNA
<213> ORGANISM: Porcine reproductive and respiratory syndrome virus

<400> SEQUENCE: 16
atgacgtata ggtgttggct ctatgccacg gcatttgtat tgtcaggagc tgtggccatt      60
ggcacagccc aaaacttgct gcacggaaaa cgcccttctg tgacagcctt cttcagggga     120
gcttaggggt ctgtccctag caccttgctt ctggagttgc actgctttac ggtctctcca     180 ccccttaac catgtctggg atacttgatc ggtgcacgtg cacccccaat gccagggtgt      240
ttatggcgga gggccaagtc tactgcacac gatgtctcag tgcacggtct ctccttcctc     300
tgaatctcca agttcctgag cttggggtgc tgggcctatt ttataggccc gaagagccac     360
tccggtggac gttgccacgt gcattcccca ctgtcgagtg ctcccctgcc ggggcctgct     420
ggctttctgc gatctttcca attgcacgaa tgaccagtgg aaacctgaac tttcaacaaa     480
gaatggtgcg ggttgcagct gagatttaca gaccggcca actcacccct gcagttttga     540
aggctctaca agtttatgaa cggggttgtc gctggtaccc cattgtcgga cctgtccctg     600
gagtggccgt ttacgccaac tccctacatg tgagtgacaa acctttcccg ggagcaactc     660
atgtgttaac caacctaccg ctcccgcaga ggcccaagcc tgaagacttt tgcccttttg     720
agtgtgctat ggctaacgtc tatgacattg ccataacgc cgtcatgtat gtggccagag     780
ggaaagtctc ctgggccct cgtggcgggg atgaagtgaa atttgaaacc gtccccgaag     840
agttgaagtt gattgcgaac cgactccaca tctccttccc gccccaccac gcagtggaca     900
tgtctgagtt tgccttcata gcccctggga gtggtgtctc cttgcgggtc gagcaccaac     960
acggctgcct tcccgctgat actgtccctg atgggaactg ctggtggtac ttgtttgact    1020
```

```
tgctcccacc ggaagttcag aataaagaaa ttcgccgtgc taaccaattt ggctatcaaa    1080
ccaagcatgg tgtccatggc aagtacctac agcggaggct gcaagttaat ggtctccgag    1140
cagtgactga tacagatgga cctattgtcg tacagtactt ctctgttagg gagagttgga    1200
tccgccactt cagactggcg gaagaaccta gcctccctgg gtttgaagac ctcctcagaa    1260
taagggtaga gcctaatacg tcgccaatgg gtggcaaggg tgaaaaaatc ttccggtttg    1320
gcagtcacaa gtggtacggt gctggaaaga gagcaaggag agcacgctct ggtgcgactg    1380
ccacggtcgc tcaccgcgct ttgcccgctc gcgaagccca gcaggccaag aagctcgagg    1440
ttgccagcgc caacagggct gagcatctca agtactattc cccgcctgcc gacgggaact    1500
gtggttggca ctgcatttcc gccattacca accggatggt gaattccaaa tttgaaacca    1560
ctcttcccga gagagtgaga ccttcagatg actgggctac tgacgaggat cttgtgaata    1620
ccatccaaat cctcaggctc cccgcggcct tggacaggaa cggtgcttgt gctggcgcca    1680
agtacgtgct caagctggaa ggtgagcact ggaccgtctc tgtgacccct gggatgaccc    1740
cttctttgct ccccccttgaa tgtgttcagg gttgttgtga gcataagagc ggtcttggtt    1800
tcccagacgt ggtcgaagtt ccggatttga ccctgcctg tcttgaccga cttgctgaga    1860
taatgcactt gcctagcagt gtcatcccag ctgctctggc cgagatgtcc gacgacttca    1920
atcgtctggc ttccccggcc gccactgtgt ggactgtttc gcaattcttt gcccgccaca    1980
gaggaggaga gcatcctgac caggtgtgct tagggaaaat tatcaacctt tgtcaggtga    2040
ttgaggaatg ctgctgttcc ggaacaaag ccaaccgggc taccccggaa gaggttgcgg    2100
caaaagttga ccagtacctc cgtggtgcag caagccttgg agaatgcttg ccaagcttg    2160 agagggctcg cccgccgagc gcgacggaca cctcctttga ttggaatgtt gtgcttcctg    2220
gggttgagac ggcgaatcag acaaccaaac agctccatgt caaccagtgc cgcgctctgg    2280
ttcctgtcgt gactcaagag ccttttggaca gagactcggt ccctctgacc gccttctcgc    2340
tgtccaattg ctactaccct gcacaaggtg acgaggtccg tcaccgtgag aggctaaact    2400
ccttgctctc taagttggag ggggttgttc gtgaggaata tgggctcacg ccaactggac    2460
ctggcccgcg acccgcactg ccgaacgggc tcgacgagct taaagaccag atggaggagg    2520
atctgctgaa attagtcaac gcccaggcaa cttcagaaat gatggcctgg gcagccgagc    2580
aggttgatct aaaagcttgg gtcaaaaatt ccccacggtg gacaccgcca cccctccac    2640 caagagttca gcctcgaaaa acgaagtctg tcaagagctt gctagagaac aagcctgtcc    2700
ctgctccgcg caggaaggtc agatctgatt gtggcagccc gattttgatg ggcgacaatg    2760
ttcctaacgg ttgggaagat tcgactgttg gtggtcccct tgatctttcg gcaccatccg    2820
agccgatgac acctctgagt gagcctgtac ttatttccag gccagtgaca tctttgagtg    2880
tgccggcccc agttcctgca ccgcgtagag ctgtgtcccg accgatgacg ccctcgagtg    2940
agccaatttt tgtgtctgca ctgcgacaca aatttcagca ggtggaaaaa gcaaatctgg    3000
cggcagcagc gccgatgtgc caggacgaac ccttagattt gtctgcatcc tcacagactg    3060
aatatgaggc ttccccccta acaccaccgc agaacgtggg cattctggag gtaaggggc    3120 aagaagctga ggaagttctg agtgaaatct cggatattct gaatgatacc aaccctgcac    3180
ctgtgtcatc aagcagctcc ctgtcaagtg ttaagatcac acgcccaaaa tactcagctc    3240
aagccattat cgactcgggc gggccctgca gtgggcacct ccaaagggaa aagaagcat    3300 gcctccgcat catgcgtgaa gcttgtgatg cggccaagct tagtgaccct gccacgcagg    3360
aatggctttc tcgcatgtgg gatagggtgg acatgctgac ttggcgcaac acgtctgctt    3420
```

```
accaggcgtt tcgcacccta gatggcaggt ttgggtttct cccaaagatg atactcgaga   3480
cgccgccgcc ctacccgtgt gggtttgtga tgttgcctca caccctgca ccttccgtga    3540 gtgcagagag cgaccttacc attggttcag tcgccactga agatattcca cgcatcctcg   3600
ggaaaataga aaataccggt gagatgatca accaggacc cttggcatcc tctgaggaag    3660
aaccggtata caaccaacct gccaaagact cccggatatc gtcgcggggg tctgacgaga   3720
gcacagcagc tccgtccgcg gtacagqtg cgccggctt atttactgat ttgccacctt    3780
cagacggcgt agatgcggac ggtgggggc cgttgcagac ggtaagaaag aaagctgaaa    3840
ggctcttcga ccaattgagc cgtcaggttt ttaacctcgt ctcccatctc cctgttttct   3900
tctcacacct cttcaaatct gacagtggtt attctccggg tgattggggt tttgcagctt   3960
ttactctatt ttgcctcttt ttgtgttaca gctacccatt cttcggtttc gttccctct   4020 tgggtgtatt ttctgggtct tctcggcgtg tgcgcatggg ggttttggc tgctggctgg    4080 cttttgctgt tggcctgttc aagcctgtgt ccgacccagt cggcactgct tgtgagtttg   4140
actcgccaga gtgcaggaac gtccttcatt cttttgagct tctcaaacct tgggacctg    4200 ttcgcagcct tgttgtggc cccgtcggtc tcggtcttgc cattcttggc aagttactgg    4260
gcggggcacg ctacatctgg cattttttgc ttaggcttgg cattgttgca gattgtatct   4320
tggctggagc ttatgtgctt tctcaaggta ggtgtaaaaa gtgctgggga tcttgtataa   4380
gaactgctcc taatgaaatc gccttcaacg tgttcccttt tacacgtgcg accaggtcgt   4440
cactcatcga cctgtgcgat cggttttgtg cgccaacagg catggacccc attttcctcg   4500
ccactgggtg gcgtgggtgc tggaccggcc gaagtcccat tgagcaaccc tctgaaaaac   4560
ccatcgcgtt cgcccagttg gatgaaaaga ggattacggc tagaactgtg gtcgctcagc   4620
cttatgatcc taatcaagcc gtgaagtgct tgcgggtgtt acaggcgggt ggggcgatgg   4680 tggccgagge agtcccaaaa gtggccaaag tttctgctat tccattccga gccccttttt   4740
ttcccaccgg agtgaaagtt gatcccgagt gcaggatcgt ggttgacccc gatactttta   4800
ctacagccct ccggtctggt tactctacca caaacctcgt ccttggtgtg gggacttt    4860 cccagctgaa tggactaaag atcaggcaaa tttccaagcc ttcgggagga ggcccacacc   4920
tcattgctgc cctgcatgtt gcctgctcga tggcgttgca catgcttgct ggggtttatg   4980
taacttcagt ggggtcttgc ggtgccggca ccaacgatcc atggtgcact aatccgtttg   5040
ccgttcctgg ctacggacca ggctctctct gcacgtccag attgtgcatc tcccaacatg   5100 gccttacccct gcccttgaca gcacttgtgg cgggattcgg tcttcaggaa atcgccttgg   5160
tcgttttgat tttcgtttcc atcggaggca tggctcatag gttgagttgt aaggctgata   5220
tgctgtgcat tttacttgca atcgccagct atgtttgggt accccttacc tggttgcttt   5280
gtgtgtttcc ttgttggttg cgctggttct cttgcaccc ccttaccatc ctatggttgg    5340 tgttttctt gatttctgta aatatgcctt cgggaatctt ggccgtggtg ttattggttt    5400
ctctttggct tttgggacgt tatactaaca ttgctggtct tgtcaccccc tatgatattc   5460
atcattacac cagtggccc cgcggtgttg ccgccttggc taccgcacca gatggaacct   5520
acttggctgc cgtccgccgc gctgcgttga ctggtcgcac catgctgttc accccgtctc   5580
agcttgggtc ccttcttgag ggcgctttca gaactcgaaa gccctcactg aacaccgtca   5640
atgtggttgg gtcctccatg ggctctggtg gagtgttcac catcgacggg aaaattaggt   5700
gcgtgactgc cgcacatgtc cttacgggta attcggctag ggttccgga gtcggcttca   5760
```

```
atcaaatgct tgactttgat gtgaaagggg acttcgccat agctgattgc ccgaattggc    5820
aaggagctgc tcccaagacc caattctgcg aggacggatg gactggccgt gcctattggc    5880
tgacatcctc tggcgtcgaa cccggtgtta ttgggaatgg attcgccttc tgcttcaccg    5940
cgtgcggcga ttccgggtcc ccagtgatca ccgaagctgg tgagattgtc ggcgttcaca    6000
caggatcaaa taaacaagga ggtggcatcg tcacgcgccc ttcaggccag ttttgtaacg    6060
tggcacccat caagctgagc gaattaagtg aattcttttgc tggacccaag gtcccgctcg    6120
gtgatgtgaa ggttggcagc cacataatta agacacgtg cgaagtacct tcagatcttt    6180
gcgccttgct tgctgccaaa cctgaactgg agggaggcct ctccaccgtc caacttctgt    6240
gtgtgttttt cctactgtgg agaatgatgg gacatgcctg gacgcccttg gttgctgtgg    6300
ggtttttcat tctgaatgag gttctcccag ctgtcctggt tcggagtgtt ttctcctttg    6360
ggatgtttgt gctatcttgg ctcacaccat ggtctgcgca agttctgatg atcaggcttc    6420
taacagcagc tcttaacagg aacagatggt cacttgcctt ttacagcctt ggtgcggtga    6480
ccggttttgt cgcagatctt gcggtaactc aagggcaccc gttgcaggca gtaatgaatt    6540
tgagcaccta tgccttcctg cctcggatga tggttgtgac ctcaccagtc ccagtgattg    6600
cgtgtggtgt tgtgcaccta cttgccatca ttttgtactt gttcaagtac cgcggcctgc    6660
acaatgttct tgttggtgat ggagcgtttt ctgcagcttt cttcttgcga tactttgccg    6720
agggaaagtt gagggaaggg gtgtcgcaat cctgcgaaat gaatcatgag tcattgactg    6780
gtgccctcgc tatgagactc aatgacgagg acttggactt ccttacgaaa tggactgatt    6840
ttaagtgctt tgtttctgcg tccaacatga ggaatgcagc aggccaattc atcgaggctg    6900
cctatgcaaa agcacttaga attgaacttg cccagttggt gcaggttgat aaggttcgag    6960
gtactttggc caagcttgag gcttttgctg ataccgtggc accccaactc tcgcccggtg    7020
acattgttgt tgctcttggc catacgcctg ttggcagcat cttcgaccta aaggttggtg    7080
gtaccaagca tactctccaa gtcattgaga ccagagtcct tgccgggtcc aaaatgaccg    7140
tggcgcgcgt cgttgaccca acccccacgc ccccacccgc acccgtgccc atccccctcc    7200
caccgaaagt tctagagaat ggtcccaacg cctgggggga tggggaccgt ttgaataaga    7260
agaagaggcg taggatggaa accgtcggca tctttgtcat gggtgggaag aagtaccaga    7320
aattttggga caagaattcc ggtgatgtgt tttacgagga ggtccatgac aacacagatg    7380
cgtgggagtg cctcagagtt ggtgaccctg ccgactttaa ccctgagaag ggaactctgt    7440
gtgggcatac tactattgaa gataaggatt acaaagtcta cgcctcccca tctggcaaga    7500
agttcctggt ccccgtcaac ccagagagcg gaagagccca atgggaagct gcaaagcttt    7560
ccgtggagca ggcccttggc atgatgaatg tcgacggtga actgacgccc aaagaagtgg    7620
agaaactgaa aagaataatt gacaaacttc agggccttac taaggagcag tgtttaaact    7680
gctagccgcc agcggcttga cccgctgtgg tcgcggcggc ttggttgtta ctgagacagc    7740
ggtaaaaata gtcaaatttc acaaccggac tttcacccta gggcctgtga atttaaaagt    7800
ggccagtgag gttgagctga agacgcggt cgagcacaac caacacccgg ttgcaagacc    7860
ggttgacggt ggtgttgtgc tcctgcgttc cgcagttcct tcgcttatag atgtcctgat    7920
ctccggtgct gacgcatctc ctaagttact cgctcgtcac gggccgggga acactgggat    7980
cgatggcacg ctttgggact ttgaggccga ggcaccaaaa gaggaaattg cgctcagtgc    8040
gcaaataata caggcttgtg acattaggcg cggtgacgca cctgaaattg gtctccctta    8100
caagctgtac cctgttaggg gcaaccctga gcgggtaaaa ggagttttac agaatacaag    8160
```

```
gtttggagac ataccttaca aaaccccag tgacactggg agcccagtgc acgcggctgc    8220
ctgcctcacg cccaatgcca ctccggtgac tgatgggcgc tccgtcttgg ctactaccat    8280
gccctccggt tttgaattgt atgtaccgac cattccagcg tctgtccttg attatcttga    8340
ctctaggcct gactgcccca aacagttgac agagcacggc tgtgaggatg ccgcattgag    8400
agacctctcc aagtatgact tgtccaccca aggctttgtt ttacctgggg ttcttcgcct    8460
tgtgcgtaag tacctgtttg cccacgtggg taagtgcccg cccgttcatc ggccttccac    8520
ttaccctgcc aagaattcta tggctggaat aaatgggaac aggtttccaa ccaaggacat    8580
tcagagcgtc cccgaaatcg acgttctgtg cgcacaggcc gtgcgagaaa actggcaaac    8640
tgttacccct tgtaccctca agaaacagta ttgtgggaag aagaagacta ggacaatact    8700
cggcaccaat aatttcattg cgttggccca ccgggcagcg ttgagtggtg tcacccaggg    8760
cttcatgaaa aaggcgttta actcgcccat cgccctcggg aaaaacaaat taaggagct    8820 acagactccg atcttaggca ggtgccttga agctgatctt gcatcctgtg atcgatccac    8880
acctgcaatt gtccgctggt ttgccgccaa ccttctttat gaacttgcct gtgctgaaga    8940
gcacctaccg tcgtacgtgc tgaactgctg ccatgaccta ttggtcacgc agtccggcgc    9000
agtgactaag aggggtggcc tgtcgtctgg cgacccgatc acttctgtgt ctaacaccat    9060
ttacagcttg gtgatatatg cacagcacat ggtgcttagt tactttaaaa gtggtcaccc    9120
tcatggcctt ctgttcctac aagaccagct gaagttcgag gacatgctca agtccaacc    9180 cctgatcgtc tattcggacg acctcgtgct gtatgccgaa tctcccacca tgccgaacta    9240
ccactggtgg gtcgaacatc tgaatttgat gctgggtttt cagacggacc aaagaagac    9300 agccataacg gactcgccat catttctagg ctgtaggata taaatggac gccagctagt    9360 ccccaaccgt gacaggatcc tcgcggccct cgcttaccat atgaaggcaa acaatgtttc    9420
tgaatactac gccgcggcgg ctgcaatact catggacagc tgtgcttgtt tagagtatga    9480
tcctgaatgg tttgaagagc ttgtggttgg gatagcgcat tgcgcccgca aggacggcta    9540
cagctttccc ggcccgccgt tcttcttgtc catgtgggaa aaactcagat ccaatcatga    9600
ggggaagaag tccagaatgt gcgggtattg cggggccctg gctccgtacg ccactgcctg    9660
tggcctcgac gtctgtattt accacaccca cttccaccag cattgtccag tcacaatctg    9720
gtgtggccac ccggctggtt ctggttcttg tagtgagtgc aaaccccccc tagggaaagg    9780
cacaagccct ctagatgagg tgttagaaca agtcccgtat aagcctccac ggactgtaat    9840
catgcatgtg gagcagggtc tcacccctct tgacccaggc agataccaga ctcgcgcgg    9900 attagtctcc gttaggcgtg gcatcagagg aaatgaagtt gacctaccag acggtgatta    9960
tgctagcacc gccctactcc ccacttgtaa agagatcaac atggtcgctg tcgcctctaa   10020
tgtgttgcgc agcaggttca tcatcggtcc gcccggtgct gggaaaacat actggctcct   10080
tcagcaggtc caggatggtg atgtcattta cacaccgact caccagacca tgctcgacat   10140
gattagggct ttggggacgt gccggttcaa cgtcccagca ggtgcaacgc tgcaattccc   10200
tgccccctcc cgtaccggcc cgtgggttcg catcctagcc ggcggttggt gtcctggtaa   10260
gaattccttc ttgatgaag cagcgtattg taatcacctt gatgtcttga ggtcccttag   10320
caaaaccacc ctcacctgtc tgggagactt caaacaactc cacccagtgg gttttgattc   10380
tcattgctat gttttgaca tcatgcctca gacccagttg aagaccatct ggagattcgg   10440
acagaacatc tgtgatgcca tccaaccaga ttacagggac aaacttgtgt ccatggtcaa   10500
```

```
cacaacccgt gtaacccacg tggaaaaacc tgtcaagtat gggcaagtcc tcacccctta    10560
ccacagggac cgagaggacg gcgccatcac aattgactcc agtcaaggcg ccacatttga    10620
tgtggtcaca ctgcatttgc ccactaaaga ttcactcaac aggcaaagag cccttgttgc    10680
tatcaccagg gcaagacatg ctatctttgt gtatgaccca cacaggcaat tgcagagcat    10740
gtttgatctt cctgcgaagg gcacacccgt caacctcgca gtgcaccgtg atgagcagct    10800
gatcgtactg gatagaaata ataaagaatg cacagttgct caggctctag caacggaga    10860 taaatttagg gccaccgaca agcgcgttgt agattctctc cgcgccattt gtgctgatct    10920
ggaagggtcg agctctccgc tccccaaggt cgcacacaac ttgggatttt atttctcacc    10980
tgatttgaca cagtttgcta aactcccggt agaccttgca ccccactggc ccgtggtgac    11040
aacccagaac aatgaaaagt ggccggatcg gctggttgcc agccttcgcc ctgtccataa    11100
gtatagccgt gcgtgcattg gtgccggcta tggtgggc ccctcggtgt ttctaggcac    11160
ccctggggtc gtgtcatact acctcacaaa atttgtcaag ggcgaggctc aagtgcttcc    11220
ggagacagtc ttcagcaccg gccgaattga ggtggattgc cgggagtatc ttgatgacag    11280
ggagcgagaa gttgctgagt ccctcccaca tgccttcatt ggcgacgtca aaggcaccac    11340
cgttggggga tgtcatcatg tcacctccaa ataccttccg cgcttccttc caaggaatc    11400 agtcgcggta gtcggggttt cgagccccgg gaaagccgca aaagcagtgt gcacattgac    11460
ggatgtgtac ctcccagacc ttgaggccta cctccaccca gagactcagt ccaagtgctg    11520
gaaagttatg ttggacttca aggaagttcg actgatggtc tggaaagaca agacggccta    11580
tttccaactt gaaggccgct atttcacctg gtatcagctt gcaagctacg cctcgtacat    11640
ccgtgttcct gtcaactcca cggtgtatct ggacccctgc atgggccctg ccctttgcaa    11700
cagaagagtt gtcgggtcca cccattgggg agctgacctc gcagtcaccc cttatgatta    11760
cggtgctaaa atcatcttgt ctagcgctta ccatggtgaa atgcctcctg gatacaagat    11820
tctggcgtgc gcggagttct cgctcgacga cccagtcaag tacaaacaca cctggggttt    11880
tgaatcggat acagcgtatc tgtatgagtt caccggaaac ggtgaggact gggaggatta    11940
caatgatgcg tttcgtgcgc gccagaaagg gaaaatttat aaggccactg ctaccagcat    12000
gaagttttat tttccccccgg gccccgtcat tgaaccaact ttaggcctga attgaaatga    12060 aatgggtct atacaaagcc tcttcgacaa aattggccag cttttttgtgg atgctttcac    12120 ggaattttg gtgtccattg ttgatatcat catattttg gccattttgt ttggcttcac    12180
catcgccggt tggctggtgg tcttttgcat cagattggtt tgctccgcgg tattccgtgc    12240
gcgccctgcc attcaccctg agcaattaca gaagatccta tgaggccttt ctttctcagt    12300
gccgggtgga cattcccacc tgggggtaa acacccttt ggggatgttt tggcaccata    12360
aggtgtcaac cctgattgat gaaatggtgt cgcgtcgaat gtaccgcgtc atggataaag    12420
cagggcaagc tgcctggaaa caggtggtga gcgaggctac gctgtctcgc attagtagtc    12480
tggatgtggt ggctcatttt caacatcttg ccgccattga agccgagacc tgtaaatatt    12540
tggcttctcg actgcccatg ctacacaacc tgcgcatgac agggtcaaat gtaaccatag    12600
tgtataatag cactttaaat caggtgtttg ctattttcc aaccctggt tcccggccaa    12660 agcttcatga ttttcagcaa tggctaatag ctgtacattc ctccatattt tcctctgttg    12720
cagcttcttg tactctttt gttgtgctgt ggttgcgggt tccaatgcta cgtactgttt    12780
ttggtttccg ctggttaggg gcaatttttc tttcgaactc atggtgaatt acacggtgtg    12840
tccaccttgc ctcacccgac aagcagccgc tgaggtcctt gaacccggta ggtctctttg    12900
```

```
gtgcaggata gggcatgacc gatgtgggga ggacgatcac gacgaactgg ggttcatggt   12960
tccgcctggc ctctccagcg aaagccactt gaccagtgtt tacgcctggt tggcgttcct   13020
gtccttcagc tacacggccc agttccatcc cgagatattt gggataggga acgtgagtga   13080
agtttatgtt gacatcaagc accaattcat ctgcgccgtt catgacgggc agaacaccac   13140
cttgcctcgc catgacaata tttcagccgt atttcagacc tactatcaac atcaggtcga   13200
cggcggcaat tggtttcacc tagaatggct gcgtcccttc ttttcctctt ggttggtttt   13260
aaatgtttcg tggtttctca ggcgttcgcc tgcaagccat gtttcagttc gagtctttca   13320
gacatcaaaa ccaacactac cgcagcatca ggctttgttg tcctccagga catcagctgc   13380
cttaggcatg gcgactcgtc ctttccgacg attcgcaaaa gctctcaatg ccgcacggcg   13440
atagggacac ctgtgtatat caccatcaca gccaatgtga cagatgagaa ttacttacat   13500
tcttctgatc tcctcatgct ttcttcttgc cttttctatg cttctgagat gagtgaaaag   13560
ggattcaagg tggtatttgg caatgtgtca ggcatcgtgg ctgtgtgtgt caactttacc   13620
agctacgtcc aacatgtcaa agagtttact caacgctcct tggtggtcga tcatgtgcgg   13680
ctgcttcatt tcatgacacc tgagaccatg aggtgggcaa ccgttttagc ctgtcttttt   13740
gccatcctac tggcaatttg aatgttcaag tatgttgggg aaatgcttga ccgcgggctg   13800
ttgctcgcga ttgctttctt tgtggtgtat cgtgccgttc tggtttgctg tgctcggcaa   13860
cgccaacagc agcagcagct ctcatttcca gttgatttat aacttgacgc tatgtgagct   13920
gaatggcaca gattggctgg cagaaaaatt tgattgggcg gtggagactt ttgtcatctt   13980
tcccgtgttg actcacattg tttcctattg tgcactcacc accagccatt tccttgacac   14040
agttggtctg gttactgtgt ccaccgccgg gttttatcac gggcggtatg tcttgagtag   14100
catctacgcg gtctgtgctc tggctgcgtt gatttgcttc gttattaggc ttgcgaagaa   14160
ctgcatgtcc tggcgctact cttgtaccag atataccaac ttccttctgg acactaaggg   14220
cagactctat cgttggcggt cgcccgttat catagaaaaa aggggtaagg ttgaggtcga   14280
aggtcatctg atcgacctca aaagagttgt gcttgatggt tccgtggcaa ccccttttaac   14340 cagagtttca gcggaacaat ggggtcgtct ctagacgact tttgccatga tagcactgct   14400
ccacaaaagg tgcttttggc gttttccatt acctacacgc cagtaatgat atatgctcta   14460
aaggtaagtc gcggccgact gctagggctt ctgcaccttt tgatctttct gaattgtgct   14520
tttaccttcg ggtacatgac attgcgcac tttcagagca caaatagggt cgcgctcgct   14580
atgggagcag tagttgcact tctttggggg gtgtactcag ccatagaaac ctggaaattc   14640
atcacctcca gatgccgttt gtgcttgcta ggccgcaagt acattctggc ccctgcccac   14700
cacgtcgaaa gtgccgcggg ctttcatccg attgcggcaa atgataacca cgcatttgtc   14760
gtccggcgtc ccggctccat tacggttaac ggcacattgg tgcccgggtt gaaaagcctc   14820
gtgttgggtg gcagaaaagc tgttaaacag ggagtggtaa accttgtcaa atatgccaaa   14880
taacaacggc aagcagcaaa agaaaaagaa ggggaatggc cagccagtca accagctgtg   14940
ccagatgctg ggtaaaatca tcgcccagca aaaccagtcc agaggcaagg gaccgggcaa   15000
gaaaagtaag aagaaaaacc cggagaagcc ccatttttcct ctagcgaccg aagatgacgt   15060
caggcatcac ttcaccctg gtgagcggca attgtgtctg tcgtcgatcc agactgcctt   15120
taaccagggc gctggaactt gtaccctgtc agattcaggg aggataagtt acactgtgga   15180
gtttagtttg ccgacgcatc atactgtgcg cctgatccgc gtcacagcat caccctcagc   15240
```

-continued

| | |
|---|---|
| atgatgggct ggcattcttt aggcacctca gtgtcagaat tggaagaatg tgtggtggat | 15300 |
| ggcactgatt gacattgtgc ctctaagtca cctattcaat tagggcgacc gtgtgggggt | 15360 |
| aaaatttaat tggcgagaac catgcggccg caattaaaaa aaaaaaaaaa aaaaaaaaaa | 15420 |
| aaaaaaaaaa aaaaaaaaaa aaaaaaaaaa | 15450 |

<210> SEQ ID NO 17
<211> LENGTH: 2352
<212> TYPE: DNA
<213> ORGANISM: Porcine reproductive and respiratory syndrome virus

<400> SEQUENCE: 17

| | |
|---|---|
| cctatcattg aaccaacttt aggcctgaat tgaaatgaaa tggggtctat gcaaagcctt | 60 |
| tttgacaaaa ttggccaact tttcgtggat gctttcacgg agttcttggt gtccattgtt | 120 |
| gatatcatta tattttggc cattttgttt ggcttcacca tcgccggttg gctggtggtc | 180 |
| ttttgcatca gattggtttg ctccgcgata ctccgtgcgc gccctgccat tcactctgag | 240 |
| caattacaga agatcctatg aggcctttct ttctcagtgc caggtggaca ttcccacctg | 300 |
| gggaattaaa catccttggg gatgctttg gcaccataag gtgtcaaccc tgattgatga | 360 |
| aatggtgtcg cgtcgaatgt accgcatcat ggaaaaagca ggacaggctg cctggaaaca | 420 |
| ggtggtgagc gaggctacgc tgtctcgcat tagtagtttg gatgtggtgg ctcactttca | 480 |
| gcatcttgcc gccattgaag ccgagacctg taaatatttg gcctctcggc tgcccatgct | 540 |
| acacaacctg cgcatgacag ggtcaaatgt aaccatagtg tataatagta ctttgaatca | 600 |
| ggtgcttgct attttcccaa cccctggttc ccggccaaag cttcatgatt ttcagcaatg | 660 |
| gctaatagct gtacattcct ctatattttc ctctgttgca gcttcttgta ctcttttttgt | 720 |
| tgtgctgtgt tgcgggttc aatgctacg tattgctttt ggtttccgct ggttaggggc | 780 |
| aatttttctt tcgaactcac agtgaactac acggtgtgtc caccttgcct cacccggcaa | 840 |
| gcagccacag aggcctacga acctggcagg tctctttggt gcaggatagg gtatgatcgc | 900 |
| tgtggggagg acgatcatga tgaactaggg tttgtggtgc cgtctggcct ctccagcgaa | 960 |
| ggccacttga ccagtgttta cgcctggttg gcgttcctgt ctttcagtta cacagcccag | 1020 |
| ttccatcctg agatattcgg gatagggaat gtgagtcaag tttatgttga catcaggcat | 1080 |
| caattcattt gcgccgttca cgacgggcag aacgccactt tgcctcgcca tgacaatatt | 1140 |
| tcagccgtgt tccagactta ttaccaacat caagtcgacg cggcaattg gtttcaccta | 1200 |
| gaatggctgc gtcccttctt ttcctcttgg ttggttttaa atgtctcttg gtttctcagg | 1260 |
| cgttcgcctg caagccatgt ttcagttcga gtcttgcaga cattaagacc aacaccaccg | 1320 |
| cagcggcagg ctttgctgtc ctccaagaca tcagttgcct taggtatcgc aactcggcct | 1380 |
| ctgaggcgtt tcgcaaaatc cctcagtgtc gtacggcgat agggacaccc atgtatatta | 1440 |
| ctgtcacagc caatgtaacc gatgagaatt atttgcattc ctctgacctt ctcatgcttt | 1500 |
| cttcttgcct tttctacgct tctgagatga gtgaaaaggg atttaaagtg gtatttggca | 1560 |
| atgtgtcagg catcgtggct gtgtgcgtca actttaccag ctacgtccaa catgtcaagg | 1620 |
| aatttaccca acgctccttg gtagtcgacc atgtgcggct gctccatttc atgacacctg | 1680 |
| agaccatgag gtgggcaact gtttagcct gtcttttgc cattctgttg gccatttgaa | 1740 |
| tgtttaagta tgttggggaa atgcttgacc gcgggctatt gctcgtcatt gctttttttg | 1800 |
| tggtgtatcg tgccgtcttg gtttgttgcg ctcgccagcg ccaacagcag caacagctct | 1860 |
| catttacagt tgatttataa cttgacgcta tgtgagctga atggcacaga ttggttagct | 1920 |

```
ggtgaatttg actgggcagt ggagtgtttt gtcattttc ctgtgttgac tcacattgtc    1980
tcctatggtg ccctcaccac cagccatttc cttgacacag tcggtctggt cactgtgtct    2040
accgccggct tttcccacgg gcggtatgtt ctgagtagca tctacgcggt ctgtgccctg    2100
gctgcgttga tttgcttcgt cattaggttt acgaagaatt gcatgtcctg gcgctactca    2160
tgtaccagat ataccaactt tcttctggac actaagggca gactctatcg ttggcggtcg    2220
cctgtcatca tagagaaaag gggtaaagtt gaggtcgaag gtcatctgat cgacctcaag    2280
agagttgtgc ttgatggttc cgcggcaacc cctataacca aagtttcagc ggagcaatgg    2340
ggtcgtcctt ag                                                        2352

<210> SEQ ID NO 18
<211> LENGTH: 886
<212> TYPE: DNA
<213> ORGANISM: Porcine reproductive and respiratory syndrome virus

<400> SEQUENCE: 18
atggggtcgt ccttagatga cttctgccat gatagcacgg ctccacaaaa ggtgcttttg      60
gcgttctcta ttacctacac gccagtgatg atatatgccc taaaagtaag tcgcggccga     120
ctgctagggc ttctgcacct tttgatcttc ctaaattgtg ctttcacctt cgggtacatg     180
acattcgtgc actttcagag cacaaacaag gtcgcgctca ctatgggagc agtagttgca     240
ctcctttggg gggtgtactc agccatagaa acctggaaat tcatcacctc cagatgccgt     300
ttgtgcttgc taggccgcaa gtacattttg gcccctgccc accacgttga aagtgccgca     360
ggctttcatc cgatagcggc aaatgataac cacgcatttg tcgtccggcg tcccggctcc     420
actacggtta acggcacatt ggtgcccggg ttgaaaagcc tcgtgttggg tggcagaaaa     480
gctgtcaaac agggagtggt aaaccttgtt aaatatgcca ataacaacg gcaagcagca     540 gaagaaaaag aaggggatg gccagccagt caatcagctg tgccagatgc tgggtaagat     600
catcgctcag caaaaccagt ccagaggcaa gggaccggga aagaaaaaca agaagaaaaa     660
cccggagaag ccccattttc ctctagcgac tgaagatgat gtcagacatc acttcacctc     720
tggtgagcgg caattgtgtc tgtcgtcaat ccagacagcc tttaatcaag gcgctggaac     780
ttgtaccctg tcagattcag ggaggataag ttacactgtg gagtttagtt tgccgacgca     840
tcatactgtg cgcctgatcc gcgtcacagc gtcaccctca gcatga                    886
```

*MYCOPLASMA HYOPNEUMONIAE* VACCINE

CROSS-REFERENCE TO RELATED APPLICATIONS

This application is a continuation of U.S. application Ser. No. 15/480,949, filed Apr. 6, 2017, now U.S. Pat. No. 10,206,991, which is a continuation of U.S. application Ser. No. 14/712,393, filed May 14, 2015, now U.S. Pat. No. 9,650,600, which is a divisional of U.S. application Ser. No. 13/850,318, filed Mar. 26, 2013, now U.S. Pat. No. 9,120,859, which claims the benefit of U.S. Provisional Application No. 61/620,165, filed Apr. 4, 2012, the contents each of which are incorporated herein by reference in their entirety.

FIELD OF THE INVENTION

The present invention relates to *Mycoplasma hyopneumoniae* (*M. hyopneumoniae* or M.hyo). More particularly, the invention relates to the soluble portion of an M.hyo whole cell preparation and its use in a vaccine for protecting pigs against enzootic pneumonia.

BACKGROUND OF THE INVENTION

Enzootic pneumonia in swine, also called mycoplasmal pneumonia, is caused by M.hyo. The disease is a chronic, non-fatal disease affecting pigs of all ages. Infected pigs show only mild symptoms of coughs and fever, but the disease has significant economic impact due to reduced feed efficiency and reduced weight gain. Enzootic pneumonia is transmitted from pig to pig through the nasal passages by airborne organisms expelled from the lungs of infected pigs. The primary infection by M.hyo may be followed by secondary infection by other *mycoplasma* species (*Mycoplasma hyorhinis* and *Mycoplasma flocculare*) as well as other bacterial pathogens.

M.hyo is a small, prokaryotic microbe capable of a free living existence, although it is often found in association with eukaryotic cells because it has absolute requirements for exogenous sterols and fatty acids. These requirements generally necessitate growth in serum-containing media. M.hyo is bounded by a cell membrane, but not a cell wall.

The physical association of mycoplasmas with the host cell surface is the basis for the development and persistence of enzootic pneumonia. M.hyo infects the respiratory tract of swine, colonizing the trachea, bronchi, and bronchioles. The *mycoplasma* produces a ciliostatic factor which causes the cilia lining the respiratory passages to stop beating. Eventually, the cilia degenerate, leaving the pig prone to infection by secondary pathogens. Characteristic lesions of purple to gray areas of consolidation are observed in infected animals. Surveys of slaughtered animals revealed lesions in 30 to 80% of swine. Results from 37 herds in 13 states indicated that 99% of the herds had hogs with pneumonia lesions typical of enzootic pneumonia. Therefore, the need for effective preventative and treatment measures are great.

Antibiotics such as tiamulin, trimethoprim, tetracyclines and lincomycin have some benefit, but are expensive and require prolonged use. Additionally, antibiotics have not been shown to effectively eliminate spread or reinfection of M.hyo. Prevention by maintaining pathogen-free herds is sometimes possible but reintroduction of M.hyo often occurs. Due to the serious economic consequences of swine pneumonia, vaccines against M.hyo have been sought. Vaccines containing preparations of mycoplasmal organisms grown in serum-containing medium have been marketed, but raise concerns regarding adverse reactions induced by serum components (such as immunocomplexes or non-immunogenic specific proteins) present in the immunizing material. Other attempts to provide M.hyo vaccines have been successful, but the disease remains widespread.

M.hyo and porcine circovirus type 2 (PCV2) are the two most prevalent pathogens that are encountered in the pig industry. Swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia. M.hyo is associated with enzootic pneumonia and has also been implicated as one of the major co-factors in the development of Porcine Circovirus Associated Disease (PCVAD).

Porcine reproductive and respiratory syndrome (PRRS) is caused by an arterivirus, which has a particular affinity for the macrophages particularly those found in the lung (alveolar macrophages). These macrophages ingest and remove invading bacteria and viruses, but not in the case of the PRRS virus. In the case of the PRRS virus, it multiplies inside the macrophages producing more virus and kills the macrophages. Once PRRSV has entered a herd, it tends to remain present and active indefinitely. Up to 40% of the macrophages are destroyed, which allows bacteria and other viruses to proliferate and do damage. A common example of this is the noticeable increase in severity of enzootic pneumonia in grower/finisher units when they become infected with PRRS virus. More than half of weaning-age PRRS virus-negative pigs become infected before going to market.

What is needed is an improved vaccine against *mycoplasma* infection in swine. Preferably, the M.hyo vaccine will be compatible with other porcine antigens, such as PCV2 and PRRS virus, whether they are given concurrently as separate single vaccines or combined in a ready-to-use vaccine. It would be highly desirable to provide a ready-to-use, single-dose M.hyo/PCV2 combination vaccine.

SUMMARY OF THE INVENTION

The present invention provides a protein-A or protein-G treated *Mycoplasma hyopneumoniae* (M.hyo) antigen that is compatible with antigens from other swine pathogens, wherein the M.hyo antigen is an M.hyo culture supernatant. In one embodiment, the M.hyo culture supernatant has been separated from insoluble cellular material by centrifugation, filtration, or precipitation and is substantially free of both (i) IgG and (ii) immunocomplexes comprised of antigen bound to immunoglobulin. In a further embodiment, the M.hyo antigen is inactivated.

The present invention further provides an immunogenic composition including the protein-A or protein-G treated *Mycoplasma hyopneumoniae* (M.hyo) antigen described above.

In some embodiments, the immunogenic composition of the present invention further includes at least one additional antigen. In one embodiment, the at least one additional antigen is protective against a microorganism that can cause disease in pigs.

In one embodiment, the swine pathogen includes bacteria, viruses, or protozoans. In another embodiment, the swine pathogen is selected from, but is not limited to, the following: porcine circovirus type 2 (PCV2), porcine reproductive and respiratory syndrome virus (PRRSV), porcine parvovirus (PPV), *Haemophilus parasuis, Pasteurella multocida, Streptococcum suis, Staphylococcus hyicus, Actinobacillus pleuropneumoniae, Bordetella bronchiseptica, Salmonella choleraesuis, Salmonella enteritidis, Erysipelothrix rhusiopathiae, Mycoplasma hyorhinis, Mycoplasma hyosynoviae*, leptospira bacteria, *Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Porcine enteroviruses, Encephalomyocarditis virus, a pathogen causative of Aujesky's Disease, Classical Swine fever (CSF) and a pathogen causative of Swine Transmissible Gastroenteritis, or combinations thereof.

In certain embodiments, the at least one additional antigen is a porcine circovirus type 2 (PCV2) antigen, a PRRS virus antigen, a *Lawsonia intracellularis* antigen or a combination thereof. In one embodiment, the composition elicits a protective immune response against M.hyo and PCV2. In another embodiment, the composition elicits a protective immune response against M.hyo, PCV2 and PRRS virus. In yet another embodiment, the composition elicits a protective immune response in a pig against M.hyo, PCV2 and *Lawsonia intracellularis*.

In one embodiment, the PCV2 antigen is in the form of a chimeric type-1-type 2 circovirus, the chimeric virus including an inactivated recombinant porcine circovirus type 1 expressing the porcine circovirus type 2 ORF2 protein. In another embodiment, the PCV2 antigen is in the form of a recombinant ORF2 protein. In still another embodiment, the recombinant ORF2 protein is expressed from a baculovirus vector.

In some embodiments, the composition of the present invention further includes an adjuvant. In one embodiment, the adjuvant is selected from, but is not limited to, the following: an oil-in-water adjuvant, a polymer and water adjuvant, a water-in-oil adjuvant, an aluminum hydroxide adjuvant, a vitamin E adjuvant and combinations thereof. In another embodiment, the composition of the present invention further includes a pharmaceutically acceptable carrier.

In certain embodiments, the composition of the present invention elicits a protective immune response against M.hyo when administered as a single dose administration. In further embodiments, the composition elicits a protective immune response against M.hyo and the at least one additional swine pathogen (microorganism) when administered as a single dose administration. In still further embodiments, a composition of the present invention elicits a protective response against M.hyo and the at least one additional swine pathogen when administered as a two dose administration.

The present invention also provides a method of immunizing a pig against M.hyo. This method includes administering to the pig an immunogenic composition including a protein-A or protein-G treated *Mycoplasma hyopneumoniae* (M.hyo) antigen that is compatible with antigens from other swine pathogens, wherein the M.hyo antigen is an M.hyo culture supernatant. In one embodiment of the method of the present invention, the composition is administered intramuscularly, intradermally, transdermally, or subcutaneously. In another embodiment of the method of this invention, the composition is administered in a single dose. In yet another embodiment of the method of this invention, the composition is administered as two doses.

In a further embodiment of the method of the present invention, the composition is administered in conjunction with at least one additional antigen that is protective against a swine pathogen, such as one or more of the microorganisms described above. Such other antigens can be given concurrently with the M.hyo composition (i.e., as separate single vaccines) or combined in a ready-to-use vaccine.

In a further embodiment, the composition is administered to pigs having maternally derived antibodies against M.hyo. In a still further embodiment, the composition is administered to pigs having maternally derived antibodies against M.hyo and the at least one other swine pathogen.

In one embodiment, the composition is administered to pigs at 3 weeks of age or older.

The present invention further provides a kit. This kit includes a protein-A or protein-G treated *Mycoplasma hyopneumoniae* (M.hyo) antigen that is compatible with antigens from other swine pathogens, wherein the M.hyo antigen is an M.hyo culture supernatant. In one embodiment, this M.hyo culture supernatant has been separated from insoluble cellular material by centrifugation, filtration, or precipitation and is substantially free of both (i) IgG and (ii) immunocomplexes comprised of antigen bound to immunoglobulin.

In one embodiment, the kit further includes at least one additional antigen that is protective against a swine pathogen selected from the group consisting of porcine circovirus type 2 (PCV2), porcine reproductive and respiratory syndrome virus (PRRSV), porcine parvovirus (PPV), *Haemophilus parasuis, Pasteurella multocida, Streptococcum suis, Staphylococcus hyicus, Actinobacillus pleuropneumoniae, Bordetella bronchiseptica, Salmonella choleraesuis, Salmonella enteritidis, Erysipelothrix rhusiopathiae, Mycoplasma hyorhinis, Mycoplasma hyosynoviae*, leptospira bacteria, *Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Porcine enteroviruses, Encephalomyocarditis virus, a pathogen causative of Aujesky's Disease, Classical Swine fever (CSF) and a pathogen causative of Swine Transmissible Gastroenteritis, or combinations thereof.

In one specific embodiment of the kit, the at least one additional antigen is a porcine circovirus type 2 (PCV2) antigen, a PRRS virus antigen, a *Lawsonia intracellularis* antigen or a combination thereof.

BRIEF DESCRIPTION OF THE DRAWINGS

FIG. 10 is a table showing the adjuvant evaluation for virucidal activity against PRRS virus.

BRIEF DESCRIPTION OF THE SEQUENCES

Figure 1:
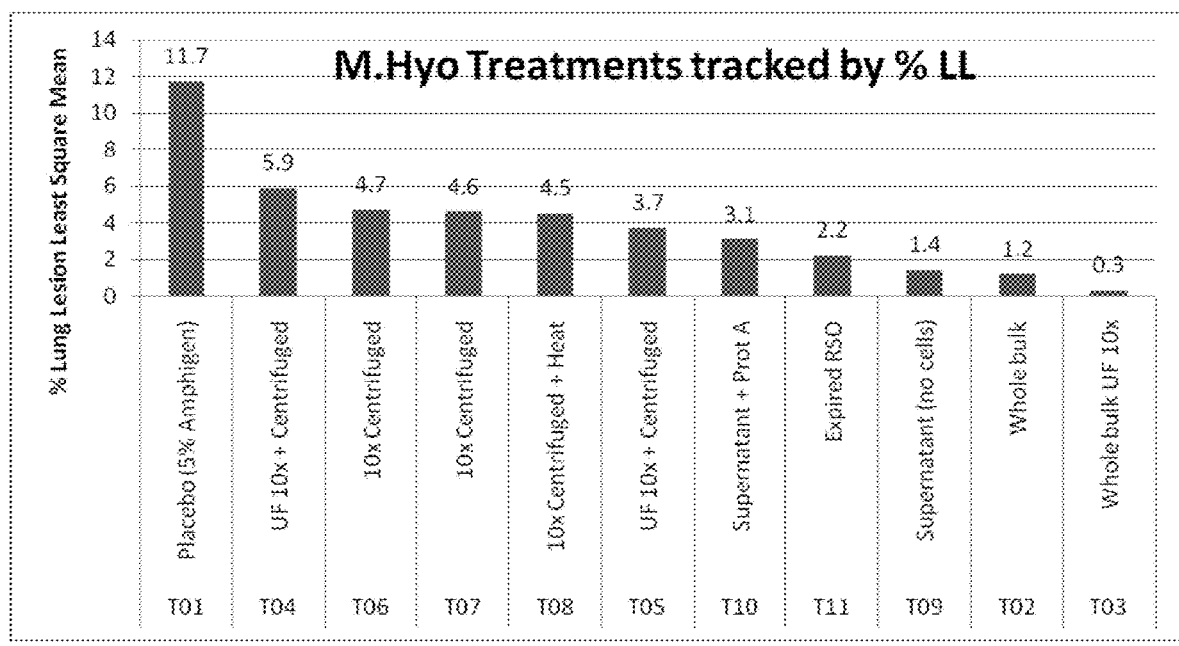
FIG. 1 is a graph showing the efficacy of M.hyo monovalent vaccines prepared with M.hyo antigens from different treatments (T02-T10 described in Example 3) vs. a placebo (T01). The results are presented as % Lung Lesion Least Square Mean values.

SEQ ID NO: 1 is one embodiment of a nucleotide sequence encoding p46 from the P-5722 strain of M.hyo;

SEQ ID NO: 2 is one embodiment of an amino acid sequence corresponding to p46 from the P-5722 strain of M.hyo;

SEQ ID NO: 3 is one embodiment of a nucleotide sequence encoding p97 from the P-5722 strain of M.hyo;

SEQ ID NO: 4 is one embodiment of an amino acid sequence corresponding to p97 from the P-5722 strain of M.hyo;

SEQ ID NO: 5 is one embodiment of a genomic sequence encoding a chimeric PCV1-2 virus;

SEQ ID NO: 6 is one embodiment of a nucleotide sequence corresponding to ORF2 of a porcine circovirus;

SEQ ID NO: 7 is one embodiment of an amino acid sequence corresponding to the ORF2 polypeptide of a porcine circovirus;

SEQ ID NO: 8 is one embodiment of a genomic sequence encoding a chimeric PCV1-2 virus;

SEQ ID NO: 9 is one embodiment of a nucleotide sequence corresponding to ORF2 of a porcine circovirus;

SEQ ID NO: 10 is one embodiment of an amino acid sequence corresponding to the ORF2 polypeptide of a porcine circovirus;

SEQ ID NO: 11 is one embodiment of an amino acid sequence corresponding to the ORF2 polypeptide of a porcine circovirus;

SEQ ID NO: 12 is one embodiment of a nucleotide sequence encoding the amino acid sequence of SEQ ID NO: 11;

SEQ ID NO: 13 is one embodiment of an amino acid sequence corresponding to the ORF2 polypeptide of a porcine circovirus;

SEQ ID NO: 14 is one embodiment of a nucleotide sequence encoding the amino acid sequence of SEQ ID NO: 13;

SEQ ID NO: 15 is one embodiment of an amino acid sequence corresponding to the ORF2 polypeptide of a porcine circovirus;

SEQ ID NO: 16 is one embodiment of a genomic sequence of a non-virulent form of the North American PRRS virus isolate designated P129; and SEQ ID NO: 17 is one embodiment of a nucleotide sequence corresponding to ORF2 to ORF5 of the PRRS virus isolate designated ISU-55.

SEQ ID NO: 18 is one embodiment of a nucleotide sequence corresponding to ORF6 and ORF7 of the PRRS virus isolate designated ISU-55.

DETAILED DESCRIPTION OF THE INVENTION

The present invention provides a protein-A or protein-G treated *Mycoplasma hyopneumoniae* (M.hyo) antigen that is compatible with antigens from other swine pathogens, wherein the M.hyo antigen is an M.hyo culture supernatant. The present invention further provides immunogenic compositions including the protein-A or protein-G treated *Mycoplasma hyopneumoniae* (M.hyo) antigen, as well as methods of immunizing a pig against at least M.hyo by administering these immunogenic compositions. The M.hyo culture supernatant has been separated from insoluble cellular material and is substantially free of both (i) IgG and (ii) immunocomplexes comprised of antigen bound to immunoglobulin. The M.hyo supernatant may be alternatively referred to herein as the soluble portion of an M.hyo whole cell preparation.

Applicants have surprisingly discovered that the insoluble fraction of the M.hyo whole cell preparation is non-immunogenic. In contrast, the IgG-free M.hyo soluble preparation is immunogenic and can be effectively combined with antigens from other pathogens, such as PCV2, without analytical or immunological interference between the antigens. This makes the M.hyo soluble preparation of this invention an effective platform for multivalent vaccines, including one-bottle, ready-to-use formulations. Applicants have also surprisingly discovered that removing the immunoglobulin and the insoluble cell debris enhances the safety of the immunogenic composition.

As used in the specification and claims, the singular form "a", "an" and "the" include plural references unless the context clearly dictates otherwise. For example, the term "a protein antigen" includes a plurality of protein antigens, including mixtures thereof.

As used herein, the term "comprising" is intended to mean that the compositions and methods include the recited elements, but do not exclude other elements.

As defined herein, a soluble portion of an M.hyo whole cell preparation refers to a soluble liquid fraction of an M.hyo whole cell preparation after separation of the insoluble material and substantial removal of IgG and antigen-bound immunocomplexes. The M.hyo soluble portion may alternatively be referred to herein as the supernatant fraction, culture supernatant and the like. It includes M.hyo-expressed soluble proteins (M.hyo protein antigens) that have been separated or isolated from insoluble proteins, whole bacteria, and other insoluble M.hyo cellular material by conventional means, such as centrifugation, filtration, or precipitation. In addition to including M.hyo-specific soluble proteins, the soluble portion of the M.hyo whole cell preparation also includes heterologous proteins, such as those contained in the culture medium used for M.hyo fermentation.

The term "antigen" refers to a compound, composition, or immunogenic substance that can stimulate the production of antibodies or a T-cell response, or both, in an animal, including compositions that are injected or absorbed into an animal. The immune response may be generated to the whole molecule, or to a portion of the molecule (e.g., an epitope or hapten).

As defined herein, an "immunogenic or immunological composition", refers to a composition of matter that comprises at least one antigen which elicits an immunological response in the host of a cellular and or antibody-mediated immune response to the composition or vaccine of interest.

The term "immune response" as used herein refers to a response elicited in an animal. An immune response may refer to cellular immunity (CMI); humoral immunity or may involve both. The present invention also contemplates a response limited to a part of the immune system. Usually, an "immunological response" includes, but is not limited to, one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term "immunogenicity" means capable of producing an immune response in a host animal against an antigen or antigens. This immune response forms the basis of the protective immunity elicited by a vaccine against a specific infectious organism.

An "adjuvant" as used herein means a composition comprised of one or more substances that enhances the immune response to an antigen(s). The mechanism of how an adjuvant operates is not entirely known. Some adjuvants are believed to enhance the immune response by slowly releasing the antigen, while other adjuvants are strongly immunogenic in their own right and are believed to function synergistically.

As used herein, the term "multivalent" means a vaccine containing more than one antigen whether from the same species (i.e., different isolates of *Mycoplasma hyopneumoniae*), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

The term "pig" or "piglet" as used herein means an animal of porcine origin, while "sow" refers to a female of reproductive age and capability. A "gilt" is a female pig who has never been pregnant.

As used herein, the term "virulent" means an isolate that retains its ability to be infectious in an animal host.

"Inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with thimerosal or formalin), sonication, radiation, heat or any other convention means sufficient to prevent replication or growth of the organism while maintaining its immunogenicity.

The term "variant" as used herein refers to a polypeptide or a nucleic acid sequence encoding a polypeptide, that has one or more conservative amino acid variations or other minor modifications such that the corresponding polypeptide has substantially equivalent function when compared to the wild-type polypeptide.

"Conservative variation" denotes the replacement of an amino acid residue by another biologically similar residue, or the replacement of a nucleotide in a nucleic acid sequence such that the encoded amino acid residue does not change or is another biologically similar residue. Examples of conservative variations include the substitution of one hydrophobic residue, such as isoleucine, valine, leucine or methionine for another hydrophobic residue, or the substitution of one polar residue, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, transdermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

"North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117-126); North American PRRS virus isolate MN-1b (Kwang, J. et al., 1994, J. Vet. Diagn. Invest. 6:293-296); the Quebec LAF-exp91 strain of PRRS virus (Mardassi, H. et al., 1995, Arch. Virol. 140:1405-1418); and North American PRRS virus isolate VR 2385 (Meng, X.-J et al., 1994, J. Gen. Virol. 75:1795-1801). Additional examples of North American PRRS virus strains are described herein. Genetic characteristics refer to genomic nucleotide sequence similarity and amino acid sequence similarity shared by North American PRRS virus strains. Chinese PRRS virus strains generally evidence about 80-93% nucleotide sequence similarity with North American strains.

"European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus". Further examples of European PRRS virus strains are described herein.

A genetically modified virus is "attenuated" if it is less virulent than its unmodified parental strain. A strain is "less virulent" if it shows a statistically significant decrease in one or more parameters determining disease severity. Such parameters may include level of viremia, fever, severity of respiratory distress, severity of reproductive symptoms, or number or severity of lung lesions, etc.

An "Infectious clone" is an isolated or cloned genome of the disease agent (e.g. viruses) that can be specifically and purposefully modified in the laboratory and then used to re-create the live genetically modified organism. A live genetically modified virus produced from the infectious clone can be employed in a live viral vaccine. Alternatively, inactivated virus vaccines can be prepared by treating the live virus derived from the infectious clone with inactivating agents such as formalin or hydrophobic solvents, acids, etc., by irradiation with ultraviolet light or X-rays, by heating, etc.

All currently available M.hyo vaccines are made from killed whole cell *mycoplasma* preparations (bacterins). In contrast, the present invention employs a soluble portion of a *Mycoplasma hyopneumoniae* (M.hyo) whole cell preparation, wherein the soluble portion of the M.hyo preparation is substantially free of both (i) IgG and (ii) immunocomplexes comprised of antigen bound to immunoglobulin.

M.hyo has absolute requirements for exogenous sterols and fatty acids. These requirements generally necessitate growth of M.hyo in serum-containing media, such as porcine serum. Separation of the insoluble material from the soluble portion of the M.hyo whole cell preparation (e.g., by centrifugation, filtration, or precipitation) does not remove the porcine IgG or immune complexes. In one embodiment of the present invention, the M.hyo soluble portion is treated with protein-A or protein-G in order to substantially remove the IgG and immune complexes contained in the culture supernatant. In this embodiment, it is understood that protein A treatment occurs post-M.hyo fermentation. This is alternatively referred to herein as downstream protein A treatment. In another embodiment, upstream protein A treatment of the growth media (i.e., before M.hyo fermentation) can be employed. Protein A binds to the Fc portion of IgG. Protein G binds preferentially to the Fc portion of IgG, but can also bind to the Fab region. Methods for purifying/removing total IgG from crude protein mixtures, such as tissue culture supernatant, serum and ascites fluid are known in the art.

In some embodiments, the soluble portion of the M.hyo preparation includes at least one M.hyo protein antigen. In other embodiments, the soluble portion of the M.hyo preparation includes two or more M.hyo protein antigens.

In one embodiment, the M.hyo supernatant fraction includes one or more of the following M.hyo specific protein antigens: M.hyo proteins of approximately 46 kD (p46), 64 kD (p64) and 97 kD (p97) molecular weights. In another embodiment, the supernatant fraction at least includes the p46, p64 and p97 M.hyo protein antigens. The M.hyo protein of approximately 64 kD (p64) may be alternatively referred to herein as the p65 surface antigen from M.hyo described by Kim et al. [Infect. Immun. 58(8):2637-2643 (1990)], as well as in U.S. Pat. No. 5,788,962.

Futo et al. described the cloning and characterization of a 46 kD surface protein from M.hyo, which can be employed in the compositions of this invention [J. Bact 177: 1915-1917 (1995)]. In one embodiment, the M.hyo culture supernatant includes the p46 whose corresponding nucleotide and amino acid sequences from the P-5722 strain are set forth in SEQ ID NOs: 1 and 2, respectively. It is further contemplated that variants of such p46 sequences can be employed in the compositions of the present invention, as described below.

Zhang et al. described and characterized a p97 adhesin protein of M.hyo [Infect. Immun. 63: 1013-1019, 1995]. Additionally, King et al. described a 124 kD protein termed Mhp1 from the P-5722 strain of M.hyo and presented data suggesting that Mhp1 and p97 are the same protein [Vaccine 15:25-35 (1997)]. Such p97 proteins can be employed in the compositions of this invention. In one embodiment, the M.hyo culture supernatant includes the p97 whose corresponding nucleotide and amino acid sequences from the P-5722 strain are set forth in SEQ ID NOs: 3 and 4, respectively. It is further contemplated that variants of such p97 sequences can be employed in the compositions of the present invention, as described below.

The M.hyo culture supernatant may include further M.hyo specific protein antigens such as, but not limited to, proteins of approximately 41 kD (p41), 42 kD (p42), 89 kD (p89), and 65 kD (p65). See, Okada et al., 2000, J. Vet. Med. B 47:527-533 and Kim et al., 1990, Infect. Immun. 58(8): 2637-2643. In addition, the M.hyo culture supernatant can include M.hyo specific protein antigens of approximately 102 kD (p102) and 216 kD (p216). See, U.S. Pat. Nos. 6,162,435 and 7,419,806 to Minnion et al.

Any M.hyo strain may be used as a starting material to produce the soluble portion of the M.hyo preparation of the present invention. Suitable strains of M.hyo may be obtained from commercial or academic sources, including depositories such as the American Type Culture Collection (ATCC) (Manassas, Va.) and the NRRL Culture Collection (Agricultural Research Service, U.S. Department of Agriculture, Peoria, Ill.). The ATCC alone lists the following six strains of M.hyo for sale: M.hyo ATCC 25095, M.hyo ATCC 25617, M.hyo ATCC 25934, M.hyo ATCC 27714, M.hyo ATCC 27715, and M.hyo ATCC 25934D. A preferred strain of M.hyo for use in the embodiments of this invention is identified as strain P-5722-3, ATCC #55052, deposited on May 30, 1990 pursuant to the accessibility rules required by the U.S. Patent and Trademark Office. In view of the widespread dissemination of the disease, strains may also be obtained by recovering M.hyo from lung secretions or tissue from swine infected with known strains causing mycoplasmal pneumonia in swine.

It is understood by those of skill in the art that variants of the M.hyo sequences can be employed in the compositions of the present invention. Such variants could vary by as much as 10-20% in sequence identity and still retain the antigenic characteristics that render it useful in immunogenic compositions. Preferably, the M.hyo variants have at least 80%, preferably at least 85%, more preferably at least 90%, even more preferably at least 95% sequence identify with the full-length genomic sequence of the wild-type M.hyo strain. The antigenic characteristics of an immunological composition can be, for example, estimated by the challenge experiment as provided in the Examples. Moreover, the antigenic characteristic of a modified M.hyo antigen is still retained when the modified antigen confers at least 70%, preferably 80%, more preferably 90% of the protective immunity as compared to the wild-type M.hyo protein.

In one embodiment, M.hyo soluble p46 antigen is included in the compositions of the invention at a final concentration of about 1.5 µg/ml to about 10 µg/ml, preferably at about 2 µg/ml to about 6 µg/ml. It is noted that p46 is the protein used for the M.hyo potency test (see example section below). In another embodiment, the M.hyo antigen can be included in the compositions at a final amount of about 5.5% to about 35% of the M.hyo whole culture protein A-treated supernatant.

The M.hyo soluble preparation of the present invention is both safe and efficacious against M.hyo and is suitable for single dose administration. In addition, Applicants have surprisingly discovered that the M.hyo soluble preparation can be effectively combined with antigens from other pathogens without immunological interference between the antigens. This makes the M.hyo soluble preparation of this invention an effective platform for multivalent vaccines. The additional antigens may be given concurrently with the M.hyo composition (i.e., as separate single vaccines) or combined in a ready-to-use vaccine.

In one embodiment, the immunogenic composition of the present invention includes at least one M.hyo soluble antigen and at least one additional antigen. In one embodiment, the at least one additional antigen is protective against a microorganism that can cause disease in pigs.

In some embodiments, the at least one additional antigen component is protective against bacteria, viruses, or protozoans that are known to infect pigs. Examples of such microorganisms include, but are not limited to, the following: porcine circovirus type 2 (PCV2), porcine reproductive and respiratory syndrome virus (PRRSV), porcine parvovirus (PPV), *Haemophilus parasuis, Pasteurella multocida, Streptococcum suis, Staphylococcus hyicus, Actinobacillus pleuropneumoniae, Bordetella bronchiseptica, Salmonella choleraesuis, Salmonella enteritidis, Erysipelothrix rhusiopathiae, Mycoplasma hyorhinis, Mycoplasma hyosynoviae,* leptospira bacteria, *Lawsonia intracellularis,* swine influenza virus (SIV), *Escherichia coli* antigen, *Brachyspira hyodysenteriae,* porcine respiratory coronavirus, Porcine Epidemic Diarrhea (PED) virus, rotavirus, Torque teno virus (TTV), Porcine Cytomegalovirus, Porcine enteroviruses, Encephalomyocarditis virus, a pathogen causative of Aujesky's Disease, Classical Swine fever (CSF) and a pathogen causative of Swine Transmissible Gastroenteritis, or combinations thereof.

In one embodiment, an immunogenic composition of the present invention includes the combination of at least one M.hyo soluble antigen (e.g., two or more) and a PCV2 antigen. In another embodiment, the composition elicits a protective immune response in a pig against both M.hyo and PCV2.

In one embodiment, an M.hyo/PCV2 combination vaccine according to the present invention is provided as a single-dose, ready-to-use in one bottle vaccine. Such a ready-to-use combination vaccine requires no mixing of separate vaccines, so there is no risk of contamination or additional labor associated with mixing and no requirement to use the mixture within a few hours. Also, a one-bottle M.hyo/PCV2 combination vaccine cuts waste and refrigerator storage space in half. Furthermore, one-dose administration eliminates the labor associated with administering a second dose to the animal. It is noted that although PCV2/M.hyo combination vaccines currently exist, they are provided as either a two-dose, ready-to-use vaccine (Circumvent® PCVM) or as a single-dose, 2-bottle vaccine which requires the simultaneous administration of separate vaccines (e.g., Ingelvac CircoFLEX® and Ingelvac MycoFLEX®). Preferably, the M.hyo/PCV2 combination according to the present invention would be compatible with other antigens, such as PRRS virus antigens, such that all antigens can be administered in a single-dose.

In some embodiments, the PCV2 antigen component of an M.hyo/PCV2 combination vaccine is in the form of a chimeric type-1-type 2 circovirus. The chimeric virus includes an inactivated recombinant porcine circovirus type 1 expressing the porcine circovirus type 2 ORF2 protein. Chimeric porcine circoviruses and methods for their preparation are described in WO 03/049703 A2, and also in U.S. Pat. Nos. 7,279,166 and 7,575,752, which are incorporated herein by reference in their entirety.

In one embodiment, the full-length DNA sequence of the genome of the chimeric PCV1-2 virus corresponds to SEQ ID NO: 5. or variants thereof, as described below. In another embodiment, the immunogenic ORF2 capsid gene of the chimeric PCV1-2 virus corresponds to SEQ ID NO: 6. In a further embodiment, the amino acid sequence of the immunogenic ORF2 protein expressed by the chimeric PCV1-2 virus corresponds to SEQ ID NO: 7.

In yet another embodiment, the full-length DNA sequence of the genome of the chimeric PCV1-2 virus corresponds to SEQ ID NO: 8. In one embodiment, the immunogenic ORF2 capsid gene of the chimeric PCV1-2 virus corresponds to SEQ ID NO: 9. In a further embodiment, the amino acid sequence of the immunogenic ORF2 protein expressed by the chimeric PCV1-2 virus corresponds to SEQ ID NO: 10.

However, the PCV2 ORF2 DNA and protein of the chimeric PCV1-2 virus are not limited to the sequences described above since PCV2 ORF2 DNA and protein is a highly conserved domain within PCV2 isolates.

In some embodiments, the PCV2 antigen component of an M.hyo/PCV2 combination vaccine is in the form of a recombinant ORF2 protein. In one embodiment, the recombinant ORF2 protein is expressed from a baculovirus vector. Alternatively, other known expression vectors can be used, such as including, but not limited to, parapox vectors.

In one embodiment, the recombinant PCV2 ORF2 protein is that of SEQ ID NO: 11, which is encoded by SEQ ID NO: 12 (GenBank Accession No. AF086834). In another embodiment, the recombinant ORF2 protein is that of SEQ ID NO: 13, which is encoded by SEQ ID NO: 14. In yet another embodiment, the recombinant ORF2 protein corresponds to SEQ ID NO: 15. In still another embodiment, the recombinant PCV2 ORF2 protein corresponds to SEQ ID NO: 7. In a still further embodiment, the recombinant PCV2 ORF2 protein corresponds to SEQ ID NO: 10.

However, the present invention is not limited to the particular ORF2 DNA and protein sequences described above. Since PCV2 ORF2 DNA and protein is a highly conserved domain within PCV2 isolates, any PCV2 ORF2 is highly likely to be effective as the source of the PCV2 ORF2 DNA and/or polypeptide as used in the chimeric PCV1-2 virus or in the recombinant PCV2 protein.

An example of a suitable PCV2 isolate from which the PCV2 ORF2 DNA and protein sequences can be derived is PCV2 isolate number 40895 (deposited in the ATCC on Dec. 7, 2001 and assigned ATCC Patent Deposit Designation PTA-3914). The genomic (nucleotide) sequence of the PCV2 isolate number 40895 is available under GenBank accession number AF264042. Other examples of suitable PCV2 isolates from which the PCV2 ORF2 DNA and protein sequences can be derived include, but are not limited to, the following: Imp.999, Imp.1010-Stoon, Imp.1011-48121, and Imp.1011-48285. The GenBank accession numbers of the genomic sequences corresponding to these PCV2 isolates are AF055391, AF055392, AF055393 and AF055394, respectively.

In some forms, immunogenic portions of PCV2 ORF2 protein are used as the antigenic component in the composition. For example, truncated and/or substituted forms or fragments of PCV2 ORF2 protein may be employed in the compositions of the present invention.

It is understood by those of skill in the art that variants of the PCV2 sequences can be employed in the compositions of the present invention. Such variants could vary by as much as 10-20% in sequence identity and still retain the antigenic characteristics that render it useful in immunogenic compositions. Preferably, the PCV2 variants have at least 80%, preferably at least 85%, more preferably at least 90%, even more preferably at least 95% sequence identify with the full-length genomic sequence of the wild-type PCV2 isolate. The antigenic characteristics of an immunological composition can be, for example, estimated by the challenge experiment as provided in the Examples. Moreover, the antigenic characteristic of a modified PCV2 antigen is still retained when the modified antigen confers at least 70%, preferably 80%, more preferably 90% of the protective immunity as compared to the wild-type PCV2 ORF2 protein.

The PCV2 antigen component is provided in the immunogenic composition at an antigen inclusion level effective for inducing the desired immune response, namely reducing the incidence of or lessening the severity of clinical signs resulting from PCV2 infection.

In one embodiment, a chimeric PCV1-2 virus is included in the compositions of the invention at a level of at least $1.0 \le RP \le 5.0$, wherein RP is the Relative Potency unit determined by ELISA antigen quantification (in vitro potency test) compared to a reference vaccine. In another embodiment, a chimeric PCV1-2 virus is included in the composition of the invention at a final concentration of about 0.5% to about 5% of 20-times (20×) concentrated bulk PCV1-2 antigen.

In another embodiment, the PCV2 ORF2 recombinant protein is included in the compositions of the invention at a level of at least 0.2 μg antigen/ml of the final immunogenic composition (μg/ml). In a further embodiment, the PCV2 ORF2 recombinant protein inclusion level is from about 0.2 to about 400 μg/ml. In yet another embodiment, the PCV2 ORF2 recombinant protein inclusion level is from about 0.3 to about 200 μg/ml. In a still further embodiment, the PCV2 ORF2 recombinant protein inclusion level is from about 0.35 to about 100 μg/ml. In still another embodiment, the PCV2 ORF2 recombinant protein inclusion level is from about 0.4 to about 50 μg/ml.

In one embodiment, an immunogenic composition of the present invention includes the combination of at least one M.hyo soluble antigen (e.g., two or more), a porcine circovirus type 2 (PCV2) antigen, and a PRRS virus antigen. In another embodiment, the composition elicits a protective immune response in a pig against M.hyo, PCV2 and PRRS virus.

In one embodiment, an M.hyo/PCV2/PRRS combination vaccine according to the present invention is provided as a single-dose, 2-bottle vaccine. For example, in some embodiments, a M.hyo/PCV2 combination is provided as a stable liquid composition in a first bottle and a PRRS virus is provided in a lyophilized state in a second bottle. In some embodiments, additional porcine antigens can be added to either the first or the second bottle.

In one embodiment, the PRRS virus component is provided as a lyophilized, genetically modified live virus. Prior to administration, the M.hyo/PCV2 liquid from a first bottle can be used to re-hydrate the PRRS virus in a second bottle so that all three antigens can be administered to the animal in a single-dose. It is noted that although PCV2/M.hyo/PRRS combination vaccines currently exist, they are provided as a single-dose, 3-bottle vaccine which requires the simultaneous administration of three separate vaccines (e.g., Ingelvac CircoFLEX®, Ingelvac MycoFLEX® and Ingelvac® PRRS MLV).

The PRRS etiological agent was isolated for the first time in The Netherlands, and named as Lelystad virus. This virus was described in WO 92/21375 (Stichting Centraal Diegeneeskundig Instituut). An isolate of the European PRRS virus was deposited in the Institut Pasteur of Paris, number I-1102. The North American type was isolated almost simultaneously with the isolation of the European type virus, and is described in WO-93/03760 (Collins et al.) An isolate of the North American type virus was deposited in the American Type Culture Collection (ATCC), number VR-2332.

Different strains have been isolated from both the European and North American virus types. WO 93/07898 (Akzo) describes a European strain, and vaccines derived from it, deposited in CNCM (Institut Pasteur), number 1-1140. Also, WO 93/14196 (Rhone-Merieux) describes a new strain isolated in France, deposited in CNCM (Institut Pasteur), number 1-1153. Furthermore, EP0595436 B1(Solvay) describes a new North American type strain, more virulent than the one initially described, and vaccines thereof. This strain has been deposited in ATCC, but the deposit number is not detailed in the patent application. In addition, ES2074950 BA (Cyanamid Iberica) and its counterpart GB2282811 B2 describe a so-called "Spanish strain", that is different from other European and North American strains. This "Spanish strain" has been deposited in European Animal Cell Culture Collection (EACCC), number V93070108.

Suitable PRRS virus antigens for use in the M.hyo/PCV2/PRRS compositions of the present invention include North American PRRS virus isolates, Chinese PRRS virus strains, and European PRRS virus strains, as well as genetically modified versions of such isolates/strains. In one embodiment, the PRRS virus antigen component employed in the compositions according to the present invention is a North American PRRS virus.

In some embodiments, the PRRS virus antigen component employed in the compositions of this invention is the North American PRRS virus isolate designated P129 or a live, genetically modified version thereof. Preferably, the genetically modified PRRS virus is unable to produce a pathogenic infection yet is able to elicit an effective immunoprotective response against infection by the wild-type PRRS virus.

A genetically modified PRRS virus for use in the compositions of the invention can be produced from an infectious clone. The preparation of an infectious cDNA clone of the North American PRRS virus isolate designated P129 is described in U.S. Pat. No. 6,500,662 which is hereby incorporated fully by reference. The sequence of P129 cDNA is disclosed in Genbank Accession Number AF494042 and in U.S. Pat. No. 6,500,662.

In one embodiment, the nucleotide sequence of a non-virulent form of P129 for use in the compositions of the present invention is represented by SEQ ID NO: 16. However, the present invention is not limited to this sequence. This sequence and the sequences of other non-virulent forms of P129 are described in International Application No. PCT/IB2011/055003, filed Nov. 9, 2011, the contents of which (including any US National Stage filings based on this International Application) are incorporated herein by reference in their entirety. Preferably, the PRRS virus is modified to prevent downregulation of interferon-mediated function.

In other embodiments, the PRRS virus antigen component employed in the compositions of the invention is the PRRS virus isolate designated ISU-55. The ISU-55 isolate was deposited in the American Type Culture Collection (ATCC), under the accession number VR2430. The nucleotide sequence of the ORF2 to ORF5 genes of the ISU-55 isolate is represented by SEQ ID NO:17. The nucleotide sequence of the ORF6 and ORF7 genes of the ISU-55 isolate is represented by SEQ ID NO: 18.

Another suitable North American PRRS virus isolate which can be used in the compositions is ISU-12, which was deposited in the ATCC under the accession numbers VR2385 [3× plaque purified] and VR2386 [non-plaque purified]. Still other suitable North American PRRS virus isolates which can be employed in the compositions of this invention are the following: ISU-51, ISU-3927, ISU-1894, ISU-22 and ISU-79, which were deposited in the ATCC under the accession numbers VR2498, VR2431, VR2475, VR2429 and VR2474, respectively. Genetically modified versions of any of these ISU isolates can be employed in the compositions of this invention. These ISU isolates and the ISU-55 isolate are described in detail in the following U.S. patents to Paul, et al: U.S. Pat. Nos. 5,695,766, 6,110,467, 6,251,397, 6,251,404, 6,380,376, 6,592,873, 6,773,908, 6,977,078, 7,223,854, 7,264,802, 7,264,957, and 7,517,976, all of which are incorporated herein by reference in their entirety.

In still other embodiments, the PRRS virus antigen component employed in the compositions according to the present invention is the North American type deposited in the American Type Culture Collection (ATCC), number VR-2332 or a genetically modified version thereof. For example, the PRRS virus can be a modified live virus based on the isolate identified as ATCC VR2332, which is employed in INGELVAC® PRRS ATP and INGELVAC® PRRS MLV, from Boehringer Ingelheim Vetmedica, Inc.

In still other embodiments, the PRRS virus antigen component employed in the compositions of the present invention is a European PRRS virus isolate or Lelystad virus or a genetically modified version thereof. An example of a suitable PRRS virus strain is identified as deposit No. I-1102, described above. Nucleotide and amino acid sequences corresponding to the I-1102 deposit are described in U.S. Pat. No. 5,620,691 to Wensvoort et al, which is hereby fully incorporated herein by reference. The preparation of an infectious clone of a European PRRS virus isolate or Lelystad virus is described in U.S. Pat. No. 6,268,199 which is hereby fully incorporated herein by reference.

Other examples of suitable PRRS virus isolates include, but are not limited to, those described above. Also, live, genetically modified versions of the PRRS virus isolates can be employed in the compositions of the present invention. An infectious clone can be used to re-create such live genetically modified organisms.

It is understood by those of skill in the art that variants of the PRRS virus sequences can be employed in the compositions of the present invention. Such variants could vary by as much as 10-20% in sequence identity and still retain the antigenic characteristics that render it useful in immunogenic compositions. Preferably, the PRRS virus variants have at least 80%, preferably at least 85%, more preferably at least 90%, even more preferably at least 95% sequence identify with the full-length genomic sequence of the wild-type PPRS virus isolate. The antigenic characteristics of an immunological composition can be, for example, estimated by challenge experiments. Moreover, the antigenic characteristic of a modified PRRS virus antigen is still retained when the modified antigen confers at least 70%, preferably 80%, more preferably 90% of the protective immunity as compared to the wild-type PRRS virus antigen.

In one embodiment, the PRRS virus antigen component is a genetically modified, live virus which is included in the compositions of the invention at a level of at least $2.1 \leq TCID_{50} \leq 5.2$, wherein $TCID_{50}$ is the tissue culture infectious dose 50% determined by antigen quantification (in vitro potency test).

The PCV2 antigen component of the M.hyo/PCV2/PRRS compositions of the invention can be in the form of a chimeric type-1-type 2 circovirus, the chimeric virus including an inactivated recombinant porcine circovirus type 1 expressing the porcine circovirus type 2 ORF2 protein. In another embodiment, the PCV2 antigen component of the M.hyo/PCV2/PRRS compositions of the invention is in the form of a recombinant ORF2 protein.

Suitable PCV2 antigens for use in the M.hyo/PCV2/PRRS compositions can be derived from any of the PCV2 isolates described above, as well as other PCV2 isolates. Suitable PCV2 antigens to be employed in the compositions of the invention include, but are not limited to, the PCV2 sequences described above and variants thereof.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Types of suitable adjuvants for use in the compositions of the present invention include the following: an oil-in-water adjuvant, a polymer and water adjuvant, a water-in-oil adjuvant, an aluminum hydroxide adjuvant, a vitamin E adjuvant and combinations thereof. Some specific examples of adjuvants include, but are not limited to, complete Freund's adjuvant, incomplete Freund's adjuvant, *Corynebacterium parvum, Bacillus* Calmette Guerin, aluminum hydroxide gel, glucan, dextran sulfate, iron oxide, sodium alginate, Bacto-Adjuvant, certain synthetic polymers such as poly amino acids and co-polymers of amino acids, Block copolymer (CytRx, Atlanta, Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant (N,N-dioctadecyl-N',N'-bis(2-hydroxyethyl)-propanediamine), "REGRESSIN" (Vetrepharm, Athens, Ga.), paraffin oil, RIBI adjuvant system (Ribi Inc., Hamilton, Mont.), muramyl dipeptide and the like.

Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol.

Another example of an adjuvant useful in the compositions of the invention is SP-oil. As used in the specification and claims, the term "SP oil" designates an oil emulsion comprising a polyoxyethylene-polyoxypropylene block copolymer, squalane, polyoxyethylene sorbitan monooleate and a buffered salt solution. Polyoxyethylene-polyoxypropylene block copolymers are surfactants that aid in suspending solid and liquid components. These surfactants are commercially available as polymers under the trade name Pluronic®. The preferred surfactant is poloxamer 401 which is commercially available under the trade name Pluronic® L-121. In general, the SP oil emulsion is an immunostimulating adjuvant mixture which will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution. In one embodiment, the SP-oil emulsion is present in the final composition in v/v amounts of about 1% to 25%, preferably about 2% to 15%, more preferably about 5% to 12% v/v.

Yet another example of a suitable adjuvant for use in the compositions of the invention is AMPHIGEN™ adjuvant which consists of de-oiled lecithin dissolved in an oil, usually light liquid paraffin.

Other examples of adjuvants useful in the compositions of the invention are the following proprietary adjuvants: Microsol Diluvac Forte® duel emulsion adjuvant system, Emunade adjuvant, and Xsolve adjuvant. Both the Emunade and Xsolve adjuvants are emulsions of light mineral oil in water, but Emunade also contains alhydrogel, and d,l-α-tocopheryl acetate is part of the XSolve adjuvant. A still further example of a suitable adjuvant for use in the compositions of the invention is ImpranFLEX™ adjuvant (a water-in-oil adjuvant). A still further example of a suitable adjuvant is a Carbomer (Carbopol®) based adjuvant. Preferred Carbopol® adjuvants include Carbopol® 934 polymer and Carbopol®941 polymer.

In one embodiment, the adjuvant or adjuvant mixture is added in an amount of about 100 µg to about 10 mg per dose. In another embodiment, the adjuvant/adjuvant mixture is added in an amount of about 200 µg to about 5 mg per dose. In yet another embodiment, the adjuvant/adjuvant mixture is added in an amount of about 300 µg to about 1 mg/dose.

The adjuvant or adjuvant mixture is typically present in the vaccine composition of the invention in v/v amounts of about 1% to 25%, preferably about 2% to 15%, more preferably about 5% to 12% v/v.

Other "immunomodulators" that can be included in the vaccine include, e.g., one or more interleukins, interferons, or other known cytokines. In one embodiment, the adjuvant may be a cyclodextrin derivative or a polyanionic polymer, such as those described in U.S. Pat. Nos. 6,165,995 and 6,610,310, respectively.

A further aspect relates to a method for preparing an immunogenic composition according to the present invention. This method comprises i) culturing M.hyo in a suitable media over periods ranging from 18-144 hours; ii) subsequently inactivating the M.hyo culture; iii) harvesting the inactivated culture fluid, wherein the inactivated culture fluid comprises an M.hyo whole cell preparation comprising both a soluble liquid fraction and insoluble cellular material; iv) separating the soluble liquid fraction from the insoluble cellular material; and v) substantially removing both IgG and antigen/immunoglobulin immunocomplexes from the separated soluble liquid fraction.

An example of a suitable media for culturing M.hyo is PPLO Broth (*Mycoplasma* Broth Base), which when supplemented with nutritive enrichments, is used for isolating and cultivating *Mycoplasma*.

In some embodiments, the culture of M.hyo is grown until late log phase growth, after which the culture is inactivated. In some other embodiments, the culture is inactivated by raising the pH (e.g., to about 7.8). This occurs by exposing the production culture to an inactivation agent, such as binary ethylenimine (BEI). The BEI is generated in situ during incubation of L-bromoethylamine hydrobromide (BEA) in the production culture. Subsequently, the pH of the inactivated culture is neutralized, such as by adding an equivalent amount of an agent that neutralizes the inactivation agent within the solution. In some embodiments, the inactivation agent is BEI and the neutralization agent is sodium thiosulfate. In one embodiment, the pH of the inactivated culture is adjusted to about 7.4 by adding sodium thiosulfate.

In some embodiments, the soluble liquid fraction of the M.hyo whole cell preparation is separated from the insoluble cellular material using conventional methods. In one embodiment, this separation is by a filtration step. In another embodiment, this separation is by a centrifugation step. In yet another embodiment, the separation is by a precipitation step.

In one embodiment, the soluble liquid fraction of an inactivated, neutralized M.hyo whole cell preparation is treated with Protein A resin to substantially remove both the IgG and antigen/immunoglobulin immunocomplexes therein. In other embodiments, Protein G resin can be used to substantially remove both the IgG and antigen/immunoglobulin immunocomplexes contained in the soluble liquid fraction. Methods for removing both IgG and antigen/immunoglobulin immunocomplexes with either Protein A or Protein G resins are well known in the art.

According to a further aspect, the method for preparing an immunogenic composition, such as a vaccine, according to the invention comprises preparing the soluble M.hyo antigen as described above and mixing this with a suitable adjuvant and one or more pharmaceutically-acceptable carriers. This method optionally includes adding at least one additional porcine antigen, such as a PCV2 antigen and/or PRRS virus antigen and/or *Lawsonia intracellularis* antigen as described above.

A further aspect of the present invention relates to a kit. A "kit" refers to a plurality of components which are grouped together. In one embodiment, a kit according to the present invention includes a bottle (or other suitable receptable) comprising a protein-A or protein-G treated *Mycoplasma hyopneumoniae* (M.hyo) antigen that is compatible with antigens from other swine pathogens, wherein the M.hyo antigen is an M.hyo culture supernatant.

This M.hyo culture supernatant corresponds to the soluble portion of a *Mycoplasma hyopneumoniae* (M.hyo) whole cell preparation, wherein the soluble portion of the M.hyo preparation is substantially free of both (i) IgG and (ii) antigen/immunoglobulin immunocomplexes. Optionally, the kit can further include an instruction manual. The instruction manual includes the information to administer the immunogenic composition.

In some embodiments, the bottle containing the soluble portion of the M.hyo preparation further includes PCV2 antigen. In some embodiments, the M.hyo/PCV2 combination in the bottle is provided as a ready-to-use liquid composition.

In other embodiments, the kit includes a second bottle comprising PRRS virus antigen. In some embodiments, the PRRS virus antigen is in the form of a genetically modified, live virus which is provided in a lyophilized state. In such instances, the instruction manual will include the directions for re-hydrating the PRRS virus component with the liquid contents from a bottle containing the M.hyo/PCV2 combination. The instruction manual will also include the information to administer the resultant M.hyo/PCV2/PRRS trivalent formulation(s).

In some embodiments, an immunogenic composition according to this invention is administered to pigs having maternally derived antibodies against M.hyo. In other embodiments, an immunogenic composition of the present invention is administered to pigs having maternally derived antibodies against both M.hyo and at least one other microorganism that can cause disease in pigs.

In some embodiments, an immunogenic composition of the present invention, such as a monovalent or multivalent vaccine, is administered to a piglet aged 3 weeks or older. However, it is contemplated that a monovalent or multivalent vaccine composition according to the invention may also be used to re-vaccinate gilts pre-breeding. As is known in the art, a gilt is a female pig that has never been pregnant. Vaccinated gilts will pass maternally derived antibodies onto their suckling newborns via colostrum.

It is further contemplated that a monovalent or multivalent vaccine according to the invention can be used to annually re-vaccinate breeding herds. Preferably, a monovalent or multivalent vaccine according to the present invention is administered to pigs (e.g., piglets or gilts) in one dose. In one embodiment, a multivalent vaccine according to the present invention does not require mixing of separate monovalent vaccines prior to administration, i.e., it is provided as a ready-to-use formulation. In another embodiment, a multivalent formulation requires mixing of a divalent vaccine contained in a first bottle with a monovalent vaccine contained in a second bottle. Optionally, additional antigens can be added to either of these bottles.

In some embodiments, the onset of immunity is from 2-3 weeks post-vaccination with a monovalent or multivalent vaccine composition according to the present invention. In other embodiments, the duration of immunity is about 17-23 weeks post-vaccination with a monovalent or multivalent vaccine composition according to the present invention.

The following examples set forth preferred materials and procedures in accordance with the present invention. However, it is to be understood that these examples are provided by way of illustration only, and nothing therein should be deemed a limitation upon the overall scope of the invention.

EXAMPLES

Example 1: *Mycoplasma hyopneumoniae* Production Methods for PCV2 Combinable M.Hyo Antigen M.Hyo Fermentation and Inactivation Media for seed scale and antigen production was prepared as follows. Porcine heart derived Pleuropenumonia-like Organism (PPLO) Broth (BD Biosciences catalog No. 21498) was made per manufacturer's directions (i.e., 21 g/L) and yeast extract solution was made at 21 g/L in USP. Yeast extract solution was then added to the PPLO at 6.25% and the mixture was sterilized by heating to 121° C. for ≥30 minutes. Cysteine hydrochloride was prepared at 90 g/L and filter sterilized. Dextrose solution was made by adding 450 g of dextrose per liter of USP water followed by heat sterilization. To prepare the final medium, porcine serum was added to the base medium at 10% followed by cysteine at 0.01% and dextrose at 1.0%. The medium was inoculated with a 10% v:v of a log phase culture of *M. hyopeumoniae* (strain P-5722-3). The culture was held at 37° C. and pH and dO were maintained at 7.0 and 25%, respectively. At late log phase growth, the culture was inactivated by binary ethylenimine (BEI), an aziridine compound, produced from 2-bromoethylamine hydrobromide. Specifically, the inactivation occurred by raising the pH to 7.8 by adding 2-bromoethylaminehydrobromide (BEA) to a final concentration of 4 mM and incubating for 24 hours. The BEI was neutralized by addition of sodium thiosulfate at a 1:1 molar ratio followed by additional 24 hour incubation. The inactivated culture fluid was held at 2-8° C. until further processing.

Example 2: Chimeric Porcine Circovirus (cPCV)1-2 Production Methods

The cPCV1-2 was constructed by cloning the immunogenic capsid gene of the pathogenic porcine circovirus type 2 (PCV2) into the genomic backbone of the nonpathogenic porcine circovirus type 1 (PCV1). The procedure for construction of the chimeric DNA clone is described, for example, in U.S. Pat. No. 7,279,166, which is incorporated herein by reference in its entirety. An infectious stock of the chimeric virus was acquired from Dr. X. J. Meng, Virginia Polytechnic Institute and State University, Blacksburg, Va., and was used to infect Porcine Kidney (PK)-15 cells grown in Minimum Essential Medium (MEM) supplemented with 0.05% lactalbumin hydrolysate (LAH), 30 μg/mL gentamicin sulfate, and 5% fetal bovine serum. The resulting cPCV1-2 infected PK-15 cells were further expanded by serial passing four more times using the same growth medium except with 2-3% fetal bovine serum. The fifth passage was frozen, thawed and filtered, and the resulting lysates were used to prepare a pre-master seed and subsequent master seed.

The medium which was used for producing virus seeds was the same as that used in producing virus stock. For the growth medium, MEM, OptiMEM, or equivalent is the basal medium which can be used for planting the PK-15 cell line for outgrowth. The growth medium can be supplemented with up to 10% bovine serum, up to 0.5% lactalbumin hydrolysate, up to 0.5% bovine serum albumin, and up to 30 µg/mL gentamicin. For the virus propagation medium, MEM, OptiMEM, or equivalent is used. The virus propagation medium can be supplemented with up to 0.5% lactalbumin hydrolysate, up to 2% bovine serum, up to 0.5% bovine serum albumin, and up to 30 µg/mL gentamicin. Up to 5 g/L glucose and up to 5 mmol/L L-glutamine can be added to the growth medium and/or the virus propagation medium as required to sustain the cells.

The cPCV1-2 master seed virus are added to a cell suspension of PK-15 cells and adsorbed for up to 3 hours. Seed virus is diluted in growth basal medium to provide a multiplicity of infection (MOI) of 0.1-0.0001.

Cultures of PK-15 cells are initially inoculated with working seed virus at the time of cell planting, or when cells reach approximately 20% to 50% confluency. This initial passage may be referred as "One-Step Infection Method" for the production of antigen stock, or may be further used for serial passages. For serial passages, the cPCV1-2 infected PK-15 cells are further expanded up to passage 7 by serial splits at the ratio of 1:5-20 for virus propagation. Culture medium containing an infected cell suspension from the previous passage serves as seed material for the next passage. The cPCV1-2 infected cells are incubated for three (3) to 14 days for each passage at 36±2° C. when cells reach 90% confluency. The cPCV1-2 virus causes observable cytopathic changes during viral replication. At harvest, rounding of cells and considerable floating debris is observed. Cultures are also observed for visual evidence of bacterial or fungal contamination. The incubation time between harvests for the cPCV antigen is provided in Table 1 below:

TABLE 1

Minimum and Maximum Times for Harvesting cPCV Antigen

| Method | Minimum/Maximum Time | Temperature Range |
|---|---|---|
| One-Step Infection | 5 to 16 days | 36 ± 2° C. |
| Serial Passage (MSV +3 to MSV +7) | 16 to 36 Days | 36 ± 2° C. |

The cPCV1-2 culture fluids are harvested into sterile vessels and are sampled for *mycoplasma* testing using known methods. Multiple harvests may be conducted from roller bottles, bioreactors and perfusion vessels.

Prior to inactivation of the harvested cPCV1-2 virus, one or more antigen lots may be concentrated (e.g., up to 60×) by ultrafiltration. The concentrates may be washed with balanced salt solution to reduce serum proteins.

The method of inactivation, attenuation, or detoxification of the cPCV1-2 virus will now be described. After cPCV antigen concentration, Beta-propiolactone (BPL) is added to the pooled cPCV1-2 viral material to obtain an approximate concentration of 0.2% v/v. The pooled viral fluids are then agitated for a minimum of 15 minutes and then the inactivating bulk antigen fluids are transferred to a second sterile vessel. The transferred antigen fluids are maintained at 2-7° C., with constant agitation, for a minimum of 24 hours. After a minimum of 24 hours, a second addition of 0.2% v/v of BPL is added to the pooled suspension. The contents are subsequently agitated, transferred to a third vessel, and maintained at 2-7° C., with constant agitation, for an additional time of not less than 84 hours. In general, the total inactivation time is not less than 108 hours and not more than 120 hours. The inactivation method is summarized in Table 2 below.

TABLE 2

Inactivation Method

| Inactivant | Final Concentration | Temp. Range | Time-Hours (Min/Max) |
|---|---|---|---|
| Beta-propiolactone (BPL) | 0.4% v/v (2 × 0.2% v/v additions) | 2-7° C. (w/Agitation) | 108-120 |

The inactivation is terminated by the addition of a final concentration of not more than 0.1 M solution of sodium thiosulfate. The pH of the inactivated antigen stock is adjusted to about 6.8 using NaOH or HCl. Following inactivation, a representative sample is taken from the pool and tested for completion of inactivation. The inactivated cPCV1-2 antigen product is standardized to a meet a target of greater than 1.0 RP as measured via potency ELISA.

Example 3: Down Stream Processing of M. Hyo Antigens and Analytical Testing of these Processed Antigens Down Stream Processing of M.Hyo Antigens:

Inactivated fermentation fluid (prepared as described above in Example 1) was treated for each indicated group as follows. These processed M.hyo antigens were employed in Example 4 below.

T02: (Whole Bulk) Not processed.

T03: (10× UF concentrated) Concentrated via tangential flow filtration via a 100 KDa molecular weight cutoff membrane (hollow fiber). Final volume reduction was equal to 10×.

T04 & T05: (10× UF concentrated & centrifuged) Concentrated *mycoplasma* cells (from T03) were collected and washed one time with PBS via centrifugation at ~20,000×g (Sorvall model RC5B).

T06 & T07: (10× centrifuged) Inactivated fermentation fluid was centrifuged at ~20,000×g (Sorvall RC5B) and washed one time by resuspending the cells in PBS followed by an additional centrifugation. Final volume reduction was equal to 10×.

T08: (10× centrifuged & Heated) *Mycoplasma* cells were concentrated and washed per T06 and heated to 65° C. for 10 minutes.

T09: (Cell-free supernatant) Supernatant collected from the first centrifugation as described for T06 was filter sterilized through a 0.2 micron filter (Nalgene).

T10: (Cell-free supernatant-Protein-A treated) Sterile supernatant (prepared per T09) was mixed with Protein A resin (Protein A Sepharose, Pharmacia Inc) at a 10:1 volume ratio for 4 hours. Resin was removed sterile filtration and filtered fluid was stored at 2-8° C. This process uses post-fermentation "downstream" protein A treatment to remove antibodies and immunocomplexes. Although the present invention does not preclude upstream protein A treatment, the present inventors have found that in the case of M.hyo, upstream protein A treatment of the growth media led to p46 results which were lower and inconsistent as compared to untreated media (data not shown).

Analytical Testing of M.Hyo Downstream Processed Antigens

The downstream processed M.hyo antigens preparations (prepared as described above) were tested for the recovery of M.hyo specific p46 antigen, and the presence of PCV2 antibody. In addition, these M.hyo antigen preparations were tested for the presence of Torque Teno Virus (TTV), including genotype 1 (g1TTV) and genotype 2 (g2TTV). The results are presented below in Table 3.

TABLE 3

Characterization of M.hyo Downstream Processed Antigens

| Treatment | Bulk M.Hyo p46 RU/mL | PCV2 ab S/P ratio | qPCR DNA g1TTV | qPCR DNA g2TTV |
|---|---|---|---|---|
| Whole bulk | 809 | 0.248 | 1.00E+03 | 1.78E+03 |
| 10x UF concentrated | 6666 | 0.819 | 1.00E+03 | 9.94E+03 |
| 10x UF conc. + Centrifuge | 614 | 0.019 | 0 | 0 |
| 10x Centrifuged | 763 | −0.015 | 1.90E+02 | 1.91E+02 |
| 10x Centrifuged + Heated | 690 | −0.012 | 0 | 2.07E+02 |
| Cell-free supe | 719 | 0.242 | 4.20E+02 | 3.23E+03 |
| Cell-free supe (Prot A) | 826 | −0.014 | 0 | 2.06E+03 |

With reference to Table 3 above, recovery of the M.hyo-specific p46 antigen was demonstrated for each of the M.hyo downstream processed antigen preparations. In addition, the following treatments successfully removed PCV2 antibody: 10× UF concentrated & centrifuged, 10× centrifuged, 10× centrifuged & heated and Cell-free supernatant (Protein-A treated). With respect to TTV, the following treatments successfully removed g1TTV: 10× UF concentrated & centrifuged, 10× centrifuged & heated, and Cell-free supernatant (Protein-A treated). Only the treatment designated 10× UF concentrated & centrifuged removed g2TTV. Torque teno virus isolates, including genotypes 1 and 2 are described in US20110150913, which is incorporated herein by reference in its entirety.

Since it is known in the art that Protein A binds IgG, it is understood by those of ordinary skill in the art that not only PCV2 antibody, but other swine antibodies, including PRRS antibody, HPS antibody, and SIV antibody will be effectively removed by the Protein-A treatment. This makes the Cell-free Protein-A treated M.hyo supernatant of this invention compatible not only with PCV2 antigen, but also with other porcine antigens due to the lack of immunological interference between the antigens. Additionally, the removal of the non-protective cell debris and removal of the immunoglobulin and antigen/immunoglobulin complexes is reasonably expected to make a safer vaccine.

Example 4: Preparation of M.Hyo Experimental Vaccine Formulations

All experimental M.hyo vaccines were formulated with a final concentration of 5% Amphigen adjuvant. In addition, all vaccines were standardized with a p46 ELISA and preserved with thimerosol. The experimental vaccine formulations were prepared with M.hyo antigens processed according to treatments T02-T10 above. In addition, Treatment T01 corresponded to a placebo (no M.hyo antigen, only 5% Amphigen adjuvant) whereas Treatment T11 is a positive control corresponding to an expired bacterin-based M.hyo vaccine (RespiSure-ONE®, Pfizer Animal Health). These formulations are described in Table 4 below.

TABLE 4

M.hyo Experimental Vaccine Formulations

| Treatment | IVP Serial* | Target p46 units/ds | M Hyo antigen (mL) | Adjuvant (mL) | Formulation Vol. (mL) |
|---|---|---|---|---|---|
| T01 | 123639 (Placebo) | 5% Amphigen only, No Antigen | | | |
| T02 | L100211A | 452 | 279.36 | 250 | 1000 |
| T03 | L100211B | 452 | 6.78 | 50 | 200 |
| T04 | L100211C | 452 | 73.62 | 50 | 200 |
| T05 | L100211D | 816 | 132.90 | 50 | 200 |
| T06 | L100211E | 452 | 59.24 | 50 | 200 |
| T07 | L100211F | 816 | 106.95 | 50 | 200 |
| T08 | L100211G | 452 | 65.51 | 50 | 200 |
| T09 | L100211H | 452 | 62.87 | 50 | 200 |
| T10 | L100211J | 452 | 54.72 | 50 | 200 |
| T11 | A827870 | Expired "RespiSure" vaccine | | | |

*Investigational Veterinary Product (IVP) Serial

Example 5: Evaluation of the In Vivo Efficacy of M.Hyo Vaccines with M.Hyo Antigens from Different Downstream Processes This study was conducted to evaluate the in vivo efficacy of *Mycoplasma hyopneumoniae* (M hyo) vaccines with M hyo antigens from different downstream processes (DSP). Pigs at 3 weeks of age were intramuscularly inoculated with a single dose of the different vaccine formulations described in Table 4 above. Sixteen animals were included in each of the treatment groups. Animals were challenged 21 days after vaccination with a virulent M.hyo field isolate. Animals were necropsied 28 days after challenge and the lungs were removed and scored for consolidation consistent with M.hyo infection. The primary criterion for protection against M.hyo challenge was lung consolidation scores. It is generally accepted that there is a relationship between the size of the lung lesions caused by enzootic pneumonia and an adverse effect on growth rate. Table 5 below contains the lung lesion scores for the respective treatment groups. Statistical significance was determined by a Mixed Model Analysis of lung scores for each group.

TABLE 5

Lung Lesion Results

| Treatment | Description | p46 RP Target/ Observed | % Lung Lesions Back Transformed LS Means | Range % Lung with Lesions | Contrast | p-value | Significant |
|---|---|---|---|---|---|---|---|
| T01 | Placebo (5% Amphigen) | N/A | 11.7 | 1.2-44.3 | N/A | N/A | N/A |
| T02 | Whole bulk | 13/15.6 | 1.2 | 0.1-18.5 | T01 vs 02 | 0 | Yes |
| T03 | Whole bulk UF 10x | 13/11.9 | 0.3 | 0.0-2.8 | T01 vs 03 | 0 | Yes |
| T04 | UF 10x + Centrifuged | 13/28.1 | 5.9 | 0.0-40.5 | T01 vs 04 | 0.1589 | No |
| T05 | UF 10x + Centrifuged | 24/48.2 | 3.7 | 0.0-42.3 | T01 vs T05 | 0.0309 | Yes |
| T06 | 10x Centrifuged | 13/30.4 | 4.7 | 0.0-23.6 | T01 vs 06 | 0.0388 | Yes |
| T07 | 10x Centrifuged | 24/57.4 | 4.6 | 0.3-37.3 | T01 vs T07 | 0.0323 | Yes |
| T08 | 10x Centrifuged + Heat | 13/17.7 | 4.5 | 0.3-21.7 | T01 vs T08 | 0.0137 | Yes |
| T09 | Supernatant (no cells) | 13/14.1 | 1.4 | 0.0-33.0 | T01 vs T09 | 0.0004 | Yes |
| T10 | Supernatant + Prot A | 13/12.1 | 3.1 | 0.0-25.8 | T01 vs T10 | 0.0094 | Yes |
| T11 | Expired RSO | 13/12.5 | 2.2 | 0.1-32.1 | T01 vs T11 | 0.0009 | Yes |

With reference to Table 5 above, the results with M.hyo antigens from different downstream processes indicated that all experimental vaccines except T04 significantly differed from the placebo. These M.hyo lesion results are depicted graphically in FIG. 1. As shown in FIG. 1, T04 gave unacceptable results. All other treatments differed significantly from the placebo (T01). The lung consolidation scores indicated that T02, T03 and T09-T11 gave the most efficacious protection against M.hyo challenge.

The p46 relative potency of the experimental vaccines was assessed by using a double antibody sandwich enzyme-linked immunosorbent assay (DAS ELISA). The p46 DAS ELISA results presented in Table 5 above indicate that all the experimental vaccines exceeded the target potency. In addition, the p46 relative potency was either maintained or increased during storage of the vaccines over a one-month period (data not shown). A perceived increase in potency over time was observed in centrifuged antigens with the exception of those antigens that were subjected to heat. While not wishing to be bound by any one theory, it is likely that cell "carcasses" are breaking up over time and released more of the membrane bound p46 antigen in the case of the centrifuged antigens.

Example 6: Evaluation of the Compatibility of the Experimental M.Hyo Vaccines with PCV2 Antigen This study was conducted to evaluate the compatibility of the M.hyo experimental vaccines with M hyo antigens from different downstream processes with PCV2 antigen. The M.hyo experimental vaccine formulations are described in Tables 4 and 5 above. The observed p46 relative potencies for these vaccines are described in Table 5 above. These M.hyo experimental vaccines were each combined with PCV2 antigen. In this example, the PCV2 antigen was a killed PCV Type 1-Type 2 chimeric virus (Fostera PCV) prepared as described above in Example 2. The chimeric virus was included in the compositions at an initial level of about 1.6≤RP, wherein the RP is the Relative Potency unit determined by PCV2 ELISA antigen quantification (in vitro potency test) compared to an efficacious reference vaccine.

Figure 2:
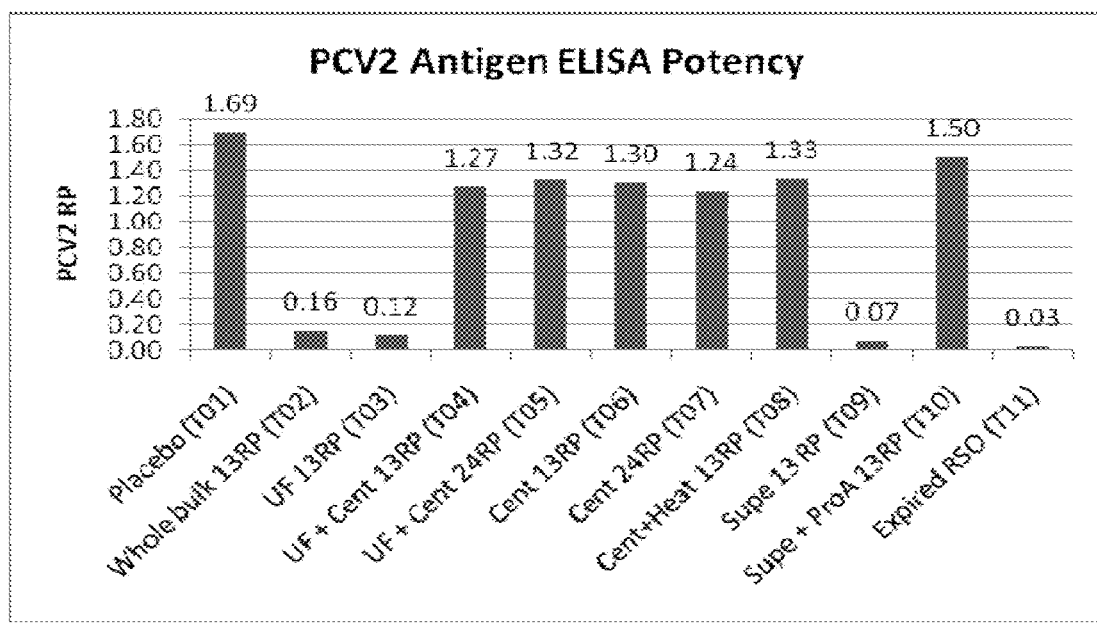
FIG. 2 is a graph showing the PCV2 antigen potency results (PCV2 antigen ELISA) of M.hyo vaccines in combination with killed PCV Type1-Type2 chimeric virus. The chimeric virus was included in the compositions at an initial level of about 1.6≤RP. The status of each sample is expressed as relative potency (RP).

The experimental M.hyo/PCV2 combination formulations were evaluated by PCV2 ELISA. The results are presented in FIG. 2. As shown in FIG. 2, only the M.hyo antigen preparations from the following downstream processes were compatible with the PCV2 antigen: Ultrafiltration & Centrifugation (T04 & T05), Centrifugation (T06 & T07), Centrifugation plus heat (T08) and Protein A-treated Supernatant (T10). Of these, the M.hyo Protein A-treated supernatant was the most compatible with PCV2 antigen when compared to the placebo control which included the chimeric virus and Amphigen adjuvant, but no M.hyo antigen. The level of chimeric PCV virus in the Protein-A treated supernatant was 1.5 RP as compared to 1.69 RP for the placebo. It was therefore concluded that there is no or minimal immunological interference between the Protein-A treated M.hyo soluble antigen preparation and PCV2 antigen of the chimeric virus.

The in vivo efficacy of the Protein-A treated M.hyo supernatant demonstrated in Example 5 above together with the results described in the present example indicated that the Protein-A treated supernatant was a potentially effective platform for M.hyo-PCV2 combinations.

Example 7: Evaluation of PCV2 Efficacy of a 1-Bottle PCV2/M.Hyo Combination Vaccine in Different Adjuvant Formulations This study was designed to evaluate the PCV2 efficacy in a 1-bottle PCV2/M.hyo combination vaccine in different adjuvant formulations. In this example, the PCV2 antigen was a killed PCV Type 1-Type 2 chimeric virus (Fostera PCV). The chimeric virus was combined with an M.hyo soluble antigen preparation that was substantially free of IgG (i.e., Protein A-treated supernatant).

Processing of Fluids:

Inactivated M.hyo fermentation fluid (described above in Example 1) was treated for each indicated group as follows.

T02-T04: Whole fermentation fluid containing live *M. hyopneumoniae* cells (described above) was centrifuged at ~20,000×g (Sorvall RCSB) and the supernatant collected and sterilized through a 0.2 μM filter. rProtein A Sepharose (part number 17-5199-03, GE Healthcare) was packed into a 1 L chromatography column. After removal of the storage buffer and treatment with 2 column volumes of 1M acetic acid, the resin was equilibrated with 5 column volumes of 50 mM NaPO4/1M NaCl buffer, pH 7.04. Approximately 2 liters of the clarified/filtered M. hyopneumoniae antigen containing fluids were passed through the Protein A resin at a flow rate of 100 cm/hr. The flow through was collected and sterilized via 0.2 μM filter.

T05: This is a positive control corresponding to a Fostera PCV-like formulation (no M.hyo antigen). The level of the chimeric virus in this Fostera PCV-like formulation was approximately at Minimum Immunizing Dose (MID) formulation levels. The chimeric virus was included in the PCV2/M.hyo experimental vaccines at similar formulation levels.

All experimental PCV2/M.hyo vaccines were formulated with different adjuvant formulations. The experimental vaccine formulations were prepared with M.hyo antigens processed according to treatments T02-T04 above. In addition, Treatment T01 corresponded to a placebo (sterile saline).

All vaccines were standardized with a p46 ELISA and preserved with thimerosol.

Figure 4:
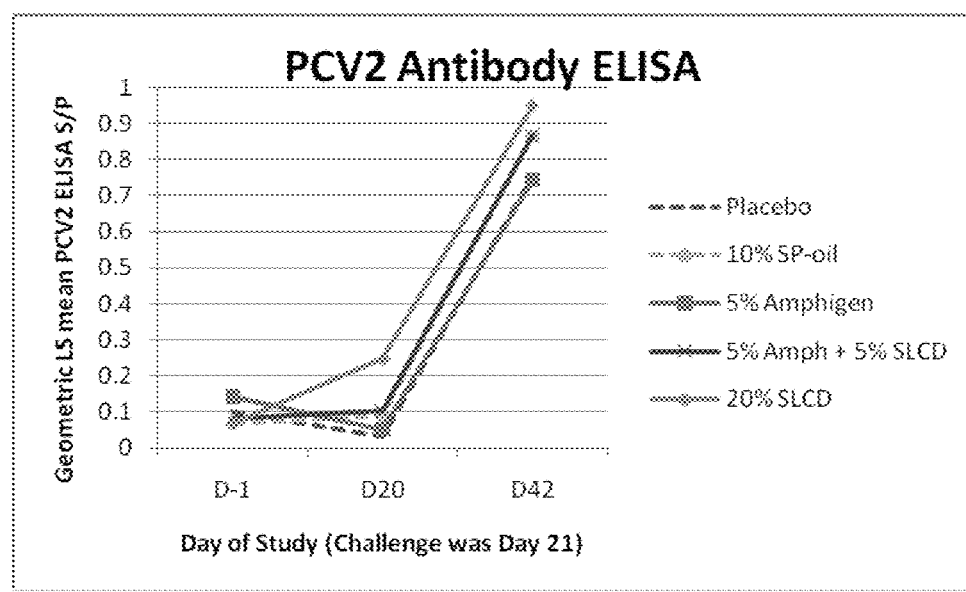
FIG. 4 is a graph showing the PCV2 antibody ELISA (S/P) serological results observed with PCV/M.hyo vaccine formulations employing different adjuvant platforms on days 1, 20, and 42 of challenge.

These experimental formulations are described in Table 6 below, wherein the symbol * indicates the M hyo antigen from global M hyo seed, Protein A treated supernatant and the symbol ** indicates Investigational Veterinary Product (IVP) serial.

status of each sample was expressed as a sample to positive ratio (S/P). As shown in FIG. 4, 20% SLCD was the only treatment which was significantly different from the placebo (T01) at both day 20 and day 42. Also, 5% Amphigen was the only treatment not significantly different from the placebo at day 20.

Figure 5:
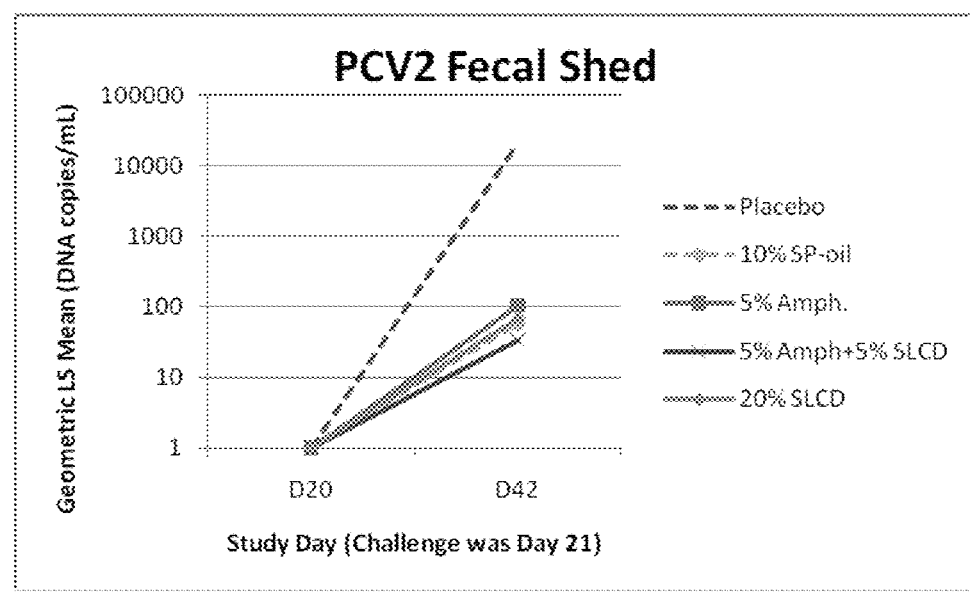
FIG. 5 is a graph showing the PCV2 fecal shed obtained with the T02-T04 treatments described in Example 7 vs. a placebo (T01). The results are expressed as PCV2 DNA copies/ml.

FIG. 5 is a graph showing the PCV2 fecal shed obtained with the T02-T04 treatments vs. the placebo (T01). These results are expressed as PCV2 DNA copies/ml. The results in FIG. 5 indicate that all treatments had significantly less fecal shed when compared to the placebo at day 42. In addition, 5% Amphigen & 5% SLCD (T04) had significantly less fecal shed as compared to 5% Amphigen (T03) at day 42. No other treatment differences were noted.

Figure 6:
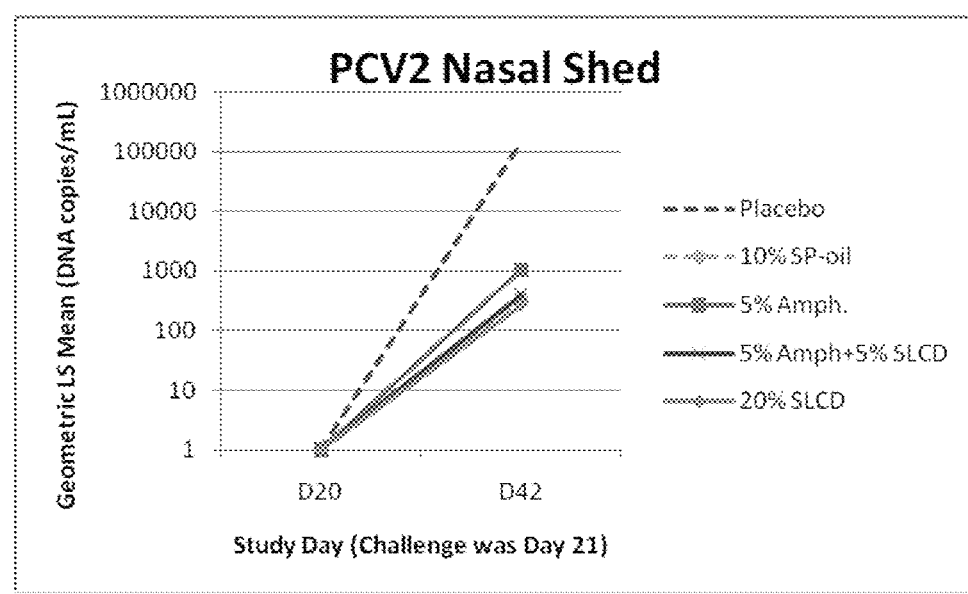
FIG. 6 is a graph showing the PCV2 nasal shed obtained with the T02-T04 treatments described in Example 7 vs. the placebo (T01). The results are expressed as PCV2 DNA copies/ml.

FIG. 6 is a graph showing the PCV2 nasal shed obtained with the T02-T04 treatments vs. the placebo (T01). These results are expressed as PCV2 DNA copies/ml. The results in FIG. 6 indicate that all treatments had significantly less nasal shed when compared to the placebo at day 42. In addition, 20% SLCD (T05) had significantly less nasal shed compared to 5% Amphigen (T03) at day 42. No other treatment differences were noted.

Figure 7A:
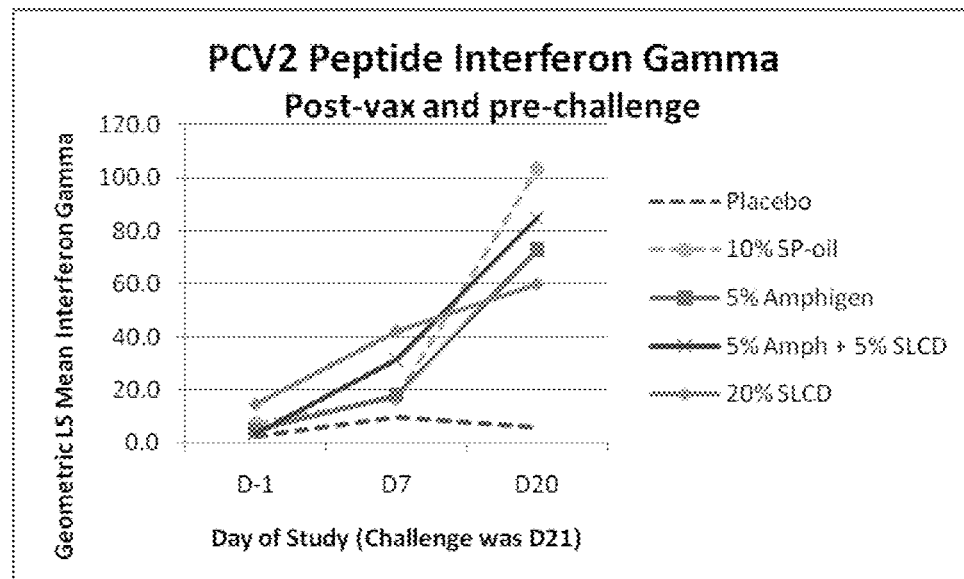
FIG. 7A and FIG. 7B are graphs showing the results of an interferon-gamma (IFN-γ) test that measures PCV2-specific cellular mediated immune (CMI) responses. The results of post-vaccination/pre-challenge are presented in FIG. 7A, and the results of post-vaccination/post-challenge are presented in FIG. 7B. Stimulation of $5 \times 10^6$ cells was considered significant.
Figure 7B:
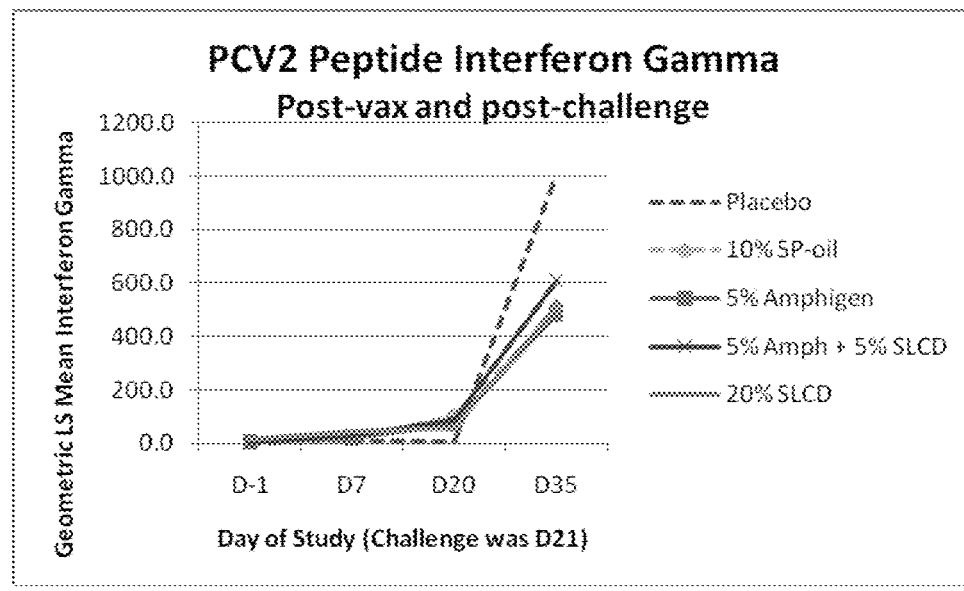

FIG. 7A and FIG. 7B are graphs showing the results of an interferon-gamma (IFN-γ) test that measures PCV2-specific cellular mediated immune (CMI) responses. The CMI results are shown post-vaccination/pre-challenge (FIG. 7A), and post-vaccination/post-challenge (FIG. 7B). In these

TABLE 6

PCV2/M.hyo Experimental Vaccine Formulations Used for PCV2 Efficacy Study

| Treatment | IVP Serial** | PCV1-2 Ag | M Hyo* Ag | Adjuvant | Other |
|---|---|---|---|---|---|
| T01 | 87-244-DK (Placebo) | | | NA | Sterile Saline |
| T02 | L0411RK08 | 1.6 RP | 7.5 RP | 10% SP Oil | NA |
| T03 | L0411RK09 | | | 5% Amphigen | |
| T04 | L0611RK03 | | | 5% Amphigen + 5% SLCD | |
| T05 | L0611RK04 | | NA | 20% SLCD | |

Pigs at 3 weeks of age were intramuscularly inoculated with a single dose of the different vaccine formulations described in Table 6 above. Sixteen animals were included in each of the treatment groups. Animals were challenged 21 days after vaccination with a virulent PCV2 field isolate.

Figure 3:
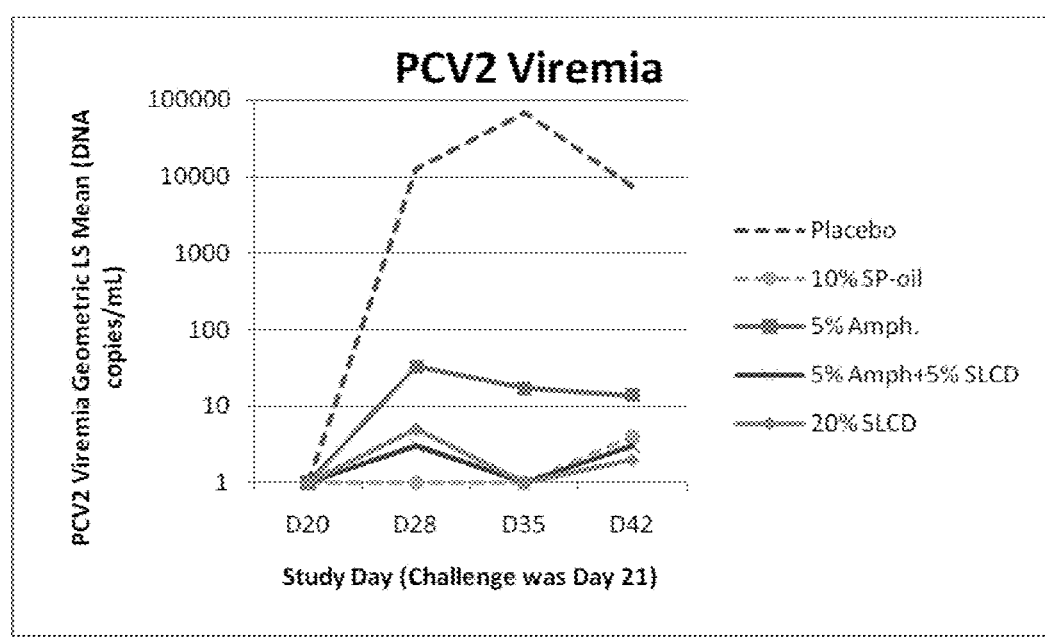
FIG. 3 is a graph showing the PCV2 viremia results (PCV2 Quantitative PCR) observed with PCV/M.hyo vaccine formulations employing different adjuvant platforms.

FIG. 3 is a graph showing the PCV2 viremia results (PCV2 Quantitative PCR) observed with the different adjuvant platforms. It is noted that PCV2 viremia was used as the primary efficacy variable. The PCV2 viremia results are presented as DNA copies/ml. As shown in FIG. 3, all treatments had significantly less viremia compared to the placebo on days 28, 35 and 42 (challenge was day 21). The 10% SP-oil adjuvant had significantly less viremia compared to 5% Amphigen at Days 28 and 35. The 5% Amphigen plus 5% SLCD adjuvant had significantly less viremia compared to 5% Amphigen at Days 28 and 35. The 20% SLCD adjuvant platform had significantly less viremia compared to 5% Amphigen at Days 28, 35 and 42.

PCV2 Serology, PCV2 fecal shed, PCV2 nasal shed, Cell Mediated Immune (CMI) responses, lymphoid depletion, and Immunohistochemistry (IHC) were also monitored as secondary efficacy variables. These results will now be described below.

FIG. 4 is a graph showing the PCV2 ELISA results on days 1, 20 and 42 of the study (challenge was day 21). The graphs, stimulation of $5 \times 10^6$ cells was considered significant ( . . . ). All PCV2/M.hyo experiment vaccines gave a detectable IFN-γ response post-vaccination. The 10% SP-oil (T02) drove the strongest IFN-γ response post-vaccination. The 20% SLCD (T05) induced an earlier response, but the lowest response at day 20. There was a large post-challenge response, especially seen in the placebo group. Additionally, the post-challenge response was lower in the vaccinated pig treatment groups as compared to the placebo group.

Table 7 below shows the lymphoid depletion obtained with the experimental treatments contrasted to the placebo.

TABLE 7

PCV2 Histopathology (Lymphoid Depletion)

| | Lymphoid Depletion | | | Contrasted to Placebo | |
|---|---|---|---|---|---|
| Treatment | Positive | Negative | % Ever Pos. | P-value | Significant |
| Placebo | 9 | 7 | 56% | NA | NA |
| 10% SP-oil | 1 | 15 | 6% | 0.0059 | Yes |
| 5% Amphigen | 1 | 15 | 6% | 0.0059 | Yes |

TABLE 7-continued

PCV2 Histopathology (Lymphoid Depletion)

| Treatment | Lymphoid Depletion | | | Contrasted to Placebo | |
|---|---|---|---|---|---|
| | Positive | Negative | % Ever Pos. | P-value | Significant |
| 5% Amph + 5% SLCD | 0 | 16 | 0% | 0.0008 | Yes |
| 20% SLCD | 1 | 15 | 6% | 0.0059 | Yes |

The results presented in Table 7 above show that all vaccines afforded strong protection against lymphoid depletion. Also, no statistically significant vaccine treatment contrasts were observed. Table 8 below shows the immunohistochemistry obtained with the experimental treatments contrasted to the placebo.

TABLE 8

PCV2 Histopathology (Immunohistochemistry)

| Treatment | Immunohistochemistry | | | Contrasted to Placebo | |
|---|---|---|---|---|---|
| | Positive | Negative | % Ever Pos. | P-value | Significant |
| Placebo | 12 | 4 | 75% | NA | NA |
| 10% SP-oil | 0 | 16 | 0% | 0.0001 | Yes |
| 5% Amphigen | 1 | 15 | 6% | 0.0002 | Yes |
| 5% Amph + 5% SLCD | 0 | 16 | 0% | 0.0001 | Yes |
| 20% SLCD | 0 | 16 | 6% | 0.0001 | Yes |

The results presented in Table 8 above show that all vaccines afforded strong protection against PCV2 colonization as evidenced by immunohistochemistry. Also, no statistically significant vaccine treatment contrasts were observed.

In conclusion, the results presented in this example demonstrate that the M.hyo soluble antigen preparation does not interfere with PCV2 efficacy. The results also show that all the PCV/M.hyo experimental vaccine formulations provide efficacy against PCV2 challenge. Additionally, the results indicate that there are some statistical and numerical differences obtained with the different adjuvant formulations, with 10% SP-oil yielding the strongest efficacy.

Example 8: Evaluation of M.Hyo Efficacy of a 1-Bottle PCV2/M.Hyo Combination Vaccine in with Different Adjuvant Formulations This study was designed to evaluate the M.hyo efficacy of a 1-bottle PCV2/M.hyo combination vaccine with different adjuvant formulations. The M.hyo antigen was combined with Porcine Circovirus (Type 1-Type 2 Chimera, or PCV1-2, killed virus) in one bottle.
Processing of Fluids:
Inactivated M.hyo fermentation fluid (described above in Example 1) was treated for each indicated group as follows.
T02-T04: These treatments were the same as those described for treatment groups T02-T04 in Example 7 above.
T05: This was formulated with inactivated M.hyo cells (M.hyo bacterin) as described in Example 1 above under the heading "Fermentation and Inactivation".
All experimental PCV2/M.hyo vaccines were formulated with different adjuvant formulations. The experimental vaccine formulations were prepared with M.hyo antigens processed according to treatments T02-T04. In addition, Treatment T01 corresponded to a placebo (sterile saline). Treatment T05 is a positive control corresponding to an expired RespiSure® vaccine, which is an M.hyo bacterin-based vaccine (Pfizer Animal Health).

These experimental formulations are described in Table 9 below, wherein the symbol * indicates the M hyo antigen from global M hyo seed, Protein A treated supernatant and the symbol ** indicates Investigational Veterinary Product (IVP) serial.

TABLE 9

PCV2/M.hyo Experimental Vaccine Formulations Used for M.hyo Efficacy Study in Different Adjuvant Formulations

| Treatment | IVP Serial ** | PCV1-2 Ag | M Hyo* Ag | Adjuvant | Other |
|---|---|---|---|---|---|
| T01 | 87-244-DK (Placebo) | | NA | | Sterile Saline |
| T02 | L0411RK08 | 1.6 RP | 7.5 RP | 10% SP Oil | NA |
| T03 | L0411RK09 | | | 5% Amphigen | |
| T04 | L0611RK03 | | | 5% Amphigen + 5% SLCD | |
| T05 | A827870 | Expired "RespiSure" vaccine | | | |

Pigs at 3 weeks of age were intramuscularly inoculated with a single dose of the different vaccine formulations described in Table 9 above. Fourteen animals were included in both the placebo and 10% SP-oil groups, thirteen animals were included in the positive control group, and sixteen animals were included in both the 5% Amphigen and 5% Amphigen+5% SLCD groups.

Animals were challenged 21 days after vaccination with a virulent M.hyo field isolate. Animals were necropsied 28 days after challenge and the lungs were removed and scored for consolidation consistent with M.hyo infection. Table 10 below contains the lung lesion scores for the respective treatment groups. Statistical significance was determined by a Mixed Model Analysis of lung scores for each group.

TABLE 10

M.hyo Lung Lesions

| Treatment | # Animal | LS Mean Lung Lesion | Range % Lung Lesion |
|---|---|---|---|
| Placebo (T01) | 14 | 13.1% | 0.1-50.5 |
| 10% SP-oil (T02) | 14 | 4.3% | 0.0-50.8 |
| 5% Amphigen (T03) | 16 | 4.7% | 0.0-38.5 |
| 5% Amph + 5% SLCD (T04) | 16 | 12.0% | 0.1-55.8 |
| Expired RSO (T05) | 13 | 2.28% | 0.0-34.5 |

As indicated in Table 10 above, the placebo group had a mean lung lesion score of 13.1%, as compared to the 10% SP-oil and 5% Amphigen treatment groups which had mean lung scores of 4.3% and 4.7%, respectively. Both the 10% SP-oil and 5% Amphigen formulations reduced and/or prevented lung lesions. Thus, the experimental PCV/M.hyo vaccines formulated with 10% SP-oil or 5% Amphigen were considered efficacious. The PCV2 antigen did not appear to interfere with the M.hyo efficacy of these formulations.

In contrast, the 5% Amphigen+5% SLCD group had a mean lung lesion score of 12.0%. which was an unacceptable result in that it was not different as compared to the placebo. Consequently, the experiment PCV/M.hyo vaccine formulated with 5% Amphigen+5% SLCD was not considered as efficacious.

It is noted that due to the reduced animal number and high variability in lung lesion scoring, no statistical treatment effect could be conclusively demonstrated in this study. For this reason, it was decided that another study would be designed to test the M.hyo efficacy of the PCV/M.hyo experimental formulations in 10% SP-oil. This repeat study is presented in Example 9 below.

Example 9: Evaluation of M.Hyo Efficacy of a 1-Bottle PCV2/M.Hyo Combination Vaccine in 10% SP-Oil This study is a proof of concept designed to evaluate the M.hyo fraction efficacy of four experimental PCV2/M.hyo vaccines (Serials L0711RK11, L0711RK12, L0711RK13 and L0711RK14 in Table 11 below) prepared by different M.hyo manufacturing processes which utilize Protein A for IgG removal compared to control vaccines prepared with the standard M.hyo manufacturing process. Each of these four experimental PCV2/M.hyo vaccines included 10% SP-oil as the adjuvant.

Processing of Fluids:

T02: Inactivated *M. hyopneumoniae* antigen as described under "Fermentation and Inactivation" in Example 1 above.

T03 and T04: Formulated with inactivated *M. hyopneumoniae* cells as described under "Fermentation and Inactivation" in Example 1 above.

T05: Protein A treatment of medium used to grow *M. hyopneumoniae*. PPLO (porcine heart derived) was made per manufacturer's directions (i.e., 21 g/L) and yeast extract solution was made at 21 g/L in USP. Yeast extract solution was added to the PPLO at 6.25% and the mixture was sterilized by heating to 121° C. for ≥30 minutes. Cysteine hydrochloride was prepared at 90 g/L and filter sterilized. Dextrose solution was made by adding 450 g of dextrose per liter of USP water followed by heat sterilization. To prepare the final medium, porcine serum was added to the base medium at 10% followed by cysteine at 0.01% and dextrose at 1.0%. Antibodies in the complete PPLO media were removed by treatment with protein A. Briefly, one liter of rProtein A Sepharose (part number 17-5199-03 GE Healthcare) was packed into a glass column (10×11.5 cm). After removal of storage buffer, the column was treated with 2 column volumes of 1M acetic acid. The resin was equilibrated with 5 column volumes of 50 mM NaPO4, 1M NaCl buffer (pH 7.0). Fifteen liters of complete PPLO medium was loaded onto the resin at a linear flow rate of 140 cm/hour. The column flow through was collected and filter sterilized through a 0.2 micron filter (Sartorius). The treated medium was used propagate *M. hyopneumoniae* cells as described under "Fermentation and Inactivation" above. Whole inactivated culture (including cells) was formulated into the final vaccine.

T06: Inactivated *M. hyopneumoniae* cells were prepared as described under "Fermentation and Inactivation" in Example 1 above. The inactivated fermentation fluid was centrifuged at ~20,000×g (Sorvall RCSB) for 30 min. and the supernatant was sterilized via 0.2 uM filtration. One hundred fifteen mls of rProtein A resin (part number 12-1279-04, MAbSelect, GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 1.2 liters of the clarified/filtered *M. hyopneumoniae* antigen containing fluids were passed through the resin at a flow rate of 120 cm/hr. The flow through was collected and sterilized via 0.2 μM filter.

T07: Inactivated *M. hyopneumoniae* cells were prepared as described under "Fermentation and Inactivation" in Example 1 above. The inactivated fermentation fluid was clarified by via tangential flow filtration. Briefly, a polyether sulfone filter (GE HealthCare, part number 56-4102-71) with nominal pore size of 0.2 μM was sanitized with 0.5N sodium hydroxide solution followed by extensive rinsing with sterile USP water. Inactivated *mycoplasma* culture fluid was introduced to the apparatus at a recirculation rate targeted to 14.6 L/minute and a transmembrane pressure of 2-3.4 PSI. Clarification was performed at room temperature. Filter permeate was collected and stored at 2-8 C until further processing. One hundred fifteen mls of rProtein A resin (part number 12-1279-04, MAbSelect, GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 2.3 liters of the clarified/filtered *M. hyopneumoniae* antigen containing fluids were passed through the resin at a flow rate of 120 cm/hr. The flow through was collected and sterilized via 0.2 μM filter.

T08: Inactivated *M. hyopneumoniae* cells were prepared as described under "Fermentation and Inactivation" above. The inactivated fermentation fluid was centrifuged at ~20,000×g (Sorvall RCSB) for 30 min. and the supernatant was sterilized via 0.2 uM filtration. One hundred fifteen mls of rProtein A Sepharose (part number 17-5199-03 GE Healthcare) was packed into a chromatography column (5×6 cm). After removal of the storage buffer and treatment with 2 column volumes of 1M acetic acid, the resin was equilibrated with 5 column volumes of 50 mM NaPO4/1M NaCl buffer, pH 7.01. Approximately 1.2 liters of the clarified/filtered *M. hyopneumoniae* antigen containing fluids were passed through the resin at a flow rate of 120 cm/hr. The flow through was collected and sterilized via 0.2 uM filter.

The experimental vaccine formulations were prepared with M.hyo antigens processed according to treatments T02-T08 above. T02, T03 and T04 corresponded to positive controls. In addition, Treatment T01 corresponded to a placebo (sterile saline).

These experimental formulations are described in Table 11 below. The M.hyo antigen corresponds to the M.hyo antigen from global M.hyo seed, Protein A treated supernatant. The information in the "Protein A Treatment" column indicates whether the M.hyo supernatant was treated with Protein A either before or after fermentation.

TABLE 11

PCV2/M.hyo Experimental Vaccine Formulations Used for M. hyo Efficacy Study in SP-Oil Adjuvant

| Treatment | Serial No. | PCV1-2 Ag | M. hyo Ag | Protein A Treatment | Supernatant Clarification Method | Protein A Brand | Adjuvant | Other |
|---|---|---|---|---|---|---|---|---|
| T01 | L0311AS11 | | | NA | | | | Sterile Saline |
| T02 | A828718 | NA | 13 | Expired RespiSure One | | | Amphigen | NA |
| T03 | L0711RK09 | 1.5 RP | 7.5 RP | M. hyo without Protein A treatment and with PCV-2 | | | 10% SP Oil | |
| T04 | L0711RK10 | NA | | M. hyo without Protein A treatment and without PCV-2 | | | | |
| T05 | L0711RK11 | 1.5 RP | | Before | NA | Sepharose | | |
| T06 | L0711RK12 | | | After | Centrifuge | MAbSelect | | |
| T07 | L0711RK13 | | | After | Filter | MAbSelect | | |
| T08 | L0711RK14 | | | After | Centrifuge | Sepharose | | |

Figures 8A, 8B:
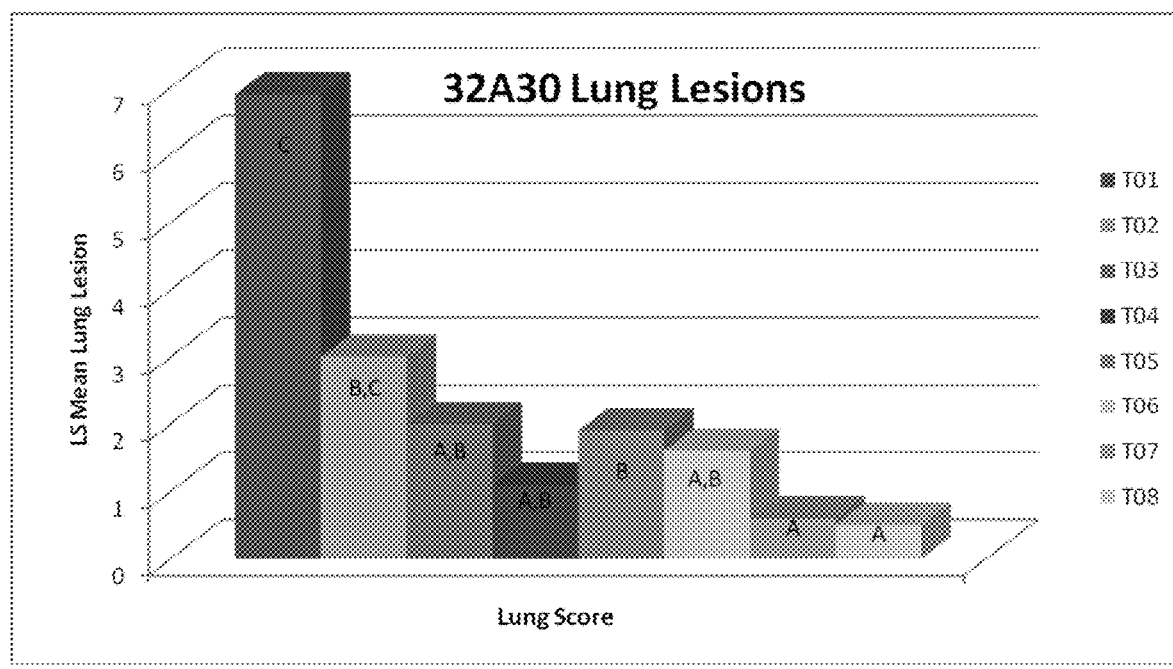
FIGS. 8A and 8B depict the M.hyo efficacy of the PCV2/M.hyo experimental vaccine formulations in SP-oil. The lung scores for formulations employing M.hyo treatments T02-T08 vs. a placebo (T01) are depicted graphically in FIG. 8A. The table in FIG. 8B depicts the contrast of treatments T02-T08 with the placebo.

Pigs at 3 weeks of age were intramuscularly inoculated with a single dose of the different vaccine formulations described in Table 11 above. There were 18 pigs included in each treatment group. Animals were challenged 21 days after vaccination with a virulent M.hyo field isolate. Animals were necropsied 28 days after challenge and the lungs were removed and scored for consolidation consistent with M.hyo infection. FIG. 8A and FIG. 8B show the lung lesion scores for the respective treatment groups. Statistical significance was determined by a Mixed Model Analysis of lung scores for each group.

The lung lesion results depicted in FIGS. 8A and 8B indicate that of all the treatments, only two (T07 and T08) had 100% of pigs in the <5% lung lesion category. It is noted that strong statistical difference were observed in this study.

The results in the present example demonstrate significant M.hyo efficacy in a 1-bottle PCV2/M.hyo experimental formulation employing the Protein A-treated M.hyo supernatant and utilizing SP-oil as the adjuvant. Additionally, Example 7 above demonstrated PCV2 efficacy in a 1-bottle PCV2/M.hyo formulation employing the Protein A-treated M.hyo supernatant and utilizing SP-oil as the adjuvant. Taken together, both M.hyo and PCV2 efficacy have been demonstrated in the 1-bottle PCV2/M.hyo combinations employing Protein A-treated M.hyo supernatant.

Example 10: In Vivo Safety of Experimental PCV2/M.Hyo Experimental Vaccines

This study was conducted to evaluate in vivo safety of experimental PCV2-M.hyo vaccines formulated at maximum antigen dose in various adjuvant formulations in the host animal when given at the youngest age (3 weeks of age). Different adjuvant platforms were evaluated in order to determine which of these platforms provided an acceptable safety profile based on temperature, injection site reactions and clinical observations. A 20% SLCD/10% SP-oil formulation was used as a positive ("unsafe") control due to historic issues with injection site reactions observed by this investigative group and others.

Processing of Fluids:

All vaccines were prepared with inactivated *M. hyopneumoniae* antigen as described under "Fermentation and Inactivation" in Example 1. M.hyo whole bulk antigen was used since it was known to contain soluble and insoluble M.hyo antigens, in addition to the immunoglobulins and immunocomplexes that would be removed upon protein A treatment. It is reasonable to conclude that removal of insoluble cell debris and immunuoglobulins and immunocomplexes will only further enhance the safety of the vaccine formulations. The intention of this study was to stringently test the safety of the various adjuvant formulations containing PCV2 antigen and M.hyo antigen. The PCV2 and M.hyo antigens were formulated at maximum release levels to further assess safety. These experimental formulations are described in Table 12 below. IVP indicates Investigational Veterinary Product (IVP).

TABLE 12

PCV2/M.hyo Experimental Vaccine Formulations Used for Safety Study

| IVP Serial | PCV1-2 Ag | M Hyo* Ag | Adjuvant | Other | Minimum Vaccine Vol. (mL) |
|---|---|---|---|---|---|
| 87-244-DK (Placebo) | | | NA | Sterile Saline | NA |
| L0411RK15 | 7.8 RP | 13 RP | 10% SP Oil | NA | 200 |
| L0411RK16 | | | 5% Amphigen | | 200 |
| L0611RK05 | | | 5% Amphigen + 5% SLCD | | 200 |
| L0611RK06 | | | 20% SLCD + 10% SP Oil | | 200 |

* M hyo antigen = from global M hyo seed (whole bulk antigen).

The safety parameters employed in this study were rectal temperature profile and injection site reaction. The results of this study indicated that all candidate adjuvant platforms provided an acceptable safety profile in terms of rectal temperature profile and clinical observations (results not shown). Only the 20% SLCD+10% SP-oil (i.e., positive control) was significantly different than the placebo vaccine and had a number of severe injection site reactions (results not shown).

Figure 9:
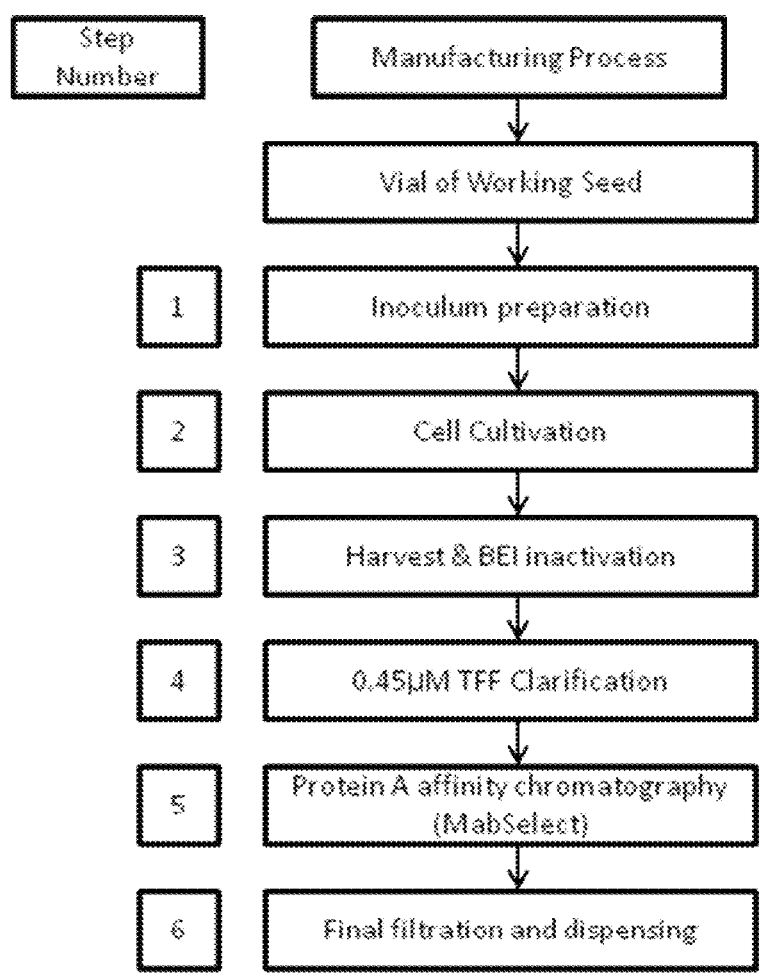
FIG. 9 is a flowchart which shows one embodiment of a manufacturing process used to prepare PCV2-compatible Protein-A treated M.hyo antigen.

Example 11: Preparation of Protein a Treated M.Hyo Antigen for Pivotal Studies FIG. 9 is a flowchart which shows one embodiment of a manufacturing process used to prepare PCV2 compatible Protein-A treated M.hyo antigen. Inactivated whole cultures of M.hyo were clarified of cells via tangential flow filtration. Briefly, a polyether sulfone filter (GE Healthcare, part number 56-4102-49) with nominal pore size of 0.45 µM was sanitized with 0.5N sodium hydroxide solution followed by extensive rinsing with sterile USP water. Inactivated *mycoplasma* culture fluid was introduced to the apparatus at a recirculation rate targeted to 11.0 L/minute and a transmembrane pressure of ~5 PSI. Clarification was performed at room temperature. Filter permeate was collected and stored at 2-8° C. until further processing.

Following clarification, antigen containing fluids were treated with protein A resin to reduce antibody levels. Briefly, MAbSelect protein A resin (GE Healthcare) was packed into a glass column to a height of 12 cm. The resin was equilibrated with 5 column volumes of 50 mM sodium phosphate, 250 mM NaCl buffer (pH 7.0). Antigen containing fluid, equivalent to 10 column volumes, was loaded onto the resin at a linear flow rate of 100 cm/hour. The column flow through was collected and filter sterilized through a 0.2 micron filter. Regeneration of the column was achieved by flowing 3 column volumes of 25 mM acetate solution at pH 3.7 followed by 4 column volumes of 1M acetic acid solution. Anti-PCV2 antibodies and *M. hyopneumoniae* antigen levels were measured in the final antigen fluid via PCV2 specific antibody ELISA and p46 antigen quantification ELISA, respectively.

Example 12: Evaluation of Virucidal Activity Against PRRS Virus

The studies presented in this example were designed to evaluate the various adjuvant platforms for virucidal activity against PRRS virus. Initial experiments focused on adjuvant alone (i.e., the formulations did not contain PCV or M.hyo antigens). The adjuvant evaluation for PRRS virucidal activity is presented in FIG. 10. Preliminary virucidal assessment indicated that 10% SP-oil, 0.2% Carbopol and 2.5% Amphigen are non-virucidal to PRRS virus. In contrast, the 20% SLCD adjuvant appeared to be virucidal to PRRS virus.

Further studies were performed to evaluate whether the PCV/M.hyo formulations adjuvanted with the different adjuvant platforms were non-virucidal to PRRS virus. These results are presented in Table 13, wherein the symbol * indicates those vaccine serials which were virucidal to PRRSV.

TABLE 13

Results of PRRS Virucidal Assay with Different Formulations

| Vaccine Serial Used in Studies of Examples 7, 8, 10 | | | Potency | | PRRS Virucidal | |
|---|---|---|---|---|---|---|
| | | | p46 RP | PCV2 NVSL | | |
| Study | Description | Serial # | (ru/ds) | RP | A | B |
| Examples 7, 8, 10 | Sterile Saline (0.9% Sodium chloride) | 87-244-DK (Placebo) | | | | |
| Examples 7, 8 | cPCV (RP 1.6) + *M Hyo* Prot A treated (RP 7.5) in 10% SP Oil | L0411RK08 | 7.1 | 1.29 | −0.10 | −0.13 |
| Examples 7, 8 | cPCV (RP 1.6) + *M Hyo* Prot A treated (RP 7.5) in 5% Amphigen | L0411RK09 | 7.3 | 1.33 | −0.10 | +0.14 |
| Examples 7, 8 | cPCV (RP 1.6) + *M Hyo* Prot A treated (RP 7.5) in 5% Amph + 5% SLCD | L0611RK03 | 6.9 | 1.15 | −0.36 | −0.33 |
| Example 7 | cPCV (RP 1.6) monovalent in 20% SLCD | L0611RK04 | | 1.50 | −1.86* | −0.50 |
| Example 8 | Expired RespiSure One serial | A827870 | 12.6 | | | |
| Example 10 | cPCV (RP 7.8) + *M Hyo* Whole Bulk (RP 13.3) in 10% SP Oil | L0411RK15 | 14 | 1.03 | −0.32 | −0.03 |
| Example 10 | cPCV (RP 7.8) + *M Hyo* Whole Bulk (RP 13.3) in 5% Amphigen | L0411RK16 | 15.5 | 1.12 | −0.36 | −0.53 |
| Example 10 | cPCV (RP 7.8) + *M Hyo* Whole Bulk (RP 13.3) in 5% Amph + 5% SLCD | L0611RK05 | 17.5 | 1.50 | −0.54 | −0.33 |
| Example 10 | cPCV (RP 7.8) + *M Hyo* Whole Bulk (RP 13.3) in 20% SLCD + 10% SP Oil | L0611RK06 | 15.9 | 1.13 | −1.93* | −0.99* |

*Indicates Virucidal (>0.7 log loss)
A - Virucidal assay control GMT ~5.53 log/mL
B - Virucidal assay control GMT ~6.42 log/mL The results presented in Table 13 above indicate that 10% SP-oil is non-virucidal to PRRS virus.

Further PCV/M.hyo vaccine serials were prepared using 10% SP-oil as the adjuvant (Table 14). The antigenic potency of these vaccine serials was compared to a Reference PCV/M.hyo vaccine serial (L1211RK15) which contained 0.688% of a 20× concentrate of PCV2 antigen (prepared as described in Example 2); and 9.40% of M.hyo antigen prepared as described in Example 11. The results shown in Table 14 below further indicate that 10% SP-oil is non-virucidal to PRRS virus. The test sample values in Table 14 were each higher (+ sign) than the virucidal assay control, which had a geometric mean titer (GMT) of about 5.9±0.5 log/ml.

Results of Virucidal Assay with Different PCV/M.hyo Formulations Adjuvanted with 10% SP-oil

| Vaccine Serial Used Description | Serial # | Potency | | PRRS Virucidal log10 TCID50/mL |
|---|---|---|---|---|
| | | p46 RP (ru/ds) Reference L1211RK15 | PCV2 NVSL Reference L1211RK15 | |
| Sterile Diluent (sterile water) | 1949122 | na | na | |
| cPCV + M Hyo Prot A treated in 10% SP Oil | L0912RK12 | 1.62 | 2.60 | +0.58 |
| cPCV + M Hyo Prot A treated in 10% SP Oil | L0912RK10 | 0.88 | 1.23 | +0.58 |
| cPCV + M Hyo Prot A treated in 10% SP Oil | L0912RK11 | 1.24 | 2.62 | +0.58 |
| cPCV + M Hyo Prot A treated in 10% SP Oil | L0912RK08 | 1.08 | 1.03 | +0.91 |
| cPCV +M Hyo Prot A treated in 10% SP Oil | L0912RK09 | 1.65 | 2.06 | +0.50 |

Virucidal Assay control GMT ~ 5.9 ± 0.5 log/ml

The results presented in this example demonstrate that 10% SP-oil is non-virucidal to PRRS virus. The results presented in this example further demonstrate that the PCV/M.hyo formulation adjuvanted with 10% SP-oil was among those vaccine serials which were considered non-virucidal to PRRS virus (Table 13 and Table 14). In conclusion, the PCV/M.hyo formulation adjuvanted with 10% SP-oil was considered an effective platform on which to base a trivalent combination including PCV, M.hyo, and PRRS virus.

Example 13: Preparation of a PCV/M.Hyo/PRRS Combination Vaccine

A PCV/M.hyo formulation adjuvanted with an adjuvant platform which is non-virucidal to PRRS virus (see Tables 13 and 14 above), is provided as a ready-to-use in one-bottle liquid composition. This 1-bottle PCV/M.hyo formulation employs Protein A-treated M.hyo supernatant. Both M.hyo and PCV2 efficacy have been demonstrated in such PCV2/M.hyo formulations employing M.hyo Protein A-treated supernatant (see Examples 7-9). In the present example, this divalent PCV2/M.hyo formulation is combined with a monovalent PRRS virus antigen.

In one embodiment, a PCV/M.hyo combination in 10% SP-oil and corresponding to one of the vaccine serials L0711RK11, L0711RK12, L0711RK13 and L0711RK14 in Table 11 above is provided as a ready-to-use in one bottle liquid composition. The results presented in Example 12 above demonstrated that 10% SP-oil is non-virucidal to PRRS virus. Example 12 also demonstrated that PCV2/M.hyo formulations adjuvanted with 10% SP-oil were among those vaccine serials which were considered non-virucidal to PRRS virus. In the present example, such a 1-bottle PCV2/M.hyo liquid composition is used to re-hydrate a lyophilized genetically modified live PRRS virus composition contained in a second bottle, such that all antigens are contained in a single bottle prior to being administered to a pig of a suitable age (e.g., at 3 weeks of age or older).

In one embodiment, the PRRS virus has the genomic sequence corresponding to SEQ ID NO: 16 or a variant thereof. In another embodiment, the PRRS virus employed in the trivalent composition is the PRRS virus isolate designated ISU-55, which was deposited in the ATCC under the accession number VR 2430. Suitable amounts of the respective antigens are described herein. Desirably, all antigens are administered in a single dose to the pig.

What is claimed is:

1. A protein-A or protein-G treated *Mycoplasma hyopneumoniae* (M.hyo) antigen that is compatible with antigens from other swine pathogens, wherein the M.hyo antigen is an M.hyo culture supernatant.

2. The antigen of claim 1, wherein the M.hyo antigen is inactivated.

3. The antigen of claim 1, wherein the M.hyo culture supernatant has been separated from insoluble cellular material by centrifugation, filtration, or precipitation and is substantially free of both (i) IgG and (ii) immunocomplexes comprised of antigen bound to immunoglobulin.

4. An immunogenic composition comprising the antigen of claim 1.

5. The composition of claim 4, wherein the composition further comprises at least one additional antigen that is protective against a swine pathogen selected from the group consisting of porcine circovirus type 2 (PCV2), porcine reproductive and respiratory syndrome virus (PRRSV), porcine parvovirus (PPV), *Haemophilus parasuis*, *Pasteurella multocida*, *Streptococcum suis*, *Staphylococcus hyicus*, *Actinobacillus pleuropneumoniae*, *Bordetella bronchiseptica*, *Salmonella choleraesuis*, *Salmonella enteritidis*, *Erysipelothrix rhusiopathiae*, *Mycoplasma hyorhinis*, *Mycoplasma hyosynoviae*, leptospira bacteria, *Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Porcine enteroviruses, Encephalomyocarditis virus, a pathogen causative of Aujesky's Disease, Classical Swine fever (CSF) and a pathogen causative of Swine Transmissible Gastroenteritis, or combinations thereof.

6. The composition of claim 5, wherein the at least one additional antigen is a porcine circovirus type 2 (PCV2) antigen, a PRRS virus antigen, a *Lawsonia intracellularis* antigen or a combination thereof.

7. The composition of claim 6, wherein the composition elicits a protective immune response against M.hyo and PCV2.

8. The composition of claim 6, wherein the composition elicits a protective immune response in a pig against M.hyo, PCV2 and PRRS virus.

9. The composition of claim 6, wherein the composition elicits a protective immune response in a pig against M.hyo, PCV2 and *Lawsonia intracellularis*.

10. The composition of claim 6, wherein the PCV2 antigen is in the form of a chimeric type-1-type 2 circovirus, said chimeric virus comprising an inactivated recombinant porcine circovirus type 1 expressing the porcine circovirus type 2 ORF2 protein.

11. The composition of claim 6, wherein the PCV2 antigen is in the form of a recombinant ORF2 protein.

12. The composition of claim 11, wherein the recombinant ORF2 protein is expressed from a baculovirus vector.

13. The composition of claim 4, wherein the composition further comprises an adjuvant.

14. The composition of claim 13, wherein the adjuvant is selected from the group consisting of an oil-in-water adjuvant, a polymer and water adjuvant, a water-in-oil adjuvant, an aluminum hydroxide adjuvant, a vitamin E adjuvant and combinations thereof.

15. The composition of claim 4, wherein the composition further comprises a pharmaceutically acceptable carrier.

16. The composition of claim 4, wherein the composition elicits a protective immune response against M.hyo when administered as a single dose administration.

17. The composition of claim 5, wherein the composition elicits a protective immune response against M.hyo and the at least one additional swine pathogen when administered as a single dose administration.

18. A method of immunizing a pig against *Mycoplasma hyopneumoniae* (M.hyo) which comprises administering to the pig the composition of claim 4.

19. The method of claim 18, wherein the composition is administered intramuscularly, intradermally, transdermally, or subcutaneously.

20. The method of claim 18, wherein the composition is administered in a single dose.

21. The method of claim 18, wherein the composition is administered in conjunction with at least one additional antigen that is protective against a swine pathogen selected from the group consisting of porcine circovirus type 2 (PCV2), porcine reproductive and respiratory syndrome virus (PRRSV), porcine parvovirus (PPV), *Haemophilus parasuis*, *Pasteurella multocida*, *Streptococcum suis*, *Staphylococcus hyicus*, *Actinobacillus pleuropneumoniae*, *Bordetella bronchiseptica*, *Salmonella choleraesuis*, *Salmonella enteritidis*, *Erysipelothrix rhusiopathiae*, *Mycoplasma hyorhinis*, *Mycoplasma hyosynoviae*, leptospira bacteria, *Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Porcine enteroviruses, Encephalomyocarditis virus, a pathogen causative of Aujesky's Disease, Classical Swine fever (CSF) and a pathogen causative of Swine Transmissible Gastroenteritis, or combinations thereof.

22. The method of claim 18, wherein the composition is administered to pigs having maternally derived antibodies against M.hyo.

23. The method of claim 21, wherein the composition is administered to pigs having maternally derived antibodies against M.hyo and the at least one other swine pathogen.

24. The method of claim 18, wherein the composition is administered to pigs at 3 weeks of age or older.

25. A kit comprising a protein-A or protein-G treated *Mycoplasma hyopneumoniae* (M.hyo) antigen that is compatible with antigens from other swine pathogens, wherein the M.hyo antigen is an M.hyo culture supernatant.

26. The kit of claim 25, wherein the M.hyo culture supernatant has been separated from insoluble cellular material by centrifugation, filtration, or precipitation and is substantially free of both (i) IgG and (ii) immunocomplexes comprised of antigen bound to immunoglobulin.

27. The kit of claim 25, further comprising comprises at least one additional antigen that is protective against a swine pathogen selected from the group consisting of porcine circovirus type 2 (PCV2), porcine reproductive and respiratory syndrome virus (PRRSV), porcine parvovirus (PPV), *Haemophilus parasuis*, *Pasteurella multocida*, *Streptococcum suis*, *Staphylococcus hyicus*, *Actinobacillus pleuropneumoniae*, *Bordetella bronchiseptica*, *Salmonella choleraesuis*, *Salmonella enteritidis*, *Erysipelothrix rhusiopathiae*, *Mycoplasma hyorhinis*, *Mycoplasma hyosynoviae*, leptospira bacteria, *Lawsonia intracellularis*, swine influenza virus (SIV), *Escherichia coli* antigen, *Brachyspira hyodysenteriae*, porcine respiratory coronavirus, Porcine Epidemic Diarrhea (PED) virus, rotavirus, Porcine enteroviruses, Encephalomyocarditis virus, a pathogen causative of Aujesky's Disease, Classical Swine fever (CSF) and a pathogen causative of Swine Transmissible Gastroenteritis, or combinations thereof.

28. The kit of claim 27, wherein the at least one additional antigen is a porcine circovirus type 2 (PCV2) antigen, a PRRS virus antigen, a *Lawsonia intracellularis* antigen or a combination thereof.

* * * * *